US009861633B2

(12) United States Patent
Ali et al.

(10) Patent No.: US 9,861,633 B2
(45) Date of Patent: Jan. 9, 2018

(54) METHODS OF TREATING UROTHELIAL CARCINOMA

(71) Applicant: FOUNDATION MEDICINE, INC., Cambridge, MA (US)

(72) Inventors: Siraj Mahamed Ali, Cambridge, MA (US); Matthew J. Hawryluk, Watertown, MA (US); Jeffrey S. Ross, Lebanon Springs, NY (US); Philip James Stephens, Lexington, MA (US)

(73) Assignee: FOUNDATION MEDICINE, INC., Cambridge, MA (US)

( * ) Notice: Subject to any disclaimer, the term of this patent is extended or adjusted under 35 U.S.C. 154(b) by 0 days.

(21) Appl. No.: 14/333,368

(22) Filed: Jul. 16, 2014

(65) Prior Publication Data

US 2015/0023965 A1 Jan. 22, 2015

Related U.S. Application Data

(60) Provisional application No. 61/847,532, filed on Jul. 17, 2013.

(51) Int. Cl.
*C12Q 1/68* (2006.01)
*A61K 31/517* (2006.01)
*A61K 47/48* (2006.01)
*A61K 31/5365* (2006.01)
*C07K 14/82* (2006.01)
*C07K 16/32* (2006.01)
*A61K 45/06* (2006.01)
*A61K 31/475* (2006.01)
*A61K 31/519* (2006.01)
*A61K 31/704* (2006.01)
*A61K 31/7105* (2006.01)
*A61K 31/713* (2006.01)
*A61K 33/24* (2006.01)

(52) U.S. Cl.
CPC .......... *A61K 31/517* (2013.01); *A61K 31/475* (2013.01); *A61K 31/519* (2013.01); *A61K 31/5365* (2013.01); *A61K 31/704* (2013.01); *A61K 31/713* (2013.01); *A61K 31/7105* (2013.01); *A61K 33/24* (2013.01); *A61K 45/06* (2013.01); *A61K 47/48384* (2013.01); *A61K 47/48569* (2013.01); *C07K 14/82* (2013.01); *C07K 16/32* (2013.01); *C12Q 1/6886* (2013.01); *C12Q 2600/106* (2013.01)

(58) Field of Classification Search
None
See application file for complete search history.

(56) References Cited

U.S. PATENT DOCUMENTS 5,547,835 A 8/1996 Koster
5,605,798 A 2/1997 Koster

| | | | |
|---|---|---|---|
| 6,455,258 | B2 | 9/2002 | Bastian et al. |
| 2004/0086884 | A1 | 5/2004 | Beach et al. |
| 2006/0034840 | A1 | 2/2006 | Agus |
| 2009/0318480 | A1 | 12/2009 | Solca |
| 2010/0029498 | A1 | 2/2010 | Gnirke et al. |

FOREIGN PATENT DOCUMENTS

| | | | |
|---|---|---|---|
| WO | WO 02/22636 | * | 3/2002 |
| WO | 2010093465 A1 | | 8/2010 |
| WO | 2011147986 A1 | | 12/2011 |
| WO | 2012092426 A1 | | 7/2012 |
| WO | 2013063229 A1 | | 5/2013 |
| WO | WO 2013/063229 | * | 5/2013 |
| WO | WO 2014/089127 | * | 11/2013 |
| WO | WO 2013/170263 | * | 6/2014 |

OTHER PUBLICATIONS

De Greve et al (Lung Cancer, Apr. 2012, 76:123-127).*
Peyromaure et al (European Urology 2005, 48:771-778).*
Hussain et al (Journal of Oncology, 2007, 25:2218-2224).*
Lae et al (Annals of Oncology, 2010, 21:815-819).*
Huang et al (Mar. 5, 2013, US and Canadian Academy of Pathology (USCAP) Meeting, Poster Session, [908]).*
Schneider et al (Journal of Urology, vol. 189, No. 4S, Supplement, May 5, 2013, p. e160, abstract 395).*
Greulich et al (PNAS, Sep. 2012, 109:14476-14481).*
Bose et al (Cancer Discovery, 2013, 3:224-237, published online Dec. 7, 2012).*
Weigelt et al (Cancer Discovery, Feb. 2013, 3:145-147).*
Sangoi et al (Modern pathology, 2009, 22:660-667).*
Ching et al (Modern Pathology, 2011, 24:1111-1119).*
Hussain et al (Journal of Clinical Oncology, 2007, 25:2218-2224).*
Coogan et al (Journal of Urology, 2004, 63:786-790, IDS).*
Kamat et al, "Micropapillary Bladder Cancer—A Review of the University of Texas M. D. Anderson Cancer Center Experience With 100 Consecutive Patients" Cancer, vol. 110, No. 1, pp. 62-67 (2007).
Chen et al., "Breast Carcinoma with Micropapillary Features: Clinicopathologic Study and Long-Term Follow-Up of 100 Cases." International Journal of Surgical Pathology, vol. 16 No. 2, pp. 155-163 (2008).
Chen et al., "Her2 amplification distinguishes a subset of non-muscle-invasive bladder cancers with a high risk of progression," J. Clin. Pathol., vol. 66, pp. 113-119 (2013).
Fleischmann et al., "Her2 Amplification is Significantly More Frequent in Lymph Node Metastases From Urothelial Bladder Cancer Than in the Primary Tumours." European Urology, vol. 60, pp. 350-357 (2011).
Gardiner et al., "An immunohistological demonstration of c-erbB-2 oncoprotein expression in primary urothelial bladder cancer." Urol. Res., vol. 20, pp. 117-120 (1992).
Gorin et al., "Diagnosis and Treatment of Bladder Cancer: How Can We Improve?", Postgrad Med., 124(3):28-36; May 2012.

(Continued)

*Primary Examiner* — Laura B Goodard
(74) *Attorney, Agent, or Firm* — Lando & Anastasi, LLP

(57) ABSTRACT

Methods and compositions for treating a urothelial and/or a micropapillary carcinoma, such as a micropapillary urothelial carcinoma are disclosed.

49 Claims, 36 Drawing Sheets

(56) References Cited

OTHER PUBLICATIONS

Lopez et al., "Micropapillary transitional cell carcinoma of the urinary bladder." Histopathology, vol. 34, pp. 561-562 (1999).
Noon et al., "Bladder Cancer in 2012: Challenging current paradigms." Nat. Rev. Urol., vol. 10, pp. 67-68 (2013).
Samaratunga et al., "Micropapillary variant of urothelial carcinoma of the urinary bladder; a clinicopathological and immunohistochemical study." Histopathology, vol. 45, pp. 55-64 (2004).
Sangoi et al., "Interobserver Reproducibility in the Diagnosis of Invasive Micropapillary Carcinoma of the Urinary Tract Among Urologic Pathologists." Am. J. Surg. Pathol, vol. 34 No. 9, pp. 1367-1376 (2010).
Ather et al., "Dacomitinib, an Irreversible Pan-ErbB Inhibitor Significantly Abrogates Growth in Head and Neck Cancer Models That Exhibit Low Response to Cetuximab" PLoS One, 8(2):e56112 (2013).
Aurisicchio et al., "The promise of anti-ErbB3 monoclonals as new cancer therapeutics" Oncotarget, 3(8):744-758 (2012).
Berlin et al., "A first-in-human phase I study of U3-1287 (AMG 888), a HER3 inhibitor, in patients (pts) with advanced solid tumors" J Clin Oncol, 29:Supplement Abstract 3026 (Poster) (2011).
Butler et al., "Allpaths: De novo assembly of whole-genome shotgun microreads" Genome Res., 18:810-820 (2008).
Ching et al., "HER2 gene amplification occurs frequently in the micropapillary variant of urothelial carcinoma: analysis by dual-color in situ hybridization" Modern Pathology, 24:1111-1119 (2011).
Cronin et al., "Measurement of Gene Expression in Archival Paraffin-Embedded Tissues: Development and Performance of a 92-Gene Reverse Transcriptase-Polymerase Chain Reaction Assay" American Journal of Pathology, 164(1):35-42 (2004).
De Oliveira et al., "Micropapillary Lung Adenocarcinoma" American Journal of Clinical Pathology, 131:694-700 (2009).
Ginzinger, et al., "Measurement of DNA Copy Number at Microsatellite Loci Using Quantitive PCR Analysis" Cancer Research, 60:5405-5409 (2000).
Gnirke et al., "Solution hybrid selection with ultra-long oligonucleotides for massively parallel targeting sequencing" Nature Biotechnology, 27(2):182-189 (2009).
Hickinson et al., "AZD8931, an Equipotent, Reversible Inhibitor of Signaling by Epidermal Growth Factor Receptor, ERBB2 (HER2), and ERBB3: A Unique Agent for Simultaneous ERBB Receptor Blockade in Cancer" Clin Cancer Res., 16(4):1159-1169 (2010).
Huang et al., "Dual Targeting of EGFR and HER3 with MEHD7945A Overcomes Acquired Resistance to EGFR Inhibitors and Radiation" Cancer Research, 73(2):824-833 (2013).
International Search Report and Written Opinion for International Application No. PCT/US2014/46857 mailed Feb. 6, 2015.
Jani et al., Discovery and Pharmacologic Characterization of CP-724,714, a selective ErbB2 Tyrosine Kinase Inhibitor Cancer Res., 67(20):9887-9893 (2007).
Kallioniemi, et al., "ERBB2 amplification in breast cancer analyzed by fluorescence in situ hybridization" PNAS USA, 89:5321-5325 (1992).
Mirschberger et al., "RG7116, a Therapeutic Antibody That Binds the Inactive HER3 Receptor and Is Optimized for Immune Effector Activation" Cancer Research, 73(16):5183-5194 (2013).
Nagasawa et al., "Novel HER2 selective tyrosine kinase inhibitor, TAK-165, inhibits bladder, kidney and androgen-independent prostate cancer in vitro and in vivo" International Journal of Urology, 13(5):587-592 (2006).
Nicolas et al., "Micropapillary carcinoma of the urinary bladder: report of a case and review of its cytologic features" Diagn. Cytopathol., 39(10):784-787 (2011).
Pao et al., "Rational, biologically based treatment of EGFR-mutant non-small-cell lung cancer" Nature Reviews Cancer, 10:760-774 (2010).

Peethambaram et al., "A Phase I Trial of Immunotherapy with Lapuleucel-T (APC8024) in Patients with Refractory Metastatic Tumors that Express HER-2/neu" Clin. Cancer Res., 15:5937-5944 (2009).
Rouge et al., "A Novel Epidermal Growth Factor Receptor Inhibitor Promotes Apoptosis in Non-Small Cell Lung Cancer Cells Resistanc to Erlotinib" Cancer Research, 67(13):6253-6262 (2007).
Sanger et al., "DNA sequencing with chain-terminating inhibitors" PNAS USA, 74(12):5463-5467 (1977).
Shoeberl et al., "An ErbB3 Antibody, MM-121, Is Active in Cancers with Ligand-Dependent Activation" Cancer Research, 70(6):2485-94 (2010).
Singh et al., "Surface epithelial changes in uterine endometrioid carcinoma mimicking micropapillary serous borderline tumor of ovary: report of two cases and review of the literature" Diagnostic Pathology, 6:13 (Jan. 2011).
Specht et al., "Quantitative Gene Expression Analysis in Microdissected Archival Formalin-Fixed and Paraffin-Embedded Tumor Tissue" American Journal of Pathology, 158(2):419-429 (2001).
Trapnell and Salzberg, "How to map billions of short reads onto genomes" Nature Biotechnology, 27:455-457 (2009).
Tsang et al., "Beyond trastuzumab: novel therapeutic strategies in HER2-positive metastatic breast cancer" British Journal of Cancer, 106:6-13 (2012).
Vincent et al., "AV-203, a humanized ERBB3 inhibitory antibody inhibits ligand-dependent and ligand-independent ERBB3 signaling in vitro and in vivo" Cancer Research, 72(8):Supplement AM2012-2509 (Poster) (2012).
Warren et al., "Assembling millions of short DNA sequences using SSAKE" Bioinformatics, 23(4):500-501 (2007).
Wheeless et al., "Bladder Irrigation Specimens Assayed by Fluorescence In Situ Hybridization to Interphase Nuclei" Cytometry, 17(4):319-326 (1994).
Wong et al., "Preclinical Antitumor Activity of BMS-599626, a pan-HER Kinase Inhibitor That Inhibits HER1/HER2 Homodimer and Heterodimer Signaling" Clin. Cancer Res., 12(20):6186-6193 (2006).
Zerbino and Birney, "Velvet: Algorithims for de novo short read assembly using de Bruijn graphs" Genome Research, 18:821-829 (2008).
"Foundation Medicine Discover High Incidence of Clinically Actionable ERBB2 (HER2) Alterations in Aggressive Form of Bladder Cancer; Data Published in Clinical Cancer Research" Press release dated Jan. 9, 2014.
Ali et al., "Response of an ERBB2-Mutated Inflammatory Breast Carcinoma to Human Epidermal Growth Factor Receptor 2-Targeted Therapy" J Clin Oncol. Sep. 27, 2013 [Epub ahead of print).
Amin et al., "Histological variants of urothelial carcinoma: diagnostic therapeutic and prognostic implications" Modern Pathology, vol. 22, pp. 96-118 (2009).
Amin et al., "Micropapillary Variant of Transitional Cell Carcinoma of the Urinary Bladder—Histologic Pattern Resembling Ovarian Papillary Serous Carcinoma" The American Journal of Surgical Pathology, vol. 18(12) pp. 1224-1232 (1994).
Bose et al., "Activating HER2 mutations in HER2 gene amplification negative breast cancer" Cancer Discov. 3(2) pp. 224-237 (2013).
Calabro et al., "Neoadjuvant and Adjuvant Chemotherapy in Muscle-Invasive Bladder Cancer" European Urology vol. 55, pp. 348-358 (2009).
del Carmen et al., "Uterine papillary serous cancer: A Review of the Literature" Gynecologic Oncology, vol. 127, pp. 651-661 (2012).
Greulich et al., "Functional analysis of receptor tyrosine kinase mutations in lung cancer identifies oncogenic extracellular domain mutations of ERBB2" Proc Natl Acad Sci, 109(36), pp. 14476-14481 (2012).
Greulich et al., "The Genomics of Lung Adenocarcinoma: Opportunities for Targeted Therapies" Genes & Cancer, vol. 1, No. 12, pp. 1200-1210 (2010).
Herter-Sprie et al., "Activating mutations in ERBB2 and their impact on diagnostic and treatment" Front Oncol. vol. 3, Article 96, pp. 1-10 (2013).

(56) References Cited

OTHER PUBLICATIONS

Kamat et al., "Micropapillary Bladder Cancer—A Review of the University of Texas M. D. Anderson Cancer Center Experience With 100 Consecutive Patients" Cancer, vol. 110, No. 1, pp. 62-67 (2007).

Kamiya et al., "Histopathological features and prognostic significance of the micropapillary pattern in lung adenocarcinoma" Modern Pathology, vol. 21, pp. 992-1001 (2008).

Kaufman et al., "Bladder cancer" Lancet, vol. 374, pp. 239-249 (2009).

Lee et al., "Epidermal Growth Factor Receptor Activation in Glioblastoma Through Novel Missense Mutation in the Extracellular Domain" PLoS Medicine, vol. 3, Issue 12, pp. 2264-2273 (2006).

Lipson et al., "Identification of new ALK and RET gene fusions from colorectal and lung cancer biopsies" Nat Med. ; 18(3): 382-384 (2012).

Mazieres et al., "Lung Cancer That Harbors an HER2 Mutation: Epidemiologic Characteristics and Therapeutic Perspectives" vol. 31, No. 16 pp. 1997-2004 (2013).

Ploeg et al., "The present and future burden of urinary bladder cancer in the world" World J Urol vol. 27 pp. 289-293 (2009).

Ross et al., "A High Frequency of Activating Extracellular Domain ERBB2 (HER2) Mutation in Micropapillary Urothelial Carcinoma" Clin. Cancer Res. vol. 20(1), pp. 68-75 (2014) Published online Nov. 5, 2013.

Ross et al., Relapsed Classic E-Cadherin (CDH1)—Mutated Invasive Lobular Breast Cancer Shows a High Frequency of HER2 (ERBB2) Gene Mutations, Clin Cancer Res, vol. 19(1), pp. 2668-2676 (2013).

Stewart et al., "Cancer Mortality Surveillance United States—1990-2000" Surveillance Summaries, 53 (SS03);1-108 pp. 1-116 (2004). Http://www.cdc.gov/mmwr/preview/mmwrhtml/ss5303a1.htm (downloaded Jul. 10, 2014).

Tsai et al., "Clinical Significance of ErbB Receptor Family in Urothelial Carcinoma of the Bladder: A Systematic Review and Meta-Analysis" Advances in Urology, Article ID 181964, pp. 1-11 (2012).

Coogan et al. "HER-2/NEU Protein Overexpression and Gene Amplification in Human Transitional Cell Carcinoma of the Bladder" Urology (2004) vol. 63, No. 4, pp. 786-790.

Extended European Search Report for European Application No. EP 14 82 6369 dated Jan. 26, 2017.

Latif et al., "HER2/neu gene amplification and protein overexpression in G3 pT2 transitional cell carcinoma of the bladder: a role for anti-HER2 therapy?" European Journal of Cancer (2004) vol. 40, pp. 56-63.

Shigematsu et al. "A case of HER-2-positive advanced inflammatory breast cancer with invasive micropapillary component shpwing a clinically complete response to concurrent trastuzumab and paclitaxel treatment" Int J Clin Oncol (2010) vol. 15, pp. 615-620.

* cited by examiner

Table 1. Clinical Features and Genomic Alterations Identified in 15 MUPC cases

| Study # | Gender | Age at Time Sample was Obtained | Specimen Sequenced | Tumor Type | Tumor Grade | Tumor Stage | Coverage Depth | Genomic Alterations | Actionable Alterations | AKT1 | AKT2 | ARID1A |
|---|---|---|---|---|---|---|---|---|---|---|---|---|
| 1 | F | 71 | Metastasis | MPUC | HG | IV | 1525 | 3 | 2 | | | |
| 2 | M | 63 | TURBT | MPUC | HG | IV | 863 | 7 | 4 | | | |
| 3 | M | 67 | Metastasis | MPUC* | HG | IV | 675 | 4 | 3 | | | V661fs*15 |
| 4 | F | 57 | Cystectomy | MPUC | HG | IV | 753 | 8 | 3 | | | |
| 5 | F | 71 | Metastasis | MPUC | HG | IV | 757 | 5 | 3 | | | S1356fs*101 |
| 6 | M | 66 | TURBT | MPUC | HG | III | 1305 | 6 | 3 | E17K | | |
| 7 | M | 55 | TURBT | MPUC | HG | I | 904 | 1 | 1 | | | |
| 8 | F | 61 | Cystectomy | MPUC | HG | III | 999 | 3 | 1 | | | |
| 9 | M | 55 | Cystectomy | MPUC | HG | III | 1022 | 5 | 2 | | | E1767* |
| 10 | M | 73 | Cystectomy | MPUC | HG | III | 1100 | 3 | 1 | | | |
| 11 | M | 86 | Cystectomy | MPUC | HG | IV | 870 | 3 | 1 | | | |
| 12 | M | 68 | TURBT | MPUC | HG | I | 1082 | 6 | 4 | | E17K | Y215*,Q1473* |
| 13 | M | 68 | TURBT | MPUC | HG | II | 999 | 6 | 3 | | | |
| 14 | F | 63 | Metastasis | MPUC | HG | IV | 1022 | 2 | 1 | | | |
| 15 | M | 67 | TURBT | MPUC | HG | I | 793 | 5 | 4 | | | |

Fig. 2A

| Study # | AURKA | BAP1 | CCND1 | CCND3 | CCNE1 | EGFR | EPHA3 | ERBB2 | FBXW7 | HRAS | IDH2 |
|---|---|---|---|---|---|---|---|---|---|---|---|
| 1 | | | | | | | | S310F | G423V | | |
| 2 | | | Amplification | | | | Amplification | S310F | | | |
| 3 | | Homozygous Loss | | | | | | S310Y | | | |
| 4 | | | | Amplification | | | | | | | |
| 5 | | | | | Amplification | | | | | | |
| 6 | | | | | | | | | | | |
| 7 | | | | | | | | R157W | | | |
| 8 | | | | | | | | | | | |
| 9 | | | Amplification | | | | | S310F | | | |
| 10 | | | Amplification | | | | | | | G12D | |
| 11 | | | | | | | | | | | R140Q |
| 12 | | | | | | | | | | | |
| 13 | S361* | | | | | | | | | | |
| 14 | | | | | | Amplification | | | | | |
| 15 | | | | | | Amplification | | S310F | | | |

Fig. 2B

| Study # | IRS2 | JAK2 | KRAS | MCL1 | MDM2 | MLL2 | MSH2 | MYCL1 | NF2 | PTCH1 | PIK3CA | PIK3R1 |
|---|---|---|---|---|---|---|---|---|---|---|---|---|
| 1 | | | | | | | | | | | | |
| 2 | | | | Amplification | | | S612* | Amplification | | | | |
| 3 | | | | Amplification | | | | | | | | |
| 4 | | | | Amplification | | Truncation exon 48 | | | | | | |
| 5 | | | | Amplification | | M1417fs*15 | | | | | | |
| 6 | | | | | | | | | | | E542K | I290fs*4 |
| 7 | | | | | | | | | | | | |
| 8 | | | | | | | | | E463K | | | |
| 9 | | | | | | | | | | | | |
| 10 | | | | | | | | | | | | |
| 11 | Amplification | | | | | | | | | | | |
| 12 | | | G12V,G12C | | | | | | | | | |
| 13 | | Amplification | | Amplification | | | | | | | | |
| 14 | | | | | | | | Amplification | | | | |
| 15 | | | | Amplification | Amplification | | | | | V1081M | | |

Fig. 2C

| Study # | PTEN | RAF1 | RB1 |
|---|---|---|---|
| 1 | | | |
| 2 | Q298* | | |
| 3 | | | |
| 4 | | | G617*fs36 |
| 5 | | | |
| 6 | | | S397* |
| 7 | | | Y239* |
| 8 | | Amplification | Q762* |
| 9 | | | |
| 10 | | | |
| 11 | | | |
| 12 | | | |
| 13 | | | |
| 14 | | | Q344* |
| 15 | | | |

Fig. 2D

| Sample | Histology | Sample Type | Coverage | Known Short Variants | Likely Short Variants |
|---|---|---|---|---|---|
| N1 | non-MP UC | TURBT | 545 | FGFR1_c.422C>G_p.T141R (0.52,660) | MLL2:NM_003482:c.15597_15612de lGGCAGTGGCACTATGA_p.H5200fs* 38(0.29,664), TP53:NM_000546:c.559+1C>A_p. splice(0.41,530) |
| N2 | non-MP UC | TURBT | 736 | AKT1_c.49G>A_p.E17K (0.74,504), RB1_c.184C>T_p.Q62* (0.82,1043), TP53_c.742C>T_p.R248W (0.81,678) | KDM6A:NM_021140:c.3209+ 1G>A_p.splice(0.85,665) |
| N3 | non-MP UC | TURBT | 1704 | ARID1A_c.6139G>T_p.E204 7*(0.28,2875) | ERBB3_c.273G>A_p.M91I(0.26,2760) |
| N4 | non-MP UC | Cystecomy | 1236 | BRAF_c.1803A>C_p.K601N (0.08,2221), RB1_c.585G>A_p.W195* (0.34,1373), TP53_c.538G>A_p.E180K (0.16,1260) | NF1:NM_001042492:c.3986C>G_p.S 1329*(0.28,1473), NF1:NM_001042492:c.5755G>T_p.E 1919*(0.22,1968), NF1:NM_001042492:c.4076_4077ins C_p.Q1360fs*20(0.28,1507), NF2:NM_000268:c.516+1G>A_p. splice(0.08,1035) |

Fig. 4A

| Sample | Known CNAs | Known Rearrangements | Likely Rearrangements |
|---|---|---|---|
| N1 | CCND1_amplification(9,exons 5 of 5), CDKN2A_loss(0,exons 5 of 5), CDKN2B_loss(0,exons 5 of 5), ERBB2_amplification(20,exons 27 of 27), FGF19_amplification(9,exons 3 of 3), FGF3_amplification(9,exons 3of 3), FGF4_amplification(9,exons 3 of 3), RAF1_amplification(16,exons 16 of 16) | | |
| N2 | RICTOR_amplification(12,exons 39 of 39) | | |
| N3 | CCND3_amplification(8,exons 5 of 5), CDK4_amplification(16,exons 7 of 7), MDM2_amplification(16,exons 11 of 11), MYCL1_amplification(7,exons 5 of 5) | | |
| N4 | EPHA3_amplification(7,exons 17 of 17) | | |

Fig. 4B

| | | | | |
|---|---|---|---|---|
| N5 | non-MP UC | TURBT | 1333x | JAK1_c.1978G>C,p.D660H (0.4, 1443) | BAP1:NM_004656:c.1527_1527delC_p.P510fs*61(0.82,671), KDM6A:NM_021140:c.3209_3209del AGTAAGTCATTTTAATGTCCA CCT_p.N1070fs*13(0.66,793), TP53:NM_0005 46:c.560-1C>T_p.splice(0.81,832), TP53:NM_000546:c.4_14delTGCGG CTCCTC_p.E2fs*4(0.74,785) |
| N6 | non-MP UC | Cystecomy | 1367 | | KDM6A:NM_021140:c.3434 1G>A_p.splice(0.43,827), TP53:NM_000546:c.137_137delG_p. P47fs*76(0.35,1163) |
| N7 | non-MP UC | Metastasis | 1436 | PIK3CA:NM_006218:c.3140 A>G_p.H1047R(0.1,1019), TP53:NM_000546:C.839G>C _p.R280T(0.35,2656) | |
| N8 | non-MP UC | TURBT | 1059 | FGFR3:NM_000142:c742C> T_p.R248C(0.28,720) | KDM6A:NM_021140:c.3851C>G_p. S1284*(0.69,738), TSC1:NM_000368:c.2241_2241delC_ p.Q748fs*25(0.57,401) |

Fig. 4C

| | | | |
|---|---|---|---|
| N5 | CDKN2A_loss(0,exons 6 of 6),<br>CDKN2B_loss(0,exons 4 of 4),<br>MCL1_amplification(12,exons 5 of 5) | | |
| N6 | CDKN2A_loss(0,exons 6 of 6),<br>CDKN2B_loss(0,exons 4 of 4) | | |
| N7 | CCND1_amplification(12,exons 5 of 5) | FGFR3_TACC3_<br>fusion_25 | |
| N8 | CDKN2A_loss(0,exons 6 of 6),<br>CDKN2B_loss(0,exons 4 of 4),<br>MDM2_amplification(32,exons 11 of 11)<br>PIK3CA_amplification(28,exons 20 of 20) | | |

Fig. 4D

| ID | Type | Procedure | # | Mutations | Additional Mutations |
|---|---|---|---|---|---|
| N9 | non-MP UC | Cystecomy | 1287 | FGFR3:NM_000142:c.746C>G_p.S249C(0.09,520) | KDM6A:NM_021140:c.4176+1G>T_p.splice(0.13,366), PTPRD:NM_002839:c.5533_5534ins GGTAAGTTAGTTACAGTTCAAG AAT_p.S1845fs*2(0.48,1225), CDH1:NM_004360:c719_719delA_p.N240fs*10(0.05,1571), NOTCH1:NM_017617:c.3644_3650del CCCCAGACCTGAGGCCTCGTCT TCCGGGACGGACACGCGGCACG GCAGGGCCGGGGTGTGGCGGGC TTGGGCCACTGACGAAACCTGG CCCCGCAGGTGTGCA_p.G1215fs* 228(0.05,270) |
| N10 | non-MP UC | Cystecomy | 947 | PIK3CA:NM_006218:c.1624 G>A_p.E542K(0.33,1057), TP53:NM_000546:c.380C>T _p.S127F(0.23,686), TP53:NM_000546:c.313G>A _p.G105S(0.2,827) | KDM6A:NM_021140:c.2935_2938 delTTAG_p.L979fs*19(0.37, 494) |
| N11 | non-MP UC | Malignant Effusion | 1497 | TP53:NM_000546:c.637C>T _p.R213*(0.83,2379) | |
| N12 | non-MP UC | Cystecomy | 1046 | | |
| N13 | non-MP UC | TURBT | 849 | | |
| N14 | non-MP UC | Metastasis | 1465 | TP53:NM_000546:c.853G>A _p.E285K(0.52,1226), TP53:NM_000546:c.517G>A _p.V173M(0.01,1788) | KDM6A:NM_021140:c.1575_1582del TGGGCCAA_p.G526fs*2(0.5,643) |
| N15 | non-MP UC | Metastasis | 646 | | KDM6A:NM_021140:c.866_866del T_p.F289fs*36(0.19,371) |

Fig. 4E

| | | | | | |
|---|---|---|---|---|---|
| | | | | | |
| | | AKT2_amplification(24,exons 13 of 13), CCND1_amplification(13,exons 5 of 5) | CCND1_amplification(10,exons 4 of 5) | PTEN_loss(0,exons 9 of 9), MYC_amplification(7,exons 3 of 3), AKT1_amplification(7,exons 13 of 13), RPTOR_amplification(7,exons 34 of 34) | |
| N9 | N10 | N11 | N12  N13 | N14 | N15 |

Fig. 4F

| | | | | |
|---|---|---|---|---|
| N16 | non-MP UC | TURBT | 1447 | CDKN2A:NM_000077:c.238 C>T_p.R80*(0.48,1655), PIK3CA:NM_006218:c.1633 G>A_p.E545K(0.12,918), TP53:NM_000546:c.743G>A p.R248Q(0.24,2344) | LRP1B:NM_018557:C.13783A>T_p. R4595*(0.22,571), TP53:NM_000546:c.1123C>T_p. Q37.5*(0.24,2275) |
| N17 | non-MP UC | TURBT | 1199 | BRAF:NM_004333:c.1397 G>T_p.G466V(0.32,1804), HRAS:NM_005343:c.182A> G_p.Q61R(0.38,924) | |
| N18 | non-MP UC | TURBT | 1524 | | |
| N19 | non-MP UC | TURBT | 1243 | PIK3CA:NM_006218:c.1633 G>A_p.E545K(0.04,1279), PIK3CA:NM_006218:c.3145 G>A_p.G1049S(0.12,1071), TP53:NM_000546:c.736A>G _p.M246V(0.23,1367) | BRCA1:NM_007294:c.4676- 1G>C_p.splice(0.12,1400), RB1:NM_000321:c.138- 2A>G_p.splice(0.16,1000) |
| N20 | non-MP UC | TURBT | 1122 | | |
| N21 | non-MP UC | TURBT | 636 | | |

Fig. 4G

| | | | | | |
|---|---|---|---|---|---|
| N16 | | | | | |
| N17 | CDKN2A_loss(0,exons 6 of 6), CDKN2B_loss(0,exons 4 of 4) | | | | |
| N18 | CCND1_amplification(30,exons 5 of 5), EPHB1_amplification(7,exons 16 of 16), KRAS_amplification(36,exons 5 of 5), MDM2_amplification(36,exons 11 of 11), MYC_amplification(24,exons 5 of 5), PIK3CA_amplification(11,exons 20 of 20) | | | | |
| N19 | | | | | |
| N20 | | | | | |
| N21 | | | | | FGFR3_JAKMIP1_rearrangement_65 |

Fig. 4H

| | | | | |
|---|---|---|---|---|
| N22 | non-MP UC | Cystecomy | 1317 | TP53:NM_000546:c.743G>A_p.R248Q(0.36,973) | TSC1:NM_000368:c.107-1G>C_p.splice(0.44,1517) |
| N23 | non-MP UC | Cystecomy | 286 | TP53:NM_000546:c.711G>T_p.M237I(0.22,298), TP53:NM_000546:c.682G>C_p.D228H(0.13,213) | ARID1A:NM_006015:c.4536_4546C AGAGCACGGGCT>TG_p.Q1512fs*16(0.12,216) |
| N24 | non-MP UC | Metastasis | 653 | NCOR1:NM_006311:c.6899 C>G_p.S2300*(0.11,663) | ARID1A:NM_006015:c.1435C>T_p. Q479*(0.06,693), KDM6A:NM_021140:c.2029C>T_p. Q677*(0.16,432), MLL2:NM_003482:c.177-1delTGGGGTTGCTGGGGCCTGG CGTGGTACTGATGCTTGTGTGTC CACAG_p.splice(0.23,554), TSC1:NM_000368:C.2698C>Tp.Q90 0*(0.09,778) |
| N25 | non-MP UC | TURBT | 964 | TP53:NM_000546:c.844C>T_p.R282W(0.83,655) | MLL2:NM_003482:c.9105_9105delC _p.H3037fs*34(0.41,1243), RB1:NM_000321:c.1996_1996delT _p.C666fs*11(0.87,455) |

Fig. 4I

| | | | |
|---|---|---|---|
| N22 | CCND1_amplification(12,exons 5 of 5), CCND2_amplification(17,exons 5 of 5), EMSY_amplification(9,exons 20 of 20), FGF19_amplification(10,exons 3 of 3), FGF23_amplification(13,exons 3 of 3), FGF3_amplification(12,exons 3 of 3), FGF4_amplification(10,exons 3 of 3), FGF6_amplification(13,exons 3 of 3) | | |
| N23 | NRAS_amplification(16,exons 5 of 5) | | |
| N24 | CDK4_amplification(6,exons 7 of 7), MCL1_amplification(7,exons 5 of 5), MDM2_amplification(9,exons 11 of 11) | | |
| N25 | | | |

Fig. 4J

| N26 | non-MP UC | TURBT | 539 | PIK3CA:NM_006218:c.333G>C_p.K111N(0.07,657), TP53:NM_000546:c.853G>A_p.E285K(0.39,564) | RB1:NM_000321:c.277C>T_p.Q93*(0.34,573), RB1:NM_000321:c.709G>T_p.E237*(0.39,656), TP53:NM_000546:c.779_779delC_p.S261fs*84(0.48,25) |
|---|---|---|---|---|---|
| N27 | non-MP UC | Metastasis | 803 | | RB1:NM_000321:c.2206C>T_p.Q736*(0.17,605) |
| N28 | non-MP UC | Metastasis | 853 | | TSC1:NM_000368:c.234_256delATATGTGGGCAAAGCCGCACTC_p.Y79fs*20(0.39,587) |
| N29 | non-MP UC | Cystecomy | 907 | FGFR3:NM_000142:c.746C>G_p.S249C(0.15,509) | |
| N30 | non-MP UC | Metastasis | 845 | CDKN2A:NM_000077:c.44G>A_p.W15*(0.32,476), TP53:NM_000546:c.853G>A_p.E285K(0.28,705) | PIK3CA:NM_006218:c.2176G>A_p.E726K(0.17,918), KDM6A:NM_021140:c.1745C>G_p.S582*(0.15,1301), MLL2:NM_003482:c.6838G>T_p.E2280*(0.19,722) |
| N31 | non-MP UC | Metastasis | 917 | FGFR3:NM_000142:c.742C>T_p.R248C(0.43,930) | |
| N32 | | Cystecomy | 662 | | |

Fig. 4K

| | | |
|---|---|---|
| N26 | MCL1_amplification(9,exons 5 of 5), REL_amplification(9,exons 11 of 11) | |
| N27 | | FGFR3_TNIP2_rearrangement_136 |
| N28 | CDKN2A_loss(0,exons 5 of 5), CDKN2B_loss(0,exons 5 of 5) | |
| N29 | CCND1_amplification(8,exons 5 of 5), FGF19_amplification(8,exons 3 of 3), FGF3_amplification(8,exons 3 of 3), FGF4_amplification(8,exons 3 of 3) | |
| N30 | MYC_amplification(7,exons 5 of 5), RICTOR_amplification(9,exons 39 of 39) | |
| N31 | CDKN2A_loss(0,exons 5 of 5), CDKN2B_loss(0,exons 5 of 5), PTEN_loss(0,exons 9 of 9) | |
| N32 | | |

Fig. 4L

| N33 | non-MP UC | Cystecomy | 783 | | TP53:NM_000546:c.584_585TC>AA_p.I195K(0.32,682), ATRX:NM_000489:c.3105_3106insT_p.K1036fs*1(0.23,911), CREBBP:NM_004380:c.4078C>T_p.R1360*(0.25,618), KDM6A:NM_021140:c.616G>T_p.E206*(0.22,768) |
|---|---|---|---|---|---|
| N34 | non-MP UC | Cystecomy | 1538 | CDKN2A:NM_000077:c.173G>A_p.R58Q(0.08,1390), MLL2:NM_003482:c.11962C>T_p.Q3988*(0.03,2447), PIK3CA:NM_006218:c.1624G>A_p.E542K(0.22,977), TP53:NM_000546:c.853G>A_p.E285K(0.04,1851), TP53:NM_000546:c.524G>A_p.R175H(0.32,1755) | ARID1A:NM_006015:c.31_56delAGCAGCCTGGGCAACCCGCCGCCG_CC_p.S11fs*91(0.15,422), KDM6A:NM_021140:c.1663C>T_p.Q555*(0.18,1192), RB1:NM_000321:c.1953T>A_p.Y651*(0.17,1321), RB1:NM_000321:c.2513C>G_p.S838*(0.19,948), SMAD4:NM_005359:c.787+1delGTATGTACATACTTTAAAAATCTTTTAAATAGTTGAGAAAAAAGTAGGCAGCCTTTATAAAGCAAATTAACCCATGTGGGCCTTAATTTTTAG_p.splice(0.25,1747) |
| N35 | non-MP UC | TURBT | 618 | TP53:NM_000546:c.880G>T_p.E294*(0.74,714) | RB1:NM_000321:c.1510C>T_p.Q504*(0.8,581) |
| N36 | non-MP UC | Cystecomy | 801 | ERBB2:NM_004448:c.929C>T_p.S310F(0.07,753) | ARID1A:NM_006015:c.2504_2505insG_p.A837fs*35(0.12,730), NF2:NM_000268:c.997C>T_p.Q333*(0.13,70), TP53:NM_000546:c.560-1G>C_p.splice(0.11,698) |

Fig. 4M

| | | | |
|---|---|---|---|
| | | | CREBBP_SETD1A_truncation_25 |
| EGFR_amplification(36,exons 30 of 30), MYC_amplification(10,exons 5 of 5) | MLC1_amplification(11,exons 5 of 5) | | MYCL1_amplification(14,exons 5 of 5), NFKBIA_amplification(7,exons 6 of 6) |
| N33 | N34 | N35 | N36 |

Fig. 4N

| | | | | |
|---|---|---|---|---|
| N37 | non-MP UC | Cystecomy | 1329 | HRAS:NM_005343:c.181C>A_p.Q61K(0.28,1566), NFE2L2:NM_001145412:c.44G>_p.G15A(0.32,1496), PIK3CA:NM_006218:c.3062A>G_p.Y1021C(0.27, 1902), SETD2:NM_014159:c.4885C>T_p.H1629Y(0.16,1389) | ASXL1:NM_015338:c.1500_1500del C_p.S501fs*205(0.15,962), MEN1:NM_130801:c.461-1G>A_p.splice(0.19,924), MLL2:NM_003482:c.8959_8959delC _p.C2988fs*16(0.14,1091), MLL2:NM_003482:c.8676_8677insG C_p.T2893fs*1B(0.15,1068) |
| N38 | non-MP UC | Cystecomy | 754 | MLL2:NM_003482:c.3190_3191insG_p.V1064fs*4 (0.33,690), NOTCH1:NM_017617:c.868C>T_p.Q290*(0.08,297) | MLL2:NM_003482:c.7463C>A_p.S2488*(0.24,517) TP53:NM_000546:c.532_533insC_p.H178fs*3(0.44,445) |
| N39 | non-MP UC | Cystecomy | 1043 | TP53:NM_000546:c.772G>A_p.E258K(0.12,787) | KDM6A:NM_021140:c.4003G>T_p.E1335*(0.1,1099), KDM6A:NM_021140:c.1875_1876insTGCT_p.S626fs*2(0.1,1216) |
| N40 | non-MP UC | Metastasis | 1271 | MLL2:NM_003482:c.16294C>T_p.R5432W(0.02,1690), RB1:NM_000321:c.2053C>T_p.Q685*(0.6,1658), TP53:NM_000546:c.694_695AT>GC_p.I232A(0.46,1016) | MLL2:NM_003482:c.11701C>T_p.Q3901*(0.31,1383), MLL2:NM_003482:c.7411C>T_p.R2471*(0.29,1519) |
| N41 | non-MP UC | Cystecomy | 1085 | ARID1A:NM_006015:c.3634C>T_p.Q1212*(0.02, 1117), FBXW7:NM_033632:c.575A>C_p.E192A(0.5,1114) | ARID1A:NM_006015:c.4000c>T_p.Q1334*(0.1,977) |

Fig. 4O

| | | | | |
|---|---|---|---|---|
| N37 | CDKN2A_loss(0,exons 5 of 5), CDKN2B_loss(0,exons 5 of 5) | | | |
| N38 | CDKN2A_loss(0,exons 5 of 5), CDKN2B_loss(0,exons 5 of 5), EGFR_amplification(40,exons 30 of 30), MCL1_amplification(8,exons 5 of 5) | | | |
| N39 | ERBB2_amplification(15,exons 27 of 27) | | | |
| N40 | MYC_amplification(13,exons 5 of 5), MYST3_amplification(6,exons 16 of 16), RAF1_amplification(8,exons 16 of 16) | | FGFR1_intergenic Region_truncation_ 100, GATA3_VPS13B_ truncation_148 | |
| N41 | | | ERBB2_GRB7_ fusion_10 | |

Fig. 4P

| N42 | non-MP UC | Cystecomy | 863 | ERBB2:NM_004448:c.929C>T_p.S310F(0.36,955), PTEN:NM_000314:c.892C>T_p.Q298*(0.44,441) | MSH2:NM_000251:c.1835C>G_p.S612*(0.15,1387), TP53:NM_000546:c.880_881insGA_p.E294fs*52(0.4,609) |
| --- | --- | --- | --- | --- | --- |
| N43 | non-MP UC | Cystecomy | 797 | PIK3C2G:NM_004570:c.881T>C_p.I294T(0.43,509) | CREBBP:NM_004380:c.4134-1G>A_p.splice(0.31,899), TP53:NM_000546:c.375+1G>C_p.splice(0.45,499) |
| N44 | non-MP UC | Cystecomy | 1182 | ARID1A:NM_006015:C.4750C>T_p.Q1584*(0.64,1038), ARID1A:NM_006015:C.5047G>C_p.E1683Q(0.02,1131), FGFR3:NM_000142:c.746C>G_p.S249C(0.81,3390), SMAD4:NM_005359:c.431C>G_p.S144*(0.51,776) | TSC1:NM_000368:c.1030-1G>A_p.splice(0.66,1043) |
| N45 | non-MP UC | TURBT | 1002 | CREBBP:NM_004380:c.4021C>T_p.R1341*(0.14,949), NF2:NM_000268:c.482_482delG_p.G161fs*13(0.16,882), PIK3CA:NM_006218:c.1357G>C_p.E453Q(0.03,1188) | |
| N46 | non-MP UC | Cystecomy | 672 | TP53:NM_000546:c.641A>G_p.H214R(0.13,635), CREBBP:NM_004380:c.5034_5036delCTC_p.S1679del(0.06,611) | RB1:NM_000321:c.1258A>T_p.K420*(0.12,643) |

Fig. 4Q

| | | | | |
|---|---|---|---|---|
| N42 | CCND1_amplification(7,exons 5 of 5),<br>EPHA3_amplification(9,exons 17 of 17),<br>FGF19_amplification(7,exons 3 of 3),<br>FGF3_amplification(7,exons 3 of 3),<br>FGF4_amplification(7,exons 3 of 3),<br>MYCL1_amplification(7,exons 5 of 5) | | | |
| N43 | CDKN2A_loss(0,exons 5 of 5),<br>CDKN2B_loss(0,exons 5 of 5),<br>KDM6A_loss(0,exons 29 of 29) | | | |
| N44 | CDKN2A_loss(0,exons 5 of 5),<br>CDKN2B_loss(0,exons 5 of 5),<br>FGFR3_amplification(11,exons 17 of 17) | | | |
| N45 | | | | |
| N46 | | | | |

Fig. 4R

| N47 | non-MP UC | Metastasis | 857 | AKT1:NM_001014431:c.1393C>_p.R465C(0.08,961), ATR:NM_001184:c.7220G>A_p.R2407H(0.39,708), CREBBP:NM_004380:c.1447C>T:p.R483*(0.37,1214), DNMT3A:NM_022552:c.2026C>T_p.R676W(0.34,704), FANCD2:NM_033084:c.3895C>T_p.R1299C(0.06,994), FGFR3:NM_000142:c.742C>T_p.R248C(0.48,1178), FGFR3:NM_000142:c.1195C>T_p.R399C(0.11,1237), PARP4:NM_006437:c.4910G>A_p.R1637H(0.03,887), PRKDC:NM_006904:c.3407G>A_p.R1136H(0.15,962), RUNX1T1:NM_001198631:c.1471G>A_p.A491T(0.08,599), TP53:NM_000546:c.817C>T_p.R273C(0.13,1169) | ARID1A:NM_006015:c.2396_2397ins G_p.Q802fs*15(0.31,655), BRCA1:NM_007294:c.4327C>T_p.R 1443*(0.4,1011), CDK12:NM_016507:c.3812_3812del G_p.G127 1fs*23(0.32,618), CREBBP:NM_004380:c.3244_3244del A_p.i1084fs*15(0.34,960), CTCF:NM_006565:c.604_605insAA_ p.T204fs*19(0.29,1142), LRP1B:NM_018557:c.13273C>T_p. Q4425*(0.4,852), MLL2:NM_003482:c.5058_5059insA_p.R1687fs*4(0.13,1149), MLL2:NM_003482:c.3699_3699delG_p.G1235fs*95(0.35,757), MLL2:NM_003482:c.2506_2507insC_p.Q836fs*3(0.1,701), MLL2:NM_003482:c.2371_2372insC_p.Q791fs*3(0.3,799), NOTCH1:NM_017617:c.7383_7383 delC_p.A2463fs*14(0.07,1229), PALB2:NM_024675:c.834_834delA_p.N280fs*8(0.25,1120), PAX5:NM_016734:c.957_957delC_p. A322fs*11(0.35,460), RAD50:NM_005732:c.2793_2794ins A_p.N934fs*10(0.28,685), NOTCH1:NM_017617:c.4723_4725d |
| N48 | non-MP UC | Cystecomy | 1152 | NRAS:NM_002524:c.182A>G_p.Q61R(0.26,1168), TP53:NM_000546:c.536A>T_p.H179L(0.25,1096) | |

Fig. 4S

| | | | | |
|---|---|---|---|---|
| N49 | non-MP UC | Cystecomy | 960 | KDM6A:NM_021140:c.3397 C>T_p.Q1133*(0.29,462), TP53:NM_000546:c.861G>C _p.E287D(0.3,926), TP53:NM_000546:c.811G>A _p.E271K(0.31,900) | SPEN:NM_015001:c.565C>T_p.R189 *(0.11,1182) |
| N50 | non-MP UC | Cystecomy | 796 | CSF1R:NM_005211:c.95T>G _p.V32G(0.48,843), NUP93:NM_014669:c.43C>T _p.Q15*(0.06,861), TP53:NM_000546:c.853G>A _p.E285K(0.19,973) | ARID1A:NM_006015:c.1543C>T_p. Q515*(0.09,858), MLL2:NM_003482:c.7195_7195delC _p.P2400fs*26(0.19,811) |
| N51 | non-MP UC | Metastasis | 787 | HRAS:NM_005343:c.182A> G_p.Q61R(0.69,942) | |
| N52 | non-MP UC | Metastasis | 1018 | KIT:NM_000222:c.2867G>A _p.R956Q(0.27,2066), MET:NM_000245:c.1829G> A_p.C610Y(0.46,2320), TP53:NM_000546:c.659A>G _p.Y220C(0.55,937) | |
| N53 | non-MP UC | TURBT | 1105 | | |

Fig. 4U

| | | | |
|---|---|---|---|
| N49 | CDKN2A_loss(0,exons 5 of 5), CDKN2B_loss(0,exons 5 of 5), FGFR1_amplification(16,exons 18 of 18), ZNF217_amplification(7,exons 4 of 4), | | |
| N50 | JAK2_amplification(16,exons 23 of 23) | | |
| N51 | CDKN2A_loss(0,exons 5 of 5), CDKN2B_loss(0,exons 5 of 5) | | |
| N52 | KIT_amplification(16,exons 21 of 21), MET_amplification(16,exons 20 of 20), PDGFRA_amplification(20,exons 22 of 22), KDR_amplification(16,exons 30 of 30) | CEBPA_intergenic_Region_truncation_11, ARID2_ITFG1_rearrangement_62 | |
| N53 | CCND1_amplification(6,exons 5 of 5), CDKN2A_loss(0,exons 5 of 5), CDKN2B_loss(0,exons 5 of 5), FGF19_amplification(6,exons 3 of 3), FGF3_amplification(6,exons 3 of 3), FGF4_amplification(6,exons 3 of 3), MDM2_amplification(9,exons 11 of 11) | | |

Fig. 4V

| N54 | non-MP UC | Cystecomy | 770 | TP53:NM_000546:c.817C>T_p.R273C(0.53,762) | MLL2:NM_00.482:c.8366+1G>T_p.splice(0.12,761), MLL2:NM_003482:c.1724_1724delA_p.P575fs*355(0.5,1062) |
|---|---|---|---|---|---|
| N55 | non-MP UC | Cystecomy | 721 | CTNNB1:NM_001904:c.134C>T_p.S45F(0.23,1074), TP53:NM_000546:c.580C>T_p.L194F(0.29,459) | |
| N56 | non-MP UC | Cystecomy | 724 | NFE2L2:NM_001145412:c.52C>G_p.R18G(0.14,931), TP53:NM_000546:c.743G>A_p.R248Q(0.14,535) | CDKN2A:NM_000077:c.297_307del GGCCGGGGCGC_p.A102fs*14 (0.24,443) |
| N57 | non-MP UC | Cystecomy | 807 | ARID2:NM_152641:c.1802G>A_p.R601Q(0.5,1126), FGFR3:NM_000142:c.746C>G_p.S249C(0.22,656), PIK3CA:NM_006218:c.1624G>A_p.E542K(0.39,649) | ARID1A:NM_006015:c.3947C>A_p.S1316*(0.14,849), TSC1:NM_000368:c.1075_1084delC CAACTTCTC_p.P359fs*78)0.32,603) |

Fig. 4W

| | |
|---|---|
| N54 | CCND1_amplification(16,exons 5 of 5),<br>CDKN2A_loss(0,exons 5 of 5),<br>CDKN2B_loss(0,exons 5 of 5),<br>FGF12_amplification(7,exons 6 of 6),<br>FGF19_amplification(16,exons 3 of 3),<br>FGF3_amplification(16,exons 3 of 3),<br>FGF4_amplification(16,exons 3 of 3),<br>JUN_amplification(7,exons 3 of 3),<br>MCL1_amplification(9,exons 5 of 5),<br>NFKBIA_amplification(8,exons 6 of 6),<br>RAF1_amplification(9,exons 16 of 16),<br>TOP1_amplification(8,exons 21 of 21) |
| N55 | MCL1_amplification(8,exons 3 of 3) |
| N56 | RICTOR_amplification(7,exons 39 of 39) |
| N57 | CDKN2A_loss(0,exons 5 of 5),<br>CDKN2B_loss(0,exons 5 of 5) |

Fig. 4X

| | | | | |
|---|---|---|---|---|
| N58 | non-MP UC | Cystecomy | 475 | CDKN2A:NM_000077:c.322G>T_p.D108Y(0.17,284), FGFR3:NM_000142:c.1949A>T_p.K650M(0.24,372), TP53:NM_000546:c.839G>A_p.R280K(0.15,474) | MLL2:NM_003482:c.10662_10663insT_p.E3555fs*1(0.09,375), MLL2:NM_003482:c.9044_9045insG_p.CV3016fs*7(0.1420) |
| N59 | non-MP UC | TURBT | 966 | CSF1R:NM_005211:c.95T>G_p.V32G(0.5,905), FANCA:NM_000135:c.480G>A_p.M160I(0.63,945) | TET2:NM_001127208:c.5824C>T_p.Q1942*(0.2,1383) EGFR:NM_005228:c.2432C>T_p.S811F(0.05,786) |
| N60 | non-MP UC | TURBT | 729 | CDKN2A:NM_000077:c.172C>T_p.R58*(0.08,385), ERBB2:NM_004448:c.929C>T_p.S310F(0.14,573) | ARID1A:NM_006015:c.6791C>G_p.S2264*(0.07,605), TP53:NM_000546:c.82_82delG_p.E28fs*16(0.08,549) |
| N61 | non-MP UC | Cystecomy | 1032 | DNMT3A:NM_022552:c.2644C>T_p.R882C(0.04,998), TP53:NM_000546:c.839G>C_p.R280T(0.7,816) | MLL2:NM_003482:c.5155G>T_p.E1719*(0.53,921), MLL2:NM_003482:c.2096_2097delCC_p.P700fs*3(0.23,1019) |
| N62 | non-MP UC | Metastasis | 906 | CDKN2A:NM_000077:c.143C>T_p.P48L(0.41,693), MLL2:NM_003482:c.13903C>T_p.Q4635*(0.26,542), TP53:NM_000546:c.991C>T_p.Q331*(0.36,811) | KDM6A:NM_021140:c.3185_3188delATAG_p.D1062fs*20(0.46,822) |
| N63 | non-MP UC | TURBT | 862 | TP53:NM_000546:c.470T>G_p.V157G(0.85,1033) | ARID1A:NM_006015:c.5856_5856delC_p.K1953fs*3(0.58,946), MSH6:NM_000179:c.1789_1790insA_p.G599fs*8(0.2,1383) |

Fig. 4Y

| N64 | non-MP UC | Metastasis | 585 | | TP53:NM_000546:c.536A>G_p.H179R(0.79,707) | KDM6A:NM_021140:c.2082_2096T GCTCTCAATCACCT>C_p.A695FS* 30(1.02,325) |

Fig. 4Y Continued

| | |
|---|---|
| N58 | MCL1_amplification(10,exons 3 of 3), |
| N59 | CCND1_amplification(16,exons 5 of 5),<br>FGF19_amplification(16,exons 3 of 3),<br>FGF3_amplification(16,exons 3 of 3),<br>FGF4_amplification(16,exons 3 of 3),<br>MDM2_amplification(16,exons 11 of 11) |
| N60 | |
| N61 | CDKN2A_loss(0,exons 5 of 5),<br>CDKN2B_loss(0,exons 5 of 5) |
| N62 | CCND1_amplification(16,exons 5 of 5),<br>CDK6_amplification(9,exons 7 of 7),<br>EGFR_amplification(32,exons 30 of 30),<br>EMSY_amplification(9,exons 20 of 20),<br>FGF19_amplification(16,exons 3 of 3),<br>FGF3_amplification(16,exons 3 of 3),<br>FGF4_amplification(16,exons 3 of 3) |
| N63 | PTEN_loss(0,exons 9 of 9) |
| N64 | CCND1_amplification(16,exons 5 of 5),<br>CDKN2A_loss(0,exons 5 of 5),<br>CDKN2B_loss(0,exons 5 of 5),<br>FGF19_amplification(16,exons 3 of 3),<br>FGF3_amplification(16,exons 3 of 3),<br>FGF4_amplification(16,exons 3 of 3),<br>FGFR1_amplification(11,exons 18 of 18),<br>TOP1_amplification(8,exons 21 of 21),<br>ZNF703_amplification(11,exons 2 of 2) |

Fig. 4Z

SEQUENCE LISTING

<160> NUMBER OF SEQ ID NOS: 2

<210> SEQ ID NO 1
<211> LENGTH: 1255
<212> TYPE: PRT
<213> ORGANISM: Homo sapiens

<400> SEQUENCE: 1

```
Met Glu Leu Ala Ala Leu Cys Arg Trp Gly Leu Leu Ala Leu Leu
1               5                   10                  15

Pro Pro Gly Ala Ala Ser Thr Gln Val Cys Thr Gly Thr Asp Met Lys
                20                  25                  30

Leu Arg Leu Pro Ala Ser Pro Glu Thr His Leu Asp Met Leu Arg His
            35                  40                  45

Leu Tyr Gln Gly Cys Gln Val Val Gln Gly Asn Leu Glu Leu Thr Tyr
        50                  55                  60

Leu Pro Thr Asn Ala Ser Leu Ser Phe Leu Gln Asp Ile Gln Glu Val
65                  70                  75                  80

Gln Gly Tyr Val Leu Ile Ala His Asn Gln Val Arg Gln Val Pro Leu
                85                  90                  95

Gln Arg Leu Arg Ile Val Arg Gly Thr Gln Leu Phe Glu Asp Asn Tyr
            100                 105                 110

Ala Leu Ala Val Leu Asp Asn Gly Asp Pro Leu Asn Asn Thr Thr Pro
        115                 120                 125

Val Thr Gly Ala Ser Pro Gly Gly Leu Arg Glu Leu Gln Leu Arg Ser
    130                 135                 140

Leu Thr Glu Ile Leu Lys Gly Gly Val Leu Ile Gln Arg Asn Pro Gln
145                 150                 155                 160

Leu Cys Tyr Gln Asp Thr Ile Leu Trp Lys Asp Ile Phe His Lys Asn
                165                 170                 175
```

-continued

```
Asn Gln Leu Ala Leu Thr Leu Ile Asp Thr Asn Arg Ser Arg Ala Cys
                180                 185                 190

His Pro Cys Ser Pro Met Cys Lys Gly Ser Arg Cys Trp Gly Glu Ser
            195                 200                 205

Ser Glu Asp Cys Gln Ser Leu Thr Arg Thr Val Cys Ala Gly Gly Cys
        210                 215                 220

Ala Arg Cys Lys Gly Pro Leu Pro Thr Asp Cys Cys His Glu Gln Cys
225                 230                 235                 240

Ala Ala Gly Cys Thr Gly Pro Lys His Ser Asp Cys Leu Ala Cys Leu
                245                 250                 255

His Phe Asn His Ser Gly Ile Cys Glu Leu His Cys Pro Ala Leu Val
            260                 265                 270

Thr Tyr Asn Thr Asp Thr Phe Glu Ser Met Pro Asn Pro Glu Gly Arg
        275                 280                 285

Tyr Thr Phe Gly Ala Ser Cys Val Thr Ala Cys Pro Tyr Asn Tyr Leu
    290                 295                 300

Ser Thr Asp Val Gly Ser Cys Thr Leu Val Cys Pro Leu His Asn Gln
305                 310                 315                 320

Glu Val Thr Ala Glu Asp Gly Thr Gln Arg Cys Glu Lys Cys Ser Lys
                325                 330                 335

Pro Cys Ala Arg Val Cys Tyr Gly Leu Gly Met Glu His Leu Arg Glu
            340                 345                 350

Val Arg Ala Val Thr Ser Ala Asn Ile Gln Glu Phe Ala Gly Cys Lys
        355                 360                 365

Lys Ile Phe Gly Ser Leu Ala Phe Leu Pro Glu Ser Phe Asp Gly Asp
    370                 375                 380

Pro Ala Ser Asn Thr Ala Pro Leu Gln Pro Glu Gln Leu Gln Val Phe
385                 390                 395                 400

Glu Thr Leu Glu Glu Ile Thr Gly Tyr Leu Tyr Ile Ser Ala Trp Pro
                405                 410                 415

Asp Ser Leu Pro Asp Leu Ser Val Phe Gln Asn Leu Gln Val Ile Arg
            420                 425                 430

Gly Arg Ile Leu His Asn Gly Ala Tyr Ser Leu Thr Leu Gln Gly Leu
        435                 440                 445

Gly Ile Ser Trp Leu Gly Leu Arg Ser Leu Arg Glu Leu Gly Ser Gly
    450                 455                 460

Leu Ala Leu Ile His His Asn Thr His Leu Cys Phe Val His Thr Val
465                 470                 475                 480

Pro Trp Asp Gln Leu Phe Arg Asn Pro His Gln Ala Leu Leu His Thr
                485                 490                 495

Ala Asn Arg Pro Glu Asp Glu Cys Val Gly Glu Gly Leu Ala Cys His
            500                 505                 510

Gln Leu Cys Ala Arg Gly His Cys Trp Gly Pro Gly Pro Thr Gln Cys
        515                 520                 525

Val Asn Cys Ser Gln Phe Leu Arg Gly Gln Glu Cys Val Glu Glu Cys
    530                 535                 540

Arg Val Leu Gln Gly Leu Pro Arg Glu Tyr Val Asn Ala Arg His Cys
545                 550                 555                 560

Leu Pro Cys His Pro Glu Cys Gln Pro Gln Asn Gly Ser Val Thr Cys
                565                 570                 575

Phe Gly Pro Glu Ala Asp Gln Cys Val Ala Cys Ala His Tyr Lys Asp
            580                 585                 590

Pro Pro Phe Cys Val Ala Arg Cys Pro Ser Gly Val Lys Pro Asp Leu
```

```
            595                 600                 605
Ser Tyr Met Pro Ile Trp Lys Phe Pro Asp Glu Glu Gly Ala Cys Gln
610                 615                 620

Pro Cys Pro Ile Asn Cys Thr His Ser Cys Val Asp Leu Asp Asp Lys
625                 630                 635                 640

Gly Cys Pro Ala Glu Gln Arg Ala Ser Pro Leu Thr Ser Ile Ile Ser
                645                 650                 655

Ala Val Val Gly Ile Leu Leu Val Val Val Leu Gly Val Val Phe Gly
                660                 665                 670

Ile Leu Ile Lys Arg Arg Gln Gln Lys Ile Arg Lys Tyr Thr Met Arg
                675                 680                 685

Arg Leu Leu Gln Glu Thr Glu Leu Val Glu Pro Leu Thr Pro Ser Gly
                690                 695                 700

Ala Met Pro Asn Gln Ala Gln Met Arg Ile Leu Lys Glu Thr Glu Leu
705                 710                 715                 720

Arg Lys Val Lys Val Leu Gly Ser Gly Ala Phe Gly Thr Val Tyr Lys
                725                 730                 735

Gly Ile Trp Ile Pro Asp Gly Glu Asn Val Lys Ile Pro Val Ala Ile
                740                 745                 750

Lys Val Leu Arg Glu Asn Thr Ser Pro Lys Ala Asn Lys Glu Ile Leu
                755                 760                 765

Asp Glu Ala Tyr Val Met Ala Gly Val Gly Ser Pro Tyr Val Ser Arg
770                 775                 780

Leu Leu Gly Ile Cys Leu Thr Ser Thr Val Gln Leu Val Thr Gln Leu
785                 790                 795                 800

Met Pro Tyr Gly Cys Leu Leu Asp His Val Arg Glu Asn Arg Gly Arg
                805                 810                 815

Leu Gly Ser Gln Asp Leu Leu Asn Trp Cys Met Gln Ile Ala Lys Gly
                820                 825                 830

Met Ser Tyr Leu Glu Asp Val Arg Leu Val His Arg Asp Leu Ala Ala
                835                 840                 845

Arg Asn Val Leu Val Lys Ser Pro Asn His Val Lys Ile Thr Asp Phe
850                 855                 860

Gly Leu Ala Arg Leu Leu Asp Ile Asp Glu Thr Glu Tyr His Ala Asp
865                 870                 875                 880

Gly Gly Lys Val Pro Ile Lys Trp Met Ala Leu Glu Ser Ile Leu Arg
                885                 890                 895

Arg Arg Phe Thr His Gln Ser Asp Val Trp Ser Tyr Gly Val Thr Val
                900                 905                 910

Trp Glu Leu Met Thr Phe Gly Ala Lys Pro Tyr Asp Gly Ile Pro Ala
                915                 920                 925

Arg Glu Ile Pro Asp Leu Leu Glu Lys Gly Glu Arg Leu Pro Gln Pro
                930                 935                 940

Pro Ile Cys Thr Ile Asp Val Tyr Met Ile Met Val Lys Cys Trp Met
945                 950                 955                 960

Ile Asp Ser Glu Cys Arg Pro Arg Phe Arg Glu Leu Val Ser Glu Phe
                965                 970                 975

Ser Arg Met Ala Arg Asp Pro Gln Arg Phe Val Val Ile Gln Asn Glu
                980                 985                 990

Asp Leu Gly Pro Ala Ser Pro Leu Asp Ser Thr Phe Tyr Arg Ser Leu
                995                 1000                1005

Leu Glu Asp Asp Asp Met Gly Asp Leu Val Asp Ala Glu Glu Tyr
        1010                1015                1020
```

```
Leu Val Pro Gln Gln Gly Phe Phe Cys Pro Asp Pro Ala Pro Gly
    1025                1030                1035

Ala Gly Gly Met Val His His Arg His Arg Ser Ser Ser Thr Arg
    1040                1045                1050

Ser Gly Gly Gly Asp Leu Thr Leu Gly Leu Glu Pro Ser Glu Glu
    1055                1060                1065

Glu Ala Pro Arg Ser Pro Leu Ala Pro Ser Glu Gly Ala Gly Ser
    1070                1075                1080

Asp Val Phe Asp Gly Asp Leu Gly Met Gly Ala Ala Lys Gly Leu
    1085                1090                1095

Gln Ser Leu Pro Thr His Asp Pro Ser Pro Leu Gln Arg Tyr Ser
    1100                1105                1110

Glu Asp Pro Thr Val Pro Leu Pro Ser Glu Thr Asp Gly Tyr Val
    1115                1120                1125

Ala Pro Leu Thr Cys Ser Pro Gln Pro Glu Tyr Val Asn Gln Pro
    1130                1135                1140

Asp Val Arg Pro Gln Pro Pro Ser Pro Arg Glu Gly Pro Leu Pro
    1145                1150                1155

Ala Ala Arg Pro Ala Gly Ala Thr Leu Glu Arg Pro Lys Thr Leu
    1160                1165                1170

Ser Pro Gly Lys Asn Gly Val Val Lys Asp Val Phe Ala Phe Gly
    1175                1180                1185

Gly Ala Val Glu Asn Pro Glu Tyr Leu Thr Pro Gln Gly Gly Ala
    1190                1195                1200

Ala Pro Gln Pro His Pro Pro Pro Ala Phe Ser Pro Ala Phe Asp
    1205                1210                1215

Asn Leu Tyr Tyr Trp Asp Gln Asp Pro Pro Glu Arg Gly Ala Pro
    1220                1225                1230

Pro Ser Thr Phe Lys Gly Thr Pro Thr Ala Glu Asn Pro Glu Tyr
    1235                1240                1245

Leu Gly Leu Asp Val Pro Val
    1250                1255

<210> SEQ ID NO 2
<211> LENGTH: 3768
<212> TYPE: DNA
<213> ORGANISM: Homo sapiens

<400> SEQUENCE: 2
atggagctgg cggccttgtg ccgctggggg ctcctcctcg ccctcttgcc ccccggagcc      60
gcgagcaccc aagtgtgcac cggcacagac atgaagctgc ggctccctgc cagtcccgag     120
acccacctgg acatgctccg ccacctctac cagggctgcc aggtggtgca gggaaacctg     180
gaactcacct acctgcccac caatgccagc ctgtccttcc tgcaggatat ccaggaggtg     240
cagggctacg tgctcatcgc tcacaaccaa gtgaggcagg tcccactgca gaggctgcgg     300
attgtgcgag gcacccagct ctttgaggac aactatgccc tggccgtgct agacaatgga     360
gacccgctga acaataccac ccctgtcaca ggggcctccc caggaggcct gcgggagctg     420
cagcttcgaa gcctcacaga gatcttgaaa ggaggggtct tgatccagcg gaaccccag      480 ctctgctacc aggacacgat tttgtggaag acatcttcc acaagaacaa ccagctggct     540
ctcacactga tagacaccaa ccgctctcgg gcctgccacc ctgttctcc gatgtgtaag     600 ggctcccgct gctggggaga gagttctgag gattgtcaga gcctgacgcg cactgtctgt     660
```

```
gccggtggct gtgcccgctg caaggggcca ctgcccactg actgctgcca tgagcagtgt   720
gctgccggct gcacgggccc caagcactct gactgcctgg cctgcctcca cttcaaccac   780
agtggcatct gtgagctgca ctgcccagcc ctggtcacct acaacacaga cacgtttgag   840
tccatgccca atcccgaggg ccggtataca ttcggcgcca gctgtgtgac tgcctgtccc   900
tacaactacc tttctacgga cgtgggatcc tgcaccctcg tctgcccct gcacaaccaa    960
gaggtgacag cagaggatgg aacacagcgg tgtgagaagt gcagcaagcc ctgtgcccga  1020
gtgtgctatg gtctgggcat ggagcacttg cgagaggtga gggcagttac cagtgccaat  1080
atccaggagt ttgctggctg caagaagatc tttgggagcc tggcatttct gccggagagc  1140
tttgatgggg acccagcctc caacactgcc ccgctccagc cagagcagct ccaagtgttt  1200
gagactctgg aagagatcac aggttaccta tacatctcag catggccgga cagcctgcct  1260
gacctcagcg tcttccagaa cctgcaagta atccggggac gaattctgca caatggcgcc  1320
tactcgctga ccctgcaagg gctgggcatc agctggctgg gctgcgctc actgagggaa   1380
ctgggcagtg gactggccct catccaccat aacacccacc tctgcttcgt gcacacggtg  1440
ccctgggacc agctctttcg gaacccgcac caagctctgc tccacactgc caaccggcca  1500
gaggacgagt gtgtgggcga gggcctggcc tgccaccagc tgtgcgcccg agggcactgc  1560
tggggtccag ggcccaccca gtgtgtcaac tgcagccagt tccttcgggg ccaggagtgc  1620
gtggaggaat gccgagtact gcaggggctc ccaggggagt atgtgaatgc caggcactgt  1680
ttgccgtgcc accctgagtg tcagccccag aatggctcag tgacctgttt tggaccggag  1740
gctgaccagt gtgtggcctg tgcccactat aaggaccctc ccttctgcgt ggcccgctgc  1800
cccagcggtg tgaaacctga cctctcctac atgcccatct ggaagtttcc agatgaggag  1860
ggcgcatgcc agccttgccc catcaactgc acccactcct gtgtggacct ggatgacaag  1920
ggctgccccg ccgagcagag agccagcccct ctgacgtcca tcatctctgc ggtggttggc  1980
attctgctgg tcgtggtctt gggggtggtc tttgggatcc tcatcaagcg acggcagcag  2040
aagatccgga gtacacgat gcggagactg ctgcaggaaa cggagctggt ggagccgctg   2100
acacctagcg gagcgatgcc caaccaggcg cagatgcgga tcctgaaaga cgcggagctg  2160
aggaaggtga aggtgcttgg atctggcgct tttggcacag tctacaaggg catctggatc  2220
cctgatgggg agaatgtgaa aattccagtg gccatcaaag tgttgaggga aaacacatcc  2280
cccaaagcca acaaagaaat cttagacgaa gcatacgtga tggctggtgt gggctcccca  2340
tatgtctccc gccttctggg catctgcctg acatccacgg tgcagctggt gacacagctt  2400
atgcccctatg gctgcctctt agaccatgtc cgggaaaacc gcggacgcct gggctcccag  2460
gacctgctga actggtgtat gcagattgcc aaggggatga gctacctgga ggatgtgcgg  2520
ctcgtacaca gggacttggc cgctcggaac gtgctggtca agagtcccaa ccatgtcaaa  2580
attacagact cgggctggcc tcggctgctg acattgacg agacagagta ccatgcagat  2640
gggggcaagg tgcccatcaa gtggatggcg ctggagtcca ttctccgccg gcggttcacc  2700
caccagagtg atgtgtggag ttatggtgtg actgtgtggg agctgatgac ttttggggcc  2760
aaaccttacg atgggatccc cagccggagg atccctgacc tgctggaaaa gggggagcgg  2820
ctgccccagc cccccatctg caccattgat gtctacatga tcatggtcaa atgttggatg  2880
attgactctg aatgtcggcc aagattccgg gagttggtgt ctgaattctc ccgcatggcc  2940
agggaccccc agcgctttgt ggtcatccag aatgaggact gggcccagc cagtcccttg  3000
gacagcacct tctaccgctc actgctggag gacgatgaca tgggggacct ggtggatgct  3060
```

-continued

```
gaggagtatc tggtacccca gcagggcttc ttctgtccag accctgcccc gggcgctggg    3120
ggcatggtcc accacaggca ccgcagctca tctaccagga gtggcggtgg ggacctgaca    3180
ctagggctgg agccctctga agaggaggcc cccaggtctc cactggcacc ctccgaaggg    3240
gctggctccg atgtatttga tggtgacctg ggaatggggg cagccaaggg gctgcaaagc    3300
ctccccacac atgaccccag ccctctacag cggtacagtg aggaccccac agtacccctg    3360
ccctctgaga ctgatggcta cgttgccccc ctgacctgca gccccagcc tgaatatgtg    3420 aaccagccag atgttcggcc ccagccccct tcgccccgag agggccctct gcctgctgcc    3480
cgacctgctg gtgccactct ggaaaggccc aagactctct ccccagggaa gaatggggtc    3540
gtcaaagacg tttttgcctt tggggggtgcc gtggagaacc ccgagtactt gacaccccag   3600
ggaggagctg cccctcagcc ccaccctcct cctgccttca gcccagcctt cgacaacctc    3660
tattactggg accaggaccc accagagcgg ggggctccac ccagcacctt caaagggaca    3720
cctacggcag agaacccaga gtacctgggt ctggacgtgc cagtgtga                3768
```

METHODS OF TREATING UROTHELIAL CARCINOMA

CROSS REFERENCE TO RELATED APPLICATIONS

This application claims the benefit of U.S. Provisional Application No. 61/847,532, filed Jul. 17, 2013, the contents of which are hereby incorporated by reference in their entirety.

SEQUENCE LISTING

In accordance with 37 CFR 1.52(e)(5), the present specification makes reference to a Sequence Listing submitted electronically in the form of an ASCII text file (entitled "F2036-705010_SL.txt" created on Aug. 26, 2014, and 16 KB in size). The entire contents of the Sequence Listing are herein incorporated by reference, with the intention that, upon publication (including issuance), this incorporated sequence listing will be inserted in the published document immediately before the claims.

BACKGROUND

Cancer of the urinary bladder remains a major cause of morbidity and mortality around the world (Kaufman D S, et al. *Lancet*. (2009) 18 374:239-49; Noon A P, et al. *Nat Rev Urol*. (2013) 10:67-8; Ploeg M, et al. *World J Urol* (2009) 27:289-93). Despite significant success of targeted anti-cancer therapy in other common solid tumors such as breast and lung cancer, patients with loco-regionally advanced and metastatic urothelial carcinoma (UC) have limited therapy options especially when chemoresistance develops to standard anti-cancer therapies (Gorin M A, et al. *Postgrad Med*. (2012) 124:28-36; Calabro F, et al. *Eur Urol*. (2009) 55(2): 348-358).

The micropapillary variant of UC (MPUC) was first described in 1994 (Amin M B, et al. *Am J Surg Pathol*. (1994) 18:1224-32). Encompassing approximately 5% of all bladder cancers, MPUC is a clinically important lesion characterized by a distinctive histology featuring small micropapillae created by clusters of 4 to 5 cells across, peripherally situated nuclei and cytoplasmic vacuoles with a strong tendency to develop intra-lymphatic permeation or simulate lymphovascular involvement due to the production of peri-tumoral stromal retraction artifacts (Amin M B, et al. (1994) supra); Sangoi A R, et al. *Am J Surg Pathol*. (2010) 34:1367-76; Kamat A M, et al. *Cancer* (2007) 110:62-7; López J I, et al. *Histopathology* (1999) 34:561-2).

The diagnosis of MPUC harbors an adverse prognosis. Five year survival after diagnosis with metastatic urothelial carcinoma is small, pointing to the need for improved pharmacologic treatment of the disease. The standard cytotoxic regimen of MPUC is methotrexate, vinblastine, doxorubicin, and cisplatin (MVAC), and it warrants improvement. It is well-accepted that the diagnosis of MPUC harbors an adverse prognosis and pathologists have strongly recommended that, even if the minority of a urinary bladder UC features a MPUC pattern, the diagnosis of MPUC is recommended to be made either outright or the tumor should be classified as UC with MPUC features (Amin M B, et al. (1994), supra; Sangoi A R, et al. (2010), supra; Kamat A M, et al. (2007), supra; López J I, et al. (1999), supra). Among the noteworthy clinicopathologic features of MPUC, is the association of metastatic disease at the time of diagnosis for a tumor with either no invasion or limited invasion of the bladder wall. This finding is similar to that observed for other micropapillary carcinomas occurring in other sites such as in the endometrium, breast and lung (del Carmen M G, et al. *Gynecol Oncol*. (2012) 127:651-61; Chen L, et al., *Int J Surg Pathol*. (2008) 16:155-63; Kamiya K, et al. *Mod Pathol*. (2008) 21:992-1001).

Given the highly aggressive nature of MPUC, the need exists for developing novel therapeutic approaches for treating micropapillary carcinomas, such as MPUC.

SUMMARY

The invention is based, at least in part, on the discovery of alterations in the extracellular domain of a HER2 protein in a urothelial carcinoma (UC) and/or a micropapillary carcinoma, e.g., micropapillary urothelial carcinoma (MPUC). For example, Applicants have identified about a 40+% prevalence of mutations of the extracellular domain of HER2 in MPUC. In embodiments, the ERBB2 mutation frequency was significantly higher in UC samples having a confirmed MPUC histology (about 40% of 15 samples analyzed), compared to a lower frequency in the non-MPUC samples (e.g., about 9% of 64 samples presenting a traditional UC histology). In other embodiments of 64 UC cases analyzed, 3/64 had a S310F mutation and 1/64 had a ERBB2-GRB7 fusion. In certain embodiments, the alteration includes a substitution of a serine residue at position 310 (S310) in HER2 by either a phenylalanine or a tyrosine residue; or a substitution of arginine at position 157 for tryptophan. Therefore, the invention provides, at least in part, methods for treating a urothelial and/or micropapillary carcinoma, including those of the urinary tract, urinary bladder, urothelial cells, as well as methods and reagents for identifying, assessing or detecting an alteration as described herein, e.g., a HER2 mutation, in a urothelial and/or micropapillary urothelial carcinoma.

Accordingly, in one aspect, the invention features, a method of treating a subject having a urothelial cancer and/or cancer comprising a histology of micropapillae, e.g., a urothelial and/or micropapillary carcinoma (e.g., a micropapillary urothelial carcinoma). The method includes administering to the subject an effective amount of an agent (e.g., a therapeutic agent) that targets and/or inhibits HER2, e.g., a HER2 gene product (e.g., a HER2 protein), thereby treating the subject.

In one embodiment, the method further includes acquiring knowledge of one or both of:
 (i) the presence (or absence) of an alteration in HER2; or
 (ii) the presence (or absence) of a micropapillary histology
in the subject, or a cancer or tumor sample from the subject.

In another embodiment, the method further includes identifying the subject, or a cancer or tumor sample from the subject, as having one or both of:
 (i) the presence (or absence) of an alteration in HER2; or
 (ii) the presence (or absence) of a micropapillary histology.

In certain embodiments, the presence of the HER2 alteration, the micropapillary histology, or both, in the subject is indicative that the subject is likely to respond to the agent.

In yet other embodiments, the agent is administered responsive to a determination of the presence of the HER2 alteration, the micropapillary histology, or both, in the subject, or the cancer or tumor sample from the subject.

In certain embodiments, the method further comprises acquiring knowledge that the urothelial and/or micropapillary carcinoma (e.g., a micropapillary urothelial carcinoma)

does not have a gene amplification and/or overexpression of HER2 or a HER2 gene product.

Cancers

In certain embodiments, the cancer or carcinoma, e.g., the micropapillary carcinoma, is chosen from a cancer or carcinoma of the urinary system (e.g., kidney, bladder, ureter, urethra and urachus), urothelial cells, breast, lung, endometrium, bile duct or thyroid. In one embodiment, carcinoma is a urothelial carcinoma (UC), e.g., a metastatic UC. In yet other embodiment, the carcinoma has a micropapillary histology and is chosen from a cancer of the urinary tract, bladder, urothelial cells or bile duct. In yet other embodiments, the carcinoma is a transitional cell carcinoma (TCC) or an urothelial cell carcinoma. In one embodiment, the carcinoma (e.g., the micropapillary carcinoma) is a micropapillary urothelial carcinoma (MPUC). It is noted that the term "micropapillary urothelial carcinoma" and its abbreviation, "MPUC" are used interchangeably herein.

In certain embodiment, the cancer has, or is identified or determined as having, a histology of micropapillae. In certain embodiments, the micropapillary histology or histology of micropapillae comprises small micropapillae created by clusters of two or more cells (typically 4 to 5 cells) across, peripherally situated nuclei and cytoplasmic vacuoles.

In other embodiments, the cancer or carcinoma, e.g., the urothelial and/or micropapillary cancer or carcinoma (e.g., the micropapillary urothelial carcinoma), comprises, or is identified or determined as having, an alteration in HER2, e.g., an alteration in HER2 as described herein. In one embodiment, the micropapillary carcinoma does not have a gene amplification or overexpression of HER2 or a HER2 gene product. For example, the cancer is not an ERBB2-amplified cancer or carcinoma (e.g., an ERBB2-amplified urothelial carcinoma). In certain embodiments, the cancer does not have, or is identified as not having, an elevated level of a HER2 gene product. In other embodiments, the cancer is, or is identified as being negative for, an overexpressed HER2 gene product (e.g., the cancer is negative for HER2 amplification or overexpression by nucleic acid or protein detection methods, e.g., PCR or immunohistochemistry).

In other embodiments, the cancer, e.g., the micropapillary carcinoma, comprises, or is identified or determined as having, an alteration in one or more of: AKT1, AKT2, CCND1, EGFR, PIK3CA, PIK3R1 or RAF1. In one embodiment, the cancer has a wild-type HER2 and comprises an alteration in one or more of: AKT1, AKT2, CCND1, EGFR, PIK3CA, PIK3R1 or RAF1. Such cancers can be treated with modulators, e.g., inhibitors, of one or more of: AKT1, AKT2, CCND1, EGFR, PIK3CA, PIK3R1 or RAF1.

In certain embodiments, the alteration in HER2 results in increased activity of a HER2 gene product (e.g., a HER2 protein), compared to a wild-type activity of HER2. For example, the alteration can result in an alteration (e.g., an increase) in one or more of: kinase activity and/or dimerization of a HER2 protein. In one embodiment, the HER2 alteration is, or comprises, a mutation (e.g., a somatic mutation), e.g., a substitution (e.g., a base substitution), a deletion or an insertion. In one embodiment, the alteration occurs in the extracellular domain of HER2, e.g., the alteration is found in domain II of HER2 (e.g., human HER2). In one embodiment, the alteration is a missense mutation. In one embodiment, the alteration is a substitution at residue 310 of HER2. In one embodiment, the alteration is, or comprises, a substitution of residue S310 to phenylanine (e.g., S310F) or tyrosine (e.g., S310Y) of HER2. In one embodiment, the alteration is, or comprises, a substitution of residue S310 to phenylanine of HER2. In another embodiment, the alteration is, or comprises, a substitution of residue S310 to tyrosine of HER2. In yet another embodiment, the alteration is, or comprises, a substitution of residue 157, e.g., a substitution of arginine at position 157 for tryptophan (e.g., R157W). In yet other embodiments, the alteration is a HER2 gene amplification event. In other embodiments, the alteration is, or comprises, an alteration in the kinase domain of HER2. In other embodiments, the alteration is, or comprises, a substitution of residue 719, e.g., a substitution of glycine at position 719 for serine (e.g., G719S). In other embodiments, the alteration is, or comprises, a substitution of residue 689, e.g., a substitution of valine at position 689 for methionine (e.g., V689M). In other embodiments, the alteration is, or comprises, a substitution of residue 700, e.g., a substitution of methionine at position 700 for aspartic acid (e.g., M700D). In other embodiments, the alteration is, or comprises, a substitution of residue 826, e.g., a substitution of asparagine at position 826 for serine (e.g., N826S). In other embodiments, the alteration is, or comprises, a substitution of residue 839, e.g., a substitution of alanine at position 839 for threonine (e.g. A839T). In other embodiments, the alteration is, or comprises, a substitution of residue 861, e.g., a substitution of leucine at position 861 for glutamine (e.g., L861Q).

Subjects

In certain embodiments, the subject has an alteration in HER2, e.g., the subject has a urothelial and/or a micropapillary carcinoma comprising a HER2 alteration described herein. In other embodiments, the subject is identified, or has been previously identified, as having a carcinoma (e.g., a urothelial and/or micropapillary carcinoma) comprising a HER2 alteration. In one embodiment, the subject does not have a gene amplification or overexpression of HER2 or a HER2 gene product. For example, the subject does not have an ERBB2-amplified cancer or carcinoma (e.g., an ERBB2-amplified urothelial carcinoma). In certain embodiments, the subject does not show an elevated level of, or is negative for, a HER2 gene product (e.g., the cancer is negative for HER2 expression by nucleic acid or protein detection methods, e.g., PCR or immunohistochemistry).

In other embodiments, the subject is identified, or has been previously identified, as having a carcinoma with a micropapillary histology, e.g., a micropapillary histology as described herein. In yet other embodiments, the subject is identified, or has been previously identified, as having a carcinoma with an alteration in HER2 (e.g., a HER2 alternation as described herein, such as a substitution at residue 310 or residue 157), and as having a carcinoma with a micropapillary histology. For example, the subject is identified, or has been previously identified, as having a micropapillary carcinoma chosen from the urinary tract, bladder, urothelial cells or bile duct. In one embodiment, the subject is identified, or has been previously identified, as having an MPUC.

In one embodiment, the subject is a human. In one embodiment, the subject has, or is at risk of having a cancer (e.g., a urothelial and/or micropapillary carcinoma (e.g., MPUC) as described herein) at any stage of disease, e.g., a metastatic cancer. In other embodiments, the subject is a cancer patient, e.g., a patient having a urothelial and/or micropapillary carcinoma as described herein.

In one embodiment, the subject is undergoing or has undergone treatment with a different (e.g., non-HER2) therapeutic agent or therapeutic modality. In one embodiment, the non-HER2 therapeutic agent or therapeutic modality is a chemotherapy, immunotherapy, or a surgical procedure. In one embodiment, the non-HER2 therapeutic agent or therapeutic modality comprises one or more (or all) of: methotrexate, vinblastine, doxorubicin, and/or cisplatin (MVAC).

In one embodiment, responsive to the determination of the presence of the HER2 alteration and/or micropapillary histology described herein, the different therapeutic agent or therapeutic modality is discontinued. In yet other embodiments, the subject has been identified as being likely or unlikely to respond to the different therapeutic agent or therapeutic modality.

In certain embodiments, the subject has participated previously in a clinical trial, e.g., a clinical trial for a different (e.g., non-HER2) therapeutic agent or therapeutic modality. In other embodiments, the subject is a cancer patient who has participated in a clinical trial, e.g., a clinical trial for a different (e.g., non-HER2) therapeutic agent or therapeutic modality.

Agents

In certain embodiments, the agent (e.g., the therapeutic agent) used in the methods targets and/or inhibits HER2 (e.g., a HER2 gene or gene product as described herein). In one embodiment, the agent binds and inhibits HER2. In one embodiment, the agent is a reversible or an irreversible HER2 inhibitor. In certain embodiments, the agent is a pan ERBB inhibitor, or a dual or a specific HER2 inhibitor. In one embodiment, the agent is a dual EGFR/ERBB2 inhibitor, e.g., a reversible or an irreversible dual EGFR/ERBB2 inhibitor.

In one embodiment, the agent is an antibody molecule, e.g., an anti-HER2 antibody molecule (e.g., a monoclonal or a bispecific antibody), or a conjugate thereof (e.g., an antibody to HER2 conjugated to a cytotoxic agent (e.g., mertansine DM1)). In one embodiment, the agent is a kinase inhibitor. In one embodiment, the kinase inhibitor is chosen from: a multi-specific kinase inhibitor, a HER2/ERBB2 inhibitor, an EGFR inhibitor (e.g., a pan ERBB inhibitor), a HER3 inhibitor, and/or a small molecule inhibitor that is selective for HER2.

In one embodiment, the agent is chosen from: a kinase inhibitor, a multi-specific kinase inhibitor; a HER2 inhibitor; an EGFR inhibitor (e.g., a pan ERBB inhibitor); a small molecule inhibitor that is selective for HER2; an antibody molecule (e.g., a monoclonal or a bispecific antibody) against HER2; an antibody to HER2 conjugated to a cytotoxic agent (e.g., mertansine DM1) and/or a HER2 cellular immunotherapy.

In one embodiment, the agent is chosen from: AV-203, AMG 888, U3-1287, APC8024, DN24-02, Neuvenge, Lapuleucel-T, MM-111, MM-121, SAR256212, MM-141, LJM716, REGN1400, MEHD7945A, RG7597, RG7116, Trastuzumab, trastuzumab emtansine (T-DM1), pertuzumab, afatinib, TAK-285, Neratinib, Dacomitinib, BMS-690514, BMS-599626, Pelitinib, CP-724714, Lapatinib, TAK-165, ARRY-380, and/or AZD8931. In one embodiment, the agent is an irreversible HER2/EGFR tyrosine kinase inhibitor, e.g., Neratinib.

In other embodiments, the agent is chosen from a nucleic acid molecule (e.g., an antisense molecule, a ribozyme, a double stranded RNA, or a triple helix molecule) that hybridizes to and/or inhibits a HER2 nucleic acid, e.g., a HER2 nucleic acid encoding the alteration, or a transcription regulatory region that blocks or reduces mRNA expression of the alteration.

Compositions, e.g., pharmaceutical compositions, comprising one or more of the agents, e.g., the therapeutic agents described herein, for use, e.g., in treating a urothelial and/or micropapillary carcinoma (e.g., MPUC) as described herein are also disclosed.

Additionally, kits comprising the agents, e.g., the therapeutic agents (and compositions thereof), with instructions for use in treating a urothelial and/or micropapillary carcinoma (e.g., MPUC) and/or determining the presence of an alteration and/or a histology described herein are also provided.

In another aspect, the invention features a kit comprising one or more detection reagents (e.g., probes, primers, antibodies), capable, e.g., of specific detection of a nucleic acid or protein comprising an alteration described herein.

The invention also provides methods of: identifying, assessing or detecting an alteration described herein, e.g., a HER2 mutation, in a urothelial and/or micropapillary carcinoma (e.g., MPUC). Included are isolated nucleic acid molecules comprising the alterations, nucleic acid constructs, host cells containing the nucleic acid molecules; purified polypeptides comprising the alteration described herein and binding agents; detection reagents (e.g., probes, primers, antibodies, kits, capable, e.g., of specific detection of a nucleic acid or protein comprising an alteration described herein); screening assays for identifying molecules that interact with, e.g., inhibit the alterations, e.g., novel kinase inhibitors or binders of HER2. In one embodiment, the detection of the alteration comprises sequencing, e.g., nucleic acid sequencing or amino acid sequencing.

Alternatively, or in combination with the methods described herein, the invention features a method of determining the presence of an alteration and/or micropapillary histology described herein in a cancer, e.g., a urothelial and/or micropapillary carcinoma (e.g., micropapillary urothelial carcinoma (MPUC)). The method includes: acquiring knowledge (e.g., directly acquiring knowledge) that the alteration described herein is present in a subject, e.g., a sample (e.g., a cancer or tumor sample) from the subject. In one embodiment, the acquiring step comprises a determination of the presence of the alteration in a nucleic acid molecule from the subject, e.g., by performing a sequencing step. In other embodiments, the acquiring step comprises a determination of the presence of a polypeptide or a protein comprising the alteration described herein in the sample from the subject. Alternatively or in combination, the method further includes determining the histology of the sample, e.g., determining if the sample has a micropapillary histology.

Additional aspects or embodiments of the invention include one or more of the following.

In one embodiment, the subject, or the sample, comprises one or more cells or tissue from a urothelial and/or micropapillary carcinoma chosen from the urinary tract, bladder, urothelial cells or bile duct. In one embodiment, the subject or sample comprises one or more cells or tissue from a urothelial or a micropapillary urothelial carcinoma.

In one embodiment the method further comprises administering an agent, e.g., a therapeutic agent that targets and/or inhibits HER2, e.g., an agent as described herein, to the subject responsive to the determination of the presence of the alteration and/or the micropapillary histology in the sample from the subject.

In one embodiment, the mutation is detected in a nucleic acid molecule or a polypeptide. The method includes detecting whether a mutated nucleic acid molecule or polypeptide is present in a cell (e.g., a circulating cell), a tissue (e.g., a tumor), or a sample, e.g., a tumor sample, from a subject. In one embodiment, the sample is a nucleic acid sample. In one embodiment, the nucleic acid sample comprises DNA, e.g., genomic DNA or cDNA, or RNA, e.g., mRNA. In other embodiments, the sample is a protein sample.

In embodiments, the method further includes determining the histology of the tissue or the sample, e.g., determining if the sample has a micropapillary histology. In one embodiment, the sample is, or has been, classified as having a micropapillary histology.

In one embodiment, the sample or tissue is, or has been, classified as non-malignant or malignant using other diagnostic techniques, e.g., immunohistochemistry. For example, the sample or tissue does not show an elevated level of, or is negative for, a HER2 gene product (e.g., the cancer is negative for HER2 expression by nucleic acid or protein detection methods, e.g., PCR or immunohistochemistry).

In one embodiment, the sample is acquired from a subject (e.g., a subject having or at risk of having a cancer, e.g., a patient), or alternatively, the method further includes acquiring a sample from the subject. The sample can be chosen from one or more of: tissue, e.g., cancerous tissue (e.g., a tissue biopsy), whole blood, serum, plasma, buccal scrape, sputum, saliva, cerebrospinal fluid, urine, stool, circulating tumor cells, circulating nucleic acids, or bone marrow. In certain embodiments, the sample is a tissue (e.g., a tumor biopsy), a circulating tumor cell or nucleic acid.

In embodiments, the tumor is from a cancer described herein, e.g., is chosen from a urothelial and/or micropapillary carcinoma, e.g., a MPUC.

In one embodiment, the subject is at risk of having, or has a urothelial and/or micropapillary carcinoma, e.g., a MPUC.

In other embodiments, the mutation is detected in a nucleic acid molecule by a method chosen from one or more of: nucleic acid hybridization assay, amplification-based assays (e.g., polymerase chain reaction (PCR)), PCR-RFLP assay, real-time PCR, sequencing, screening analysis, SSP, HPLC or mass-spectrometric genotyping.

In one embodiment, the method includes: contacting a nucleic acid sample, e.g., a genomic DNA sample (e.g., a chromosomal sample or a fractionated, enriched or otherwise pre-treated sample) or a gene product (mRNA, cDNA), obtained from the subject, with a nucleic acid fragment (e.g., a probe or primer as described herein (e.g., an exon-specific probe or primer) under conditions suitable for hybridization, and determining the presence or absence of the mutated nucleic acid molecule. The method can, optionally, include enriching a sample for the gene or gene product.

Alternatively, or in combination with the methods described herein, the invention features a method for determining the presence of a mutated nucleic acid molecule. The method includes: acquiring a sequence for a position in a nucleic acid molecule, e.g., by sequencing at least one nucleotide of the nucleic acid molecule (e.g., sequencing at least one nucleotide in the nucleic acid molecule that comprises the mutation), thereby determining that the mutation is present in the nucleic acid molecule. Optionally, the sequence acquired is compared to a reference sequence, or a wild type reference sequence. In one embodiment, the nucleic acid molecule is from a cell (e.g., a circulating cell), a tissue (e.g., a urothelial and/or micropapillary carcinoma, e.g., a MPUC), or any sample from a subject (e.g., blood or plasma sample). In other embodiments, the nucleic acid molecule from a tumor sample (e.g., a tumor or cancer sample) is sequenced. In one embodiment, the sequence is determined by a next generation sequencing method. The method further can further include acquiring, e.g., directly or indirectly acquiring, a sample, e.g., a urothelial and/or micropapillary carcinoma, e.g., a MPUC.

In another aspect, the invention features a method of analyzing a tumor or a circulating tumor cell. The method includes acquiring a nucleic acid sample from the tumor or the circulating cell; and sequencing, e.g., by a next generation sequencing method, a nucleic acid molecule, e.g., a nucleic acid molecule that includes an alteration as described herein.

In yet other embodiment, a polypeptide comprising an alteration described herein is detected. The method includes: contacting a protein sample with a reagent which specifically binds to a polypeptide comprising an alteration described herein; and detecting the formation of a complex of the polypeptide and the reagent. In one embodiment, the reagent is labeled with a detectable group to facilitate detection of the bound and unbound reagent. In one embodiment, the reagent is an antibody molecule, e.g., is selected from the group consisting of an antibody, and antibody derivative, and an antibody fragment.

In yet another embodiment, the level (e.g., expression level) or activity the polypeptide comprising an alteration described herein is evaluated. For example, the level (e.g., expression level) or activity of the polypeptide (e.g., mRNA or polypeptide) is detected and (optionally) compared to a pre-determined value, e.g., a reference value (e.g., a control sample).

In yet another embodiment, the alteration is detected prior to initiating, during, or after, a treatment in a subject having an alteration described herein.

In one embodiment, the alteration is detected at the time of diagnosis with a cancer. In other embodiment, the alteration is detected at a pre-determined interval, e.g., a first point in time and at least at a subsequent point in time.

In certain embodiments, responsive to a determination of the presence of the alteration, any of the methods described herein further include one or more of:

(1) stratifying a patient population (e.g., assigning a subject, e.g., a patient, to a group or class);

(2) identifying or selecting the subject as being likely or unlikely to respond to a treatment, e.g., a HER2 inhibitor treatment as described herein;

(3) selecting a treatment option, e.g., administering or not administering a preselected therapeutic agent, e.g., a HER2 inhibitor as described herein; or (4) prognosticating the time course of the disease in the subject (e.g., evaluating the likelihood of increased or decreased patient survival).

In certain embodiments, responsive to the determination of the presence of a mutation, the subject is classified as a candidate to receive treatment with a therapy disclosed herein. In one embodiment, responsive to the determination of the presence of a mutation, the subject, e.g., a patient, can further be assigned to a particular class if a mutation is identified in a sample of the patient. For example, a patient identified as having a mutation can be classified as a candidate to receive treatment with a therapy disclosed herein. In one embodiment, the subject, e.g., a patient, is assigned to a second class if the mutation is not present. For example, a patient who has a tumor that does not contain a mutation, may be determined as not being a candidate to receive a therapy disclosed herein.

In another embodiment, responsive to the determination of the presence of the alteration, the subject is identified as likely to respond to a treatment that comprises a therapy disclosed herein.

In yet another embodiment, responsive to the determination of the presence of the alteration, the method includes administering an agent, e.g., a therapeutic agent as described herein, e.g., a HER2 inhibitor, to the subject.

Method of Evaluating a Tumor or a Subject

In another aspect, the invention features a method of evaluating a subject (e.g., a patient), e.g., for risk of having or developing a cancer, e.g., a urothelial and/or micropapillary carcinoma, e.g., MPUC. The method includes: acquiring information or knowledge of the presence of a mutation as described herein in a subject (e.g., acquiring genotype information of the subject that identifies a mutation as being present in the subject); acquiring a sequence for a nucleic acid molecule identified herein (e.g., a nucleic acid molecule that includes a mutation sequence); or detecting the presence of a nucleic acid or polypeptide in the subject), wherein the presence of the mutation is positively correlated with increased risk for, or having, a cancer associated with such a mutation.

The method can further include acquiring, e.g., directly or indirectly, a sample from a patient and evaluating the sample for the present of an alteration and/or a micropapillary histology as described herein.

The method can further include the step(s) of identifying (e.g., evaluating, diagnosing, screening, and/or selecting) the subject as being positively correlated with increased risk for, or having, a cancer associated with the alteration.

In another embodiment, a subject identified as having the alteration and/or micropapillary histology is identified or selected as likely or unlikely to respond to a treatment, e.g., a therapy disclosed herein. The method can further include treating the subject with a therapy disclosed herein.

In a related aspect, a method of evaluating a patient or a patient population is provided. The method includes: identifying, selecting, or obtaining information or knowledge that the patient or patient population has participated in a clinical trial; acquiring information or knowledge of the presence of an alteration (e.g., an alteration as described herein) in the patient or patient population (e.g., acquiring genotype information of the subject that identifies an alteration as being present in the subject); acquiring a sequence for a nucleic acid molecule identified herein (e.g., a nucleic acid molecule that includes an alteration sequence); or detecting the presence of a mutated nucleic acid or polypeptide in the subject), wherein the presence of the alteration, alone or in combination with a micropapillary histology, identifies the patient or patient population as being likely to respond to an agent as described herein (e.g., a HER2 inhibitor).

In some embodiments, the method further includes treating the subject with an agent as described herein (e.g., a HER2 inhibitor).

Reporting

Methods described herein can include providing a report, such as, in electronic, web-based, or paper form, to the patient or to another person or entity, e.g., a caregiver, e.g., a physician, e.g., an oncologist, a hospital, clinic, third-party payor, insurance company or government office. The report can include output from the method, e.g., the identification of nucleotide values, the indication of presence or absence of an alteration and/or micropapillary histology as described herein, or wildtype sequence. In one embodiment, a report is generated, such as in paper or electronic form, which identifies the presence or absence of an alteration described herein, and optionally includes an identifier for the patient from which the sequence was obtained.

The report can also include information on the role of a mutation as described herein, or wildtype sequence, in disease. Such information can include information on prognosis, resistance, or potential or suggested therapeutic options, e.g., an agent as described herein (e.g., a HER2 inhibitor). The report can include information on the likely effectiveness of a therapeutic option, the acceptability of a therapeutic option, or the advisability of applying the therapeutic option to a patient, e.g., a patient having a sequence, alteration or mutation identified in the test, and in embodiments, identified in the report. For example, the report can include information, or a recommendation on, the administration of a drug, e.g., the administration at a preselected dosage or in a preselected treatment regimen, e.g., in combination with other drugs, to the patient. In one embodiment, not all mutations identified in the method are identified in the report. For example, the report can be limited to mutations in genes having a preselected level of correlation with the occurrence, prognosis, stage, or susceptibility of the cancer to treatment, e.g., with a preselected therapeutic option. The report can be delivered, e.g., to an entity described herein, within 7, 14, or 21 days from receipt of the sample by the entity practicing the method.

In another aspect, the invention features a method for generating a report, e.g., a personalized cancer treatment report, by obtaining a sample, e.g., a tumor sample, from a subject, detecting a mutation as described herein in the sample, and selecting a treatment based on the mutation identified. In one embodiment, a report is generated that annotates the selected treatment, or that lists, e.g., in order of preference, two or more treatment options based on the mutation identified. In another embodiment, the subject, e.g., a patient, is further administered the selected method of treatment.

Unless otherwise defined, all technical and scientific terms used herein have the same meaning as commonly understood by one of ordinary skill in the art to which this invention belongs. Although methods and materials similar or equivalent to those described herein can be used in the practice or testing the invention, suitable methods and materials are described below. All publications, patent applications, patents, and other references mentioned herein are incorporated by reference in their entirety. In case of conflict, the present specification, including definitions, will control. In addition, the materials, methods, and the example are illustrative only and not intended to be limiting.

The details of one or more embodiments featured in the invention are set forth in the accompanying drawings and the description below. Other features, objects, and advantages featured in the invention will be apparent from the description and drawings, and from the claims.

BRIEF DESCRIPTION OF THE DRAWINGS

FIGS. 2A-2D depicts a Table summarizing the clinical features and genomic alterations identified in 15 MUPC cases. The data for each case is encompassed in FIG. 2A-2D. For each study case, the clinical features of: gender (female (F) or male (M), age at the time the sample was obtained, specimen sequenced, tumor type, tumor grade, tumor stage coverage depth, genomic alterations, actionable alterations, and the genomic alterations in AKT1, AKT2, and ARID1A are summarized for each study case in FIG. 2A. For each study case, the genomic alterations in AURKA, BAP1, CCND1, CCND3, CCNE1, EGFR, EPHA3, ERBB2, FBXW, HRAS, and IDHA are summarized in FIG. 2B. For each study case, the genomic alterations in IRS2, JAK2, KRAS, MCL1, MDM2, MLL2, MSH2, MYCL1, NF2, PTCH1, PIK3CA, and PIK3R1 are summarized in FIG. 2C. For each study case, the genomic alterations in PTEN, RAF1, and RB1 are summarized in FIG. 2D.

For example, for Study Case 1, the clinical features of: gender (F), age at the time the samples was obtained (71), specimen sequenced (metastasis) tumor type (MPUC), tumor grade (HG), tumor stage (IV), coverage depth (1525), genomic alterations (3), actionable alterations (2), and the genomic alterations in AKT1 (none), AKT2 (none), and ARIDIA (none) are summarized for each study case in FIG. 2A. For each study case, the genomic alterations in AURKA (none), BAP1 (none), CCND1 (none), CCND3 (none), CCNE1 (none), EGFR (none), EPHA3 (none), ERBB2 (S310F), FBXW (G423V), HRAS (none), and IDHA (none) are summarized in FIG. 2B. For each study case, the genomic alterations in IRS2 (none), JAK2 (none), KRAS (none), MCL1 (none), MDM2 (none), MLL2 (none), MSH2 (none), MYCL1 (none), NF2 (none), PTCH1 (none), PIK3CA (none), and PIK3R1 (none) are summarized in FIG. 2C. For each study case, the genomic alterations in PTEN (none), RAF1 (none), and RB1 (none) are summarized in FIG. 2D.

Figure 3:
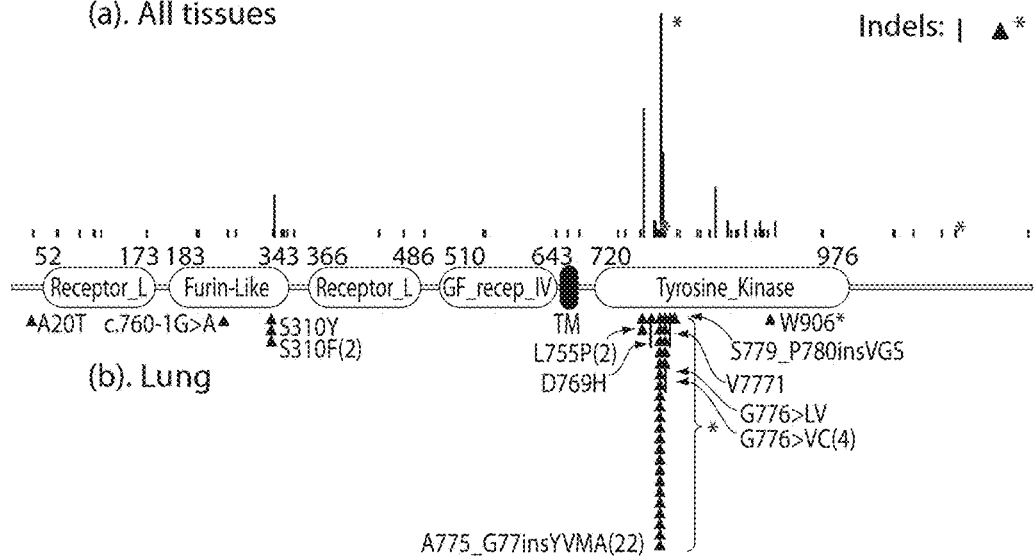
Figure 3:
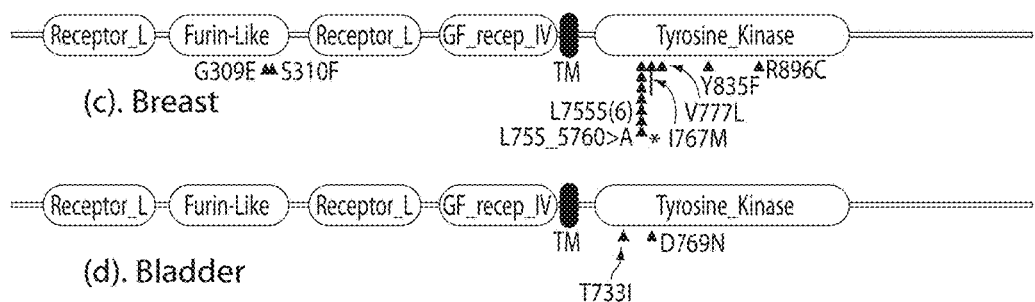
Figure 3:

FIG. 3 depicts the relative incidence of erbb2 mutations in lung cancer, breast cancer, urinary bladder cancer (all urothelial carcinomas) in the cosmic database and micropapillary urothelial carcinoma in the current study.

FIGS. 4A-4Z depicts a Table summarizing the genomic alterations in 64 cases of relapsed/metastatic non-micropapillary urothelial carcinoma of the bladder. The data for each case is encompassed in two consecutive figures. For example, the data for cases N1-N4 is encompassed in FIG. 4A-4B; the data describing the histology, sample type, known short variants, and likely short variants for cases N1-N4 is encompassed in FIG. 4A; and the data describing known CNAs, known rearrangements, and likely rearrangements for cases N1-N4 is encompassed in FIG. 4B. For further example, for study case N1 the data describing the histology (non-MPUC), sample type (TURBT), known short variants (FGFR1_c.422C>G_p.T141R(0.52,660)), and likely short variants (MLL2:NM_003482:c.15597_15612 delGGCAGTGGCACTATGA_p.H5200fs*38(0.29,664), TP53:NM_000546: c.559+1C>A_p.splice(0.41,530)) is encompassed in FIG. 4A; and the data describing known CNAs (CCND1_amplification(9,exons 5 of 5), CDKN2A_loss(0,exons 5 of 5), CDKN2B_loss(0,exons 5 of 5), ERBB2_amplification(20,exons 27 of 27), FGF19_amplification(9,exons 3 of 3), FGF3_amplification (9,exons 3 of 3), FGF4_amplification(9,exons 3 of 3), RAF1_amplification(16,exons 16 of 16)), known rearrangements (none), and likely rearrangements (none) is encompassed in FIG. 4B.

Figure 5:
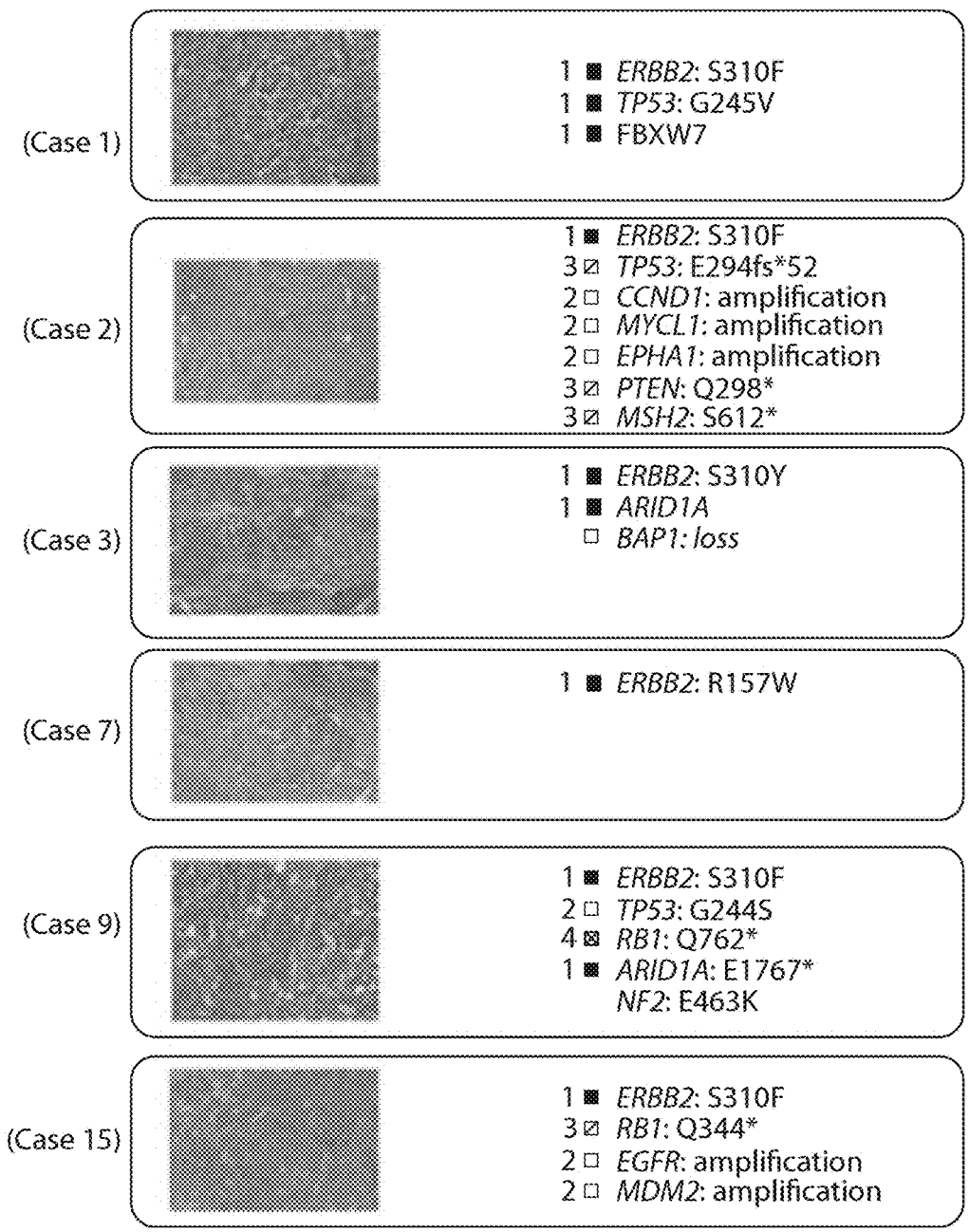

FIG. 5 depicts the Histology and List of Genomic Alterations in 6 cases of Micropapillary Urothelial Carcinoma Featuring Mutations in the ERBB2 Gene.

Figure 6:
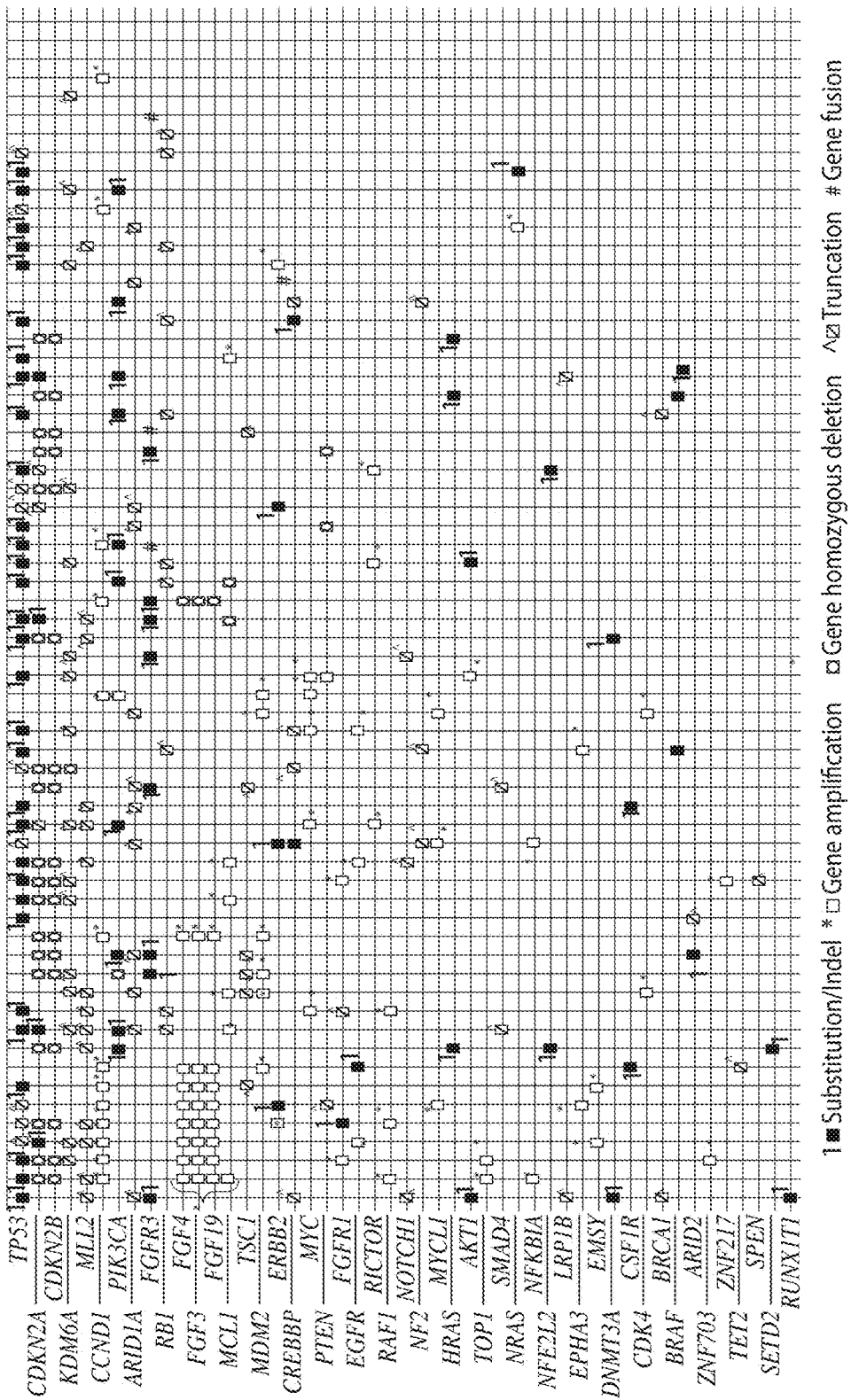
Figure 6:
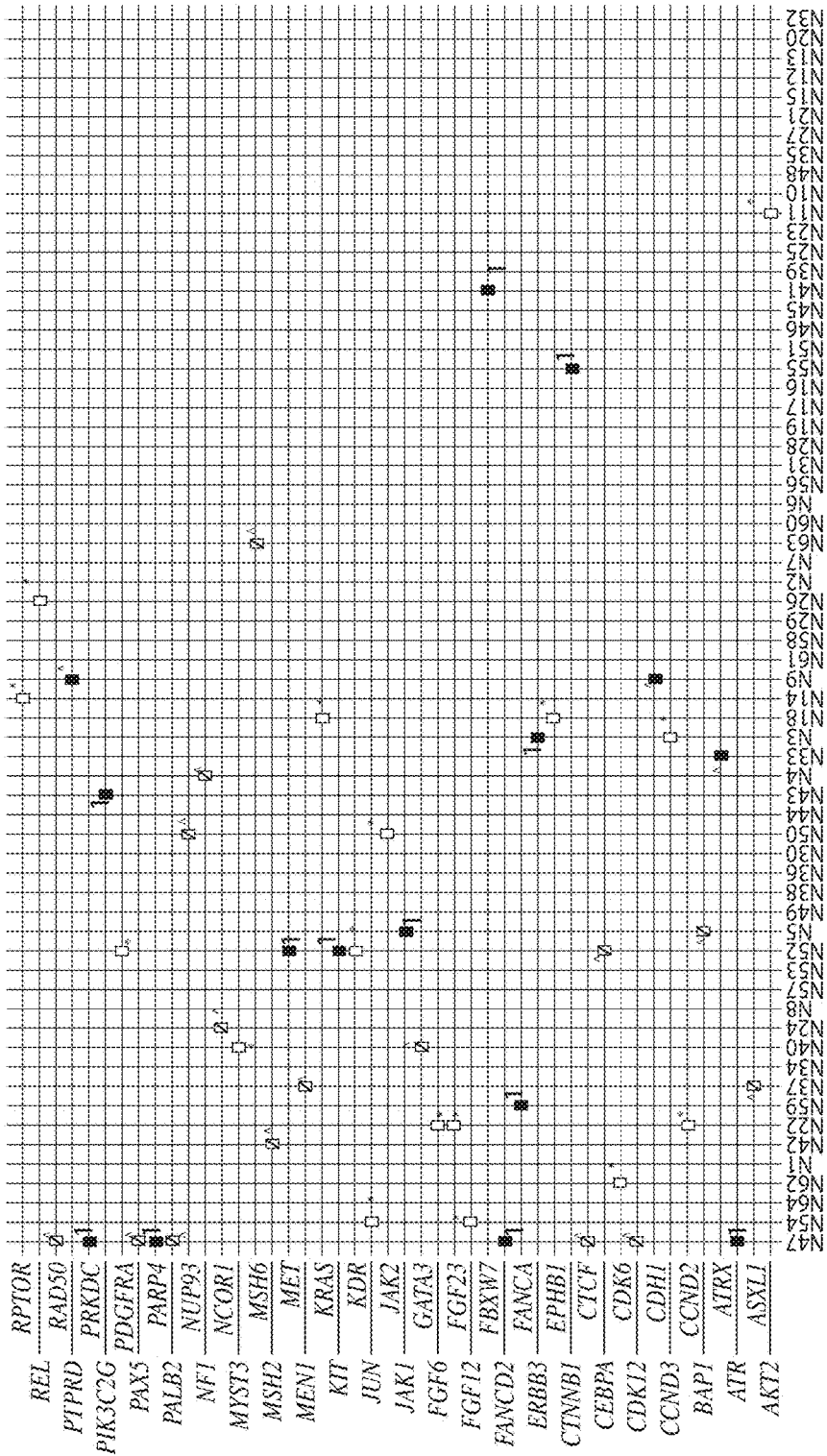

FIG. 6 depicts a tile plot of genomic alterations in cases of micropapillary urothelial carcinoma.

DETAILED DESCRIPTION

Described herein is the identification of a mutation at a Serine at position 310 to phenylalanine (S310F) in the extracellular domain of HER2 in a human with urothelial carcinoma (UC). Additionally described herein is a genomic analysis of a series of patients with micropapillary urothelial carcinoma (MPUC) and non-micropapillary urothelial bladder carcinomas (non-MPUC) to characterize the genomic landscape of MPUC. In a retrospective series of MPUC, Applicants have identified about 40+% prevalence of mutations of the extracellular domain of HER2. In embodiments, the ERBB2 mutation frequency was significantly higher in UC samples having a confirmed MPUC histology (about 40% of 15 samples analyzed), compared to a lower frequency in the non-MPUC samples (e.g., about 9% of 64 samples presenting a traditional UC histology). In particular, the Serine at position 310 is mutated to phenylalanine (S310F) or tyrosine (S310Y), and other functional mutations of HER2 are also observed. ERBB2 S310F is an activating HER2 mutation, which is sensitive to irreversible dual Egfr/Erbb2 inhibitors. ERBB2 mutations have not been previously reported in urothelial carcinoma (COSMIC, PubMed, August 2012), yet may suggest sensitivity to Her2-targeted drug therapies. These results further suggest a significant correlation of genotype to histologic phenotype and biologic behavior in an aggressive genitourinary neoplasm, a well delineated paradigm of HER2 mutation as an oncogenic driving genomic alteration.

Accordingly, disclosed herein are methods for treating for a urothelial and/or micropapillary carcinoma, including those of the urinary tract, bladder, urothelial cells, such as micropapillary urothelial carcinoma, using an agent (e.g., a therapeutic agent) that targets and/or inhibits HER2 (e.g., a HER2 gene product, e.g., a HER2 protein), as well as methods and reagents for identifying, assessing and/or detecting an alteration as described herein, e.g., a HER2 mutation, in a micropapillary carcinoma (e.g., micropapillary urothelial carcinoma).

Micropapillary morphology or histology occurs in neoplasms arising in different organ systems and displays aggressive biologic behavior regardless of its site of origin. Carcinomas with this morphology include those affecting organs and tissues, such as the urinary tract, bladder, urothelial cells, bile duct, thyroid, endometrium, breast and lung. An evaluation of a micropapillary morphology or histology can be carried out using methods known in the art as described in, for example, De Oliveira, R. et al. (2009) *American Journal of Clinical Pathology*, 131, 694-700 (for lung adenocarcinoma); and Singh K. et al. *Diagnostic Pathology* 2011, 6:13 (for endometrium)).

Micropapillary urothelial carcinoma of the urinary bladder is a rare, but highly aggressive form of bladder cancer associated with distant metastases and shortened patient survival. The micropapillary morphology or histology in the context of MPUC can be characterized by a distinctive histology featuring small micropapillae created by clusters of 4 to 5 cells across, peripherally situated nuclei and cytoplasmic vacuoles with a strong tendency to develop intra-lymphatic permeation or simulate lymphovascular involvement due to the production of peri-tumoral stromal retraction artifacts (described in, for example, (Amin M B, et al. (1994) *Am J Surg Pathol.* 18:1224-32); Sangoi A R, et al. (2010) *Am J Surg Pathol.* 34:1367-76; Kamat A M, et al. (2007) *Cancer* 110:62-7; López J I, et al. (1999) *Histopathology* 34:561-2).

"Human Epidermal Growth Factor Receptor 2" or "HER2" (also known as Neu, ErbB-2, CD340 (cluster of differentiation 340) or p185) refers to a HER2 molecule (e.g., a nucleic acid or protein). The HER2 protein refers to a protein, typically human HER2 that is encoded by the ERBB2 gene. HER2 is a member of the epidermal growth factor receptor (EGFR/ErbB) family. The ERBB family of receptor tyrosine kinases contains four known members: Epidermal Growth Factor receptor (EGFR, ERBB1, HER1); ERRB2 (HER2), ERBB3 (HER3), and ERBB4 (HER4).

HER2 protein is about 1255 amino acids in length. The HER2 amino and nucleotide sequences are known in the art (see e.g., Coussens L. et al. (1985) *Science* 230 (4730): 1132-9, and are reproduced herein below).

Amplification or over-expression of the ERBB2 gene has been shown to play an important role in the pathogenesis and progression of certain aggressive types of breast cancer. In recent years, it has evolved to become an important biomarker and target of therapy for the disease. Additional HER2 somatic mutations have been shown to be activating mutations that are likely to achieve tumorigenesis (see e.g., Bose et al. *Cancer Discov.* 3(2):224-37). Exemplary somatic mutations that activate the ERBB2 signaling can be divided into at least three types of small insertions and missense mutations in the kinase domain; missense mutations in the extracellular domain; and large deletions of the extracellular domain that yield the truncated form of ERBB2 (p95HER2) (Herter-Sprie G S, et al. (2013) *Front Oncol.* 3:86). The 5310 mutation is considered to be an activating mutation, sensitive to irreversible dual EGFR/ERBB2 inhibitors (Lee J C, et al. (2006) *PLoS Med.* 3:e485; Greulich H. et al. (2010) *Genes Cancer.* 1:1200-10; Greulich H, et al. (2012) *Proc Natl Acad Sci USA.* 109:14476-81).

Certain terms are defined below and throughout the specification.

As used herein, the articles "a" and "an" refer to one or to more than one (e.g., to at least one) of the grammatical object of the article.

The term "or" is used herein to mean, and is used interchangeably with, the term "and/or", unless context clearly indicates otherwise.

"About" and "approximately" shall generally mean an acceptable degree of error for the quantity measured given the nature or precision of the measurements. Exemplary degrees of error are within 20 percent (%), typically, within 10%, and more typically, within 5% of a given value or range of values.

"Acquire" or "acquiring" as the terms are used herein, refer to obtaining possession of a physical entity, or a value, e.g., a numerical value, by "directly acquiring" or "indirectly acquiring" the physical entity or value. "Directly acquiring" means performing a process (e.g., performing a synthetic or analytical method) to obtain the physical entity or value. "Indirectly acquiring" refers to receiving the physical entity or value from another party or source (e.g., a third party laboratory that directly acquired the physical entity or value). Directly acquiring a physical entity includes performing a process that includes a physical change in a physical substance, e.g., a starting material. Exemplary changes include making a physical entity from two or more starting materials, shearing or fragmenting a substance, separating or purifying a substance, combining two or more separate entities into a mixture, performing a chemical reaction that includes breaking or forming a covalent or non-covalent bond. Directly acquiring a value includes performing a process that includes a physical change in a sample or another substance, e.g., performing an analytical process which includes a physical change in a substance, e.g., a sample, analyte, or reagent (sometimes referred to herein as "physical analysis"), performing an analytical method, e.g., a method which includes one or more of the following: separating or purifying a substance, e.g., an analyte, or a fragment or other derivative thereof, from another substance; combining an analyte, or fragment or other derivative thereof, with another substance, e.g., a buffer, solvent, or reactant; or changing the structure of an analyte, or a fragment or other derivative thereof, e.g., by breaking or forming a covalent or non-covalent bond, between a first and a second atom of the analyte; or by changing the structure of a reagent, or a fragment or other derivative thereof, e.g., by breaking or forming a covalent or non-covalent bond, between a first and a second atom of the reagent.

"Acquiring a sequence" as the term is used herein, refers to obtaining possession of a nucleotide sequence or amino acid sequence, by "directly acquiring" or "indirectly acquiring" the sequence. "Directly acquiring a sequence" means performing a process (e.g., performing a synthetic or analytical method) to obtain the sequence, such as performing a sequencing method (e.g., a Next Generation Sequencing (NGS) method). "Indirectly acquiring a sequence" refers to receiving information or knowledge of, or receiving, the sequence from another party or source (e.g., a third party laboratory that directly acquired the sequence). The sequence acquired need not be a full sequence, e.g., sequencing of at least one nucleotide, or obtaining information or knowledge that identifies a mutation disclosed herein as being present in a subject constitutes acquiring a sequence.

Directly acquiring a sequence includes performing a process that includes a physical change in a physical substance, e.g., a starting material, such as a tissue sample, e.g., a biopsy, or an isolated nucleic acid (e.g., DNA or RNA) sample. Exemplary changes include making a physical entity from two or more starting materials, shearing or fragmenting a substance, such as a genomic DNA fragment; separating or purifying a substance (e.g., isolating a nucleic acid sample from a tissue); combining two or more separate entities into a mixture, performing a chemical reaction that includes breaking or forming a covalent or non-covalent bond. Directly acquiring a value includes performing a process that includes a physical change in a sample or another substance as described above.

"Acquiring a sample" as the term is used herein, refers to obtaining possession of a sample, e.g., a tissue sample or nucleic acid sample, by "directly acquiring" or "indirectly acquiring" the sample. "Directly acquiring a sample" means performing a process (e.g., performing a physical method such as a surgery or extraction) to obtain the sample. "Indirectly acquiring a sample" refers to receiving the sample from another party or source (e.g., a third party laboratory that directly acquired the sample). Directly acquiring a sample includes performing a process that includes a physical change in a physical substance, e.g., a starting material, such as a tissue, e.g., a tissue in a human patient or a tissue that has was previously isolated from a patient. Exemplary changes include making a physical entity from a starting material, dissecting or scraping a tissue; separating or purifying a substance (e.g., a sample tissue or a nucleic acid sample); combining two or more separate entities into a mixture; performing a chemical reaction that includes breaking or forming a covalent or non-covalent bond. Directly acquiring a sample includes performing a process that includes a physical change in a sample or another substance, e.g., as described above.

An "alteration" as used herein, of a gene or gene product (e.g., a HER2 gene or gene product) refers to the presence of a mutation or mutations within the gene or gene product, e.g., a mutation, which affects amount or activity of the gene or gene product, as compared to the normal or wild-type gene. The alteration can be in amount, structure, and/or activity in a cancer tissue or cancer cell, as compared to its amount, structure, and/or activity, in a normal or healthy tissue or cell (e.g., a control), and is associated with a disease state, such as cancer. For example, a gene or gene product which is associated with cancer, or predictive of responsiveness to anti-cancer therapeutics, can have an altered nucleotide sequence (e.g., a mutation), amino acid sequence, chromosomal translocation, intra-chromosomal inversion, copy number, expression level, protein level, protein activity, or methylation status, in a cancer tissue or cancer cell, as compared to a normal, healthy tissue or cell. Exemplary mutations include, but are not limited to, point mutations (e.g., silent, missense, or nonsense), deletions, insertions, inversions, linking mutations, duplications, translocations, inter- and intra-chromosomal rearrangements. Mutations can be present in the coding or non-coding region of the gene. In certain embodiments, the alterations are associated (or not associated) with a phenotype, e.g., a cancerous phenotype (e.g., one or more of cancer risk, cancer progression, cancer treatment or resistance to cancer treatment).

"Binding entity" means any molecule to which molecular tags can be directly or indirectly attached that is capable of specifically binding to an analyte. The binding entity can be an affinity tag on a nucleic acid sequence. In certain embodiments, the binding entity allows for separation of the nucleic acid from a mixture, such as an avidin molecule, or an antibody that binds to the hapten or an antigen-binding fragment thereof. Exemplary binding entities include, but are not limited to, a biotin molecule, a hapten, an antibody, an antibody binding fragment, a peptide, and a protein.

"Complementary" refers to sequence complementarity between regions of two nucleic acid strands or between two regions of the same nucleic acid strand. It is known that an adenine residue of a first nucleic acid region is capable of forming specific hydrogen bonds ("base pairing") with a residue of a second nucleic acid region which is antiparallel to the first region if the residue is thymine or uracil. Similarly, it is known that a cytosine residue of a first nucleic acid strand is capable of base pairing with a residue of a second nucleic acid strand which is antiparallel to the first strand if the residue is guanine. A first region of a nucleic acid is complementary to a second region of the same or a different nucleic acid if, when the two regions are arranged in an antiparallel fashion, at least one nucleotide residue of the first region is capable of base pairing with a residue of the second region. In certain embodiments, the first region comprises a first portion and the second region comprises a second portion, whereby, when the first and second portions are arranged in an antiparallel fashion, at least about 50%, at least about 75%, at least about 90%, or at least about 95% of the nucleotide residues of the first portion are capable of base pairing with nucleotide residues in the second portion. In other embodiments, all nucleotide residues of the first portion are capable of base pairing with nucleotide residues in the second portion.

The term "cancer" or "tumor" is used interchangeably herein. These terms refer to the presence of cells possessing characteristics typical of cancer-causing cells, such as uncontrolled proliferation, immortality, metastatic potential, rapid growth and proliferation rate, and certain characteristic morphological features.

The term "neoplasm" or "neoplastic" cell refers to an abnormal proliferative stage, e.g., a hyperproliferative stage, in a cell or tissue that can include a benign, pre-malignant, malignant (cancer) or metastatic stage.

Cancer is "inhibited" if at least one symptom of the cancer is alleviated, terminated, slowed, or prevented. As used herein, cancer is also "inhibited" if recurrence or metastasis of the cancer is reduced, slowed, delayed, or prevented.

"Chemotherapeutic agent" means a chemical substance, such as a cytotoxic or cytostatic agent that is used to treat a condition, particularly cancer.

As used herein, "cancer therapy" and "cancer treatment" are synonymous terms.

As used herein, "chemotherapy" and "chemotherapeutic" and "chemotherapeutic agent" are synonymous terms.

The terms "homology" or "identity," as used interchangeably herein, refer to sequence similarity between two polynucleotide sequences or between two polypeptide sequences, with identity being a more strict comparison. The phrases "percent identity or homology" and "% identity or homology" refer to the percentage of sequence similarity found in a comparison of two or more polynucleotide sequences or two or more polypeptide sequences. "Sequence similarity" refers to the percent similarity in base pair sequence (as determined by any suitable method) between two or more polynucleotide sequences. Two or more sequences can be anywhere from 0-100% similar, or any integer value there between. Identity or similarity can be determined by comparing a position in each sequence that can be aligned for purposes of comparison. When a position in the compared sequence is occupied by the same nucleotide base or amino acid, then the molecules are identical at that position. A degree of similarity or identity between polynucleotide sequences is a function of the number of identical or matching nucleotides at positions shared by the polynucleotide sequences. A degree of identity of polypeptide sequences is a function of the number of identical amino acids at positions shared by the polypeptide sequences. A degree of homology or similarity of polypeptide sequences is a function of the number of amino acids at positions shared by the polypeptide sequences. The term "substantially identical," as used herein, refers to an identity or homology of at least 75%, at least 80%, at least 85%, at least 90%, 91%, 92%, 93%, 94%, 95%, 96%, 97%, 98%, 99%, or more.

"Likely to" or "increased likelihood," as used herein, refers to an increased probability that an item, object, thing or person will occur. Thus, in one example, a subject that is likely to respond to treatment with a kinase inhibitor, alone or in combination, has an increased probability of responding to treatment with the inhibitor alone or in combination, relative to a reference subject or group of subjects.

"Unlikely to" refers to a decreased probability that an event, item, object, thing or person will occur with respect to a reference. Thus, a subject that is unlikely to respond to treatment with a kinase inhibitor, alone or in combination, has a decreased probability of responding to treatment with a kinase inhibitor, alone or in combination, relative to a reference subject or group of subjects.

"Sequencing" a nucleic acid molecule requires determining the identity of at least 1 nucleotide in the molecule. In embodiments, the identity of less than all of the nucleotides in a molecule is determined. In other embodiments, the identity of a majority or all of the nucleotides in the molecule is determined.

"Next-generation sequencing or NGS or NG sequencing" as used herein, refers to any sequencing method that determines the nucleotide sequence of either individual nucleic acid molecules (e.g., in single molecule sequencing) or clonally expanded proxies for individual nucleic acid molecules in a highly parallel fashion (e.g., greater than $10^5$ molecules are sequenced simultaneously). In one embodiment, the relative abundance of the nucleic acid species in the library can be estimated by counting the relative number of occurrences of their cognate sequences in the data generated by the sequencing experiment. Next generation sequencing methods are known in the art, and are described, e.g., in Metzker, M. (2010) *Nature Biotechnology Reviews* 11:31-46, incorporated herein by reference. Next generation sequencing can detect a variant present in less than 5% of the nucleic acids in a sample.

"Sample," "tissue sample," "patient sample," "patient cell or tissue sample" or "specimen" each refers to a collection of similar cells obtained from a tissue of a subject or patient. The source of the tissue sample can be solid tissue as from a fresh, frozen and/or preserved organ, tissue sample, biopsy, or aspirate; blood or any blood constituents; bodily fluids such as cerebral spinal fluid, amniotic fluid, peritoneal fluid or interstitial fluid; or cells from any time in gestation or development of the subject. The tissue sample can contain compounds that are not naturally intermixed with the tissue in nature such as preservatives, anticoagulants, buffers, fixatives, nutrients, antibiotics or the like. In one embodiment, the sample is preserved as a frozen sample or as formaldehyde- or paraformaldehyde-fixed paraffin-embedded (FFPE) tissue preparation. For example, the sample can be embedded in a matrix, e.g., an FFPE block or a frozen sample.

A "tumor nucleic acid sample" as used herein, refers to nucleic acid molecules from a tumor or cancer sample. Typically, it is DNA, e.g., genomic DNA, or cDNA derived from RNA, from a tumor or cancer sample. In certain embodiments, the tumor nucleic acid sample is purified or isolated (e.g., it is removed from its natural state).

A "control" or "reference" "nucleic acid sample" as used herein, refers to nucleic acid molecules from a control or reference sample. Typically, it is DNA, e.g., genomic DNA, or cDNA derived from RNA, not containing the alteration or variation in the gene or gene product, e.g., not containing a mutation. In certain embodiments, the reference or control nucleic acid sample is a wild type or a non-mutated sequence. In certain embodiments, the reference nucleic acid sample is purified or isolated (e.g., it is removed from its natural state). In other embodiments, the reference nucleic acid sample is from a non-tumor sample, e.g., a blood control, a normal adjacent tumor (NAT), or any other non-cancerous sample from the same or a different subject.

"Adjacent to the interrogation position," as used herein, means that a site sufficiently close such that a detection reagent complementary with the site can be used to distinguish between a mutation, e.g., an alteration described herein, and a reference sequence, e.g., a non-mutant or wild-type sequence, in a target nucleic acid. Directly adjacent, as used herein, is where 2 nucleotides have no intervening nucleotides between them.

"Associated mutation," as used herein, refers to a mutation within a preselected distance, in terms of nucleotide or primary amino acid sequence, from a definitional mutation, e.g., a mutant as described herein. In embodiments, the associated mutation is within n, wherein n is 2, 5, 10, 20, 30, 50, 100, or 200 nucleotides from the definitional mutation (n does not include the nucleotides defining the associated and definitional mutations). In embodiments, the associated mutation is a translocation mutation.

"Interrogation position," as used herein, comprises at least one nucleotide (or, in the case of polypeptides, an amino acid residue) which corresponds to a nucleotide (or amino acid residue) that is mutated in a mutation of interest, e.g., a mutation being identified, or in a nucleic acid (or protein) being analyzed, e.g., sequenced, or recovered.

A "reference sequence," as used herein, e.g., as a comparator for a mutant sequence, is a sequence which has a different nucleotide or amino acid at an interrogation position than does the mutant(s) being analyzed. In one embodiment, the reference sequence is wild-type for at least the interrogation position.

Headings, e.g., (a), (b), (i) etc, are presented merely for ease of reading the specification and claims. The use of headings in the specification or claims does not require the steps or elements be performed in alphabetical or numerical order or the order in which they are presented.

Various aspects featured in the invention are described in further detail below. Additional definitions are set out throughout the specification.

Therapeutic Methods and Agents

The invention provides, at least in part, methods for treating a cancer, e.g., a urothelial and/or micropapillary carcinoma (e.g., MPUC) in a subject. In certain embodiments, the methods include treatment of a urothelial and/or micropapillary carcinoma harboring an alteration described herein (e.g., a HER2 alteration described herein). The methods include administering to the subject a therapeutic agent, e.g., an agent that antagonizes the function of HER2.

In certain embodiments, the cancer, e.g., the urothelial and/or micropapillary carcinoma, is chosen from a cancer of the urinary system (e.g., kidney, bladder, ureter, urethra and urachus), urothelial cells, breast, lung, endometrium, bile duct or thyroid. In one embodiment, the micropapillary carcinoma is chosen from a cancer of the urinary tract, bladder, urothelial cells or bile duct. In one embodiment, the micropapillary carcinoma is a micropapillary urothelial carcinoma (MPUC). In one embodiment, the urothelial carcinoma is metastatic.

In certain embodiment, the cancer has, or is identified or determined as having, a histology of micropapillae. In certain embodiments, the micropapillary histology or histology of micropapillae comprises small micropapillae created by clusters of two or more cells (typically 4 to 5 cells) across, peripherally situated nuclei and cytoplasmic vacuoles.

In other embodiment, the cancer, e.g., the urothelial and/or micropapillary carcinoma (e.g., MPUC), comprises, or is identified or determined as having, an alteration in HER2, e.g., an alteration in HER2 as described herein. In one embodiment, the urothelial and/or micropapillary carcinoma (e.g., MPUC) does not have a gene amplification or overexpression of HER2 or a HER2 gene product. For example, the cancer is not an ERBB2-amplified cancer or carcinoma (e.g., an ERBB2-amplified urothelial carcinoma). In certain embodiments, the cancer does not have an elevated level of, or is negative for, a HER2 gene product (e.g., the cancer is negative for HER2 expression by nucleic acid or protein detection methods, e.g., PCR or immunohistochemistry).

"Treat," "treatment," and other forms of this word refer to the administration of an agent, e.g., a therapeutic agent, alone or in combination with a second agent in an amount effective to impede growth of a cancer, to cause a cancer to shrink by weight or volume, to extend the expected survival time of the subject and or time to progression of the tumor or the like. In those subjects, treatment can include, but is not limited to, inhibiting tumor growth, reducing tumor mass, reducing size or number of metastatic lesions, inhibiting the development of new metastatic lesions, prolonged survival, prolonged progression-free survival, prolonged time to progression, and/or enhanced quality of life. A cancer is "treated" if at least one symptom of the cancer is alleviated, terminated, slowed or prevented. A cancer is also "treated" if recurrence or metastasis of the cancer is reduced, slowed, delayed or prevented.

As used herein, unless otherwise specified, the terms "prevent," "preventing" and "prevention" contemplate an action that occurs before a subject begins to suffer from the re-growth of the cancer and/or which inhibits or reduces the severity of the cancer.

As used herein, and unless otherwise specified, a "therapeutically effective amount" of an agent is an amount sufficient to provide a therapeutic benefit in the treatment or management of the cancer, or to delay or minimize one or more symptoms associated with the cancer. A therapeutically effective amount of a compound means an amount of therapeutic agent, alone or in combination with other therapeutic agents, which provides a therapeutic benefit in the treatment or management of the cancer. The term "therapeutically effective amount" can encompass an amount that improves overall therapy, reduces or avoids symptoms or causes of the cancer, or enhances the therapeutic efficacy of another therapeutic agent.

As used herein, and unless otherwise specified, a "prophylactically effective amount" of an agent is an amount sufficient to prevent re-growth of the cancer, or one or more symptoms associated with the cancer, or prevent its recurrence. A prophylactically effective amount of an agent means an amount of the agent, alone or in combination with other therapeutic agents, which provides a prophylactic benefit in the prevention of the cancer. The term "prophylactically effective amount" can encompass an amount that improves overall prophylaxis or enhances the prophylactic efficacy of another prophylactic agent.

The term "patient" or "subject" includes a human (e.g., a male or female of any age group, e.g., a pediatric patient (e.g., infant, child, adolescent) or adult patient (e.g., young adult, middle-aged adult or senior adult). When the term is used in conjunction with administration of a compound or drug, then the patient has been the object of treatment, observation, and/or administration of the compound or drug.

These treatments can be provided to a patient having had an unsatisfactory response to a different (e.g., non-HER2) therapeutic agent or therapeutic modality. In one embodiment, the subject is undergoing or has undergone treatment with a different (e.g., non-HER2) therapeutic agent or therapeutic modality. In one embodiment, the non-HER2 therapeutic agent or therapeutic modality is a chemotherapy or a surgical procedure. In one embodiment, the non-HER2 therapeutic agent or therapeutic modality comprises one or more of: methotrexate, vinblastine, doxorubicin, and/or cisplatin (MVAC).

An agent, e.g., therapeutic agent, described herein can be administered, alone or in combination, e.g., in combination with other chemotherapeutic agents or procedures, in an amount sufficient to reduce or inhibit the tumor cell growth, and/or treat or prevent the cancer(s), in the subject.

The agent, e.g., therapeutic agent, can be a small molecule, a protein, a polypeptide, a peptide, an antibody molecule, a nucleic acid (e.g., a siRNA, an antisense or a micro RNA), a small molecule, or an immune cell therapy. Exemplary agents and classes of agents are described herein.

In one embodiment, the agent, e.g., therapeutic agent, binds and inhibits HER2. In one embodiment, the agent is an antibody molecule. The terms "antibody" and "antibody molecule" as used interchangeably herein refer to immunoglobulin molecules and immunologically active portions of immunoglobulin molecules, i.e., molecules that contain an antigen binding site which specifically binds an antigen, such as a polypeptide featured in the invention. A molecule which specifically binds to a given polypeptide featured in the invention is a molecule which binds the polypeptide, but does not substantially bind other molecules in a sample, e.g., a biological sample, which naturally contains the polypeptide. Examples of immunologically active portions of immunoglobulin molecules include F(ab) and F(ab')$_2$ fragments which can be generated by treating the antibody with an enzyme such as pepsin. The invention provides polyclonal and monoclonal antibodies. The term "monoclonal antibody" or "monoclonal antibody composition," as used herein, refers to a population of antibody molecules that contain only one species of an antigen binding site capable of immunoreacting with a particular epitope. Antibodies to HER2 are known in the art, as well as techniques for generating antibodies to a polypeptide target, e.g., HER2 (see e.g., WO 2012/092426, entitled "Optimization of Multigene Analysis of Tumor Samples," incorporated herein by reference.

In another embodiment, the agent is selected from an antisense molecule, a ribozymes, a double-stranded RNA molecule, a triple helix molecule, that hybridize to a nucleic acid encoding the mutation, or a transcription regulatory region that blocks or reduces mRNA expression of the mutation. In one embodiment, the agent is a kinase inhibitor. In one embodiment, the kinase inhibitor is chosen from: a multi-specific kinase inhibitor, a HER2 inhibitor, an ERBB2 inhibitor, an EGFR inhibitor (e.g., a pan ERBB inhibitor), an antibody molecule, (e.g., a monoclonal antibody) against HER2, and/or a small molecule inhibitor that is selective for HER2.

As used herein, a "pan ERBB inhibitor" is an inhibitor which is not specific for one ERBB family member but can inhibit all ERBB family members, e.g., HER1, HER2, HER3, and HER4.

In one embodiment, the agent is chosen from: AV-203, AMG 888, U3-1287, APC8024, DN24-02, Neuvenge, Lapuleucel-T, MM-111, MM-121, SAR256212, MM-141, LJM716, REGN1400, MEHD7945A, RG7597, RG7116, Trastuzumab, trastuzumab emtansine (T-DM1), pertuzumab, afatinib, TAK-285, Neratinib, Dacomitinib, BMS-690514, BMS-599626, Pelitinib, CP-724714, Lapatinib, TAK-165, ARRY-380, or AZD8931. In one embodiment, the agent is Neratinib. Each of these inhibitors is described in more detail below.

AV-203 is a humanized monoclonal antibody directed against ErbB-3; and is described in Cancer Research: Apr. 15, 2012; Volume 72, Issue 8, Supplement.AM2012-2509.

AMG-888 (U3-1287) is a human monoclonal antibody directed against epidermal growth factor receptor 3 (HER3); and is described in J Clin Oncol 29: 2011 (suppl; abstr 3026).

APC 8024 (Lapuleucel-T, Neuvenge, DN24-02) is an investigational autologous active cellular immunotherapy designed to stimulate an immune response against tumor cells expressing the cancer antigen HER-2/neu; and is described in Clin Cancer Res Sep. 15, 2009 15; 5937.

MM-111 is a bispecific antibody fusion protein that specifically targets the ErbB2/ErbB3 heterodimer and abrogates ligand binding; and is described in Cancer Res Dec. 15, 2010; 70(24 Supplement): P6-15-15.

MM-121 (sar256212) is a fully humanized monoclonal antibody directed against epidermal growth factor receptor 3 (HER3); and is described in Cancer Res. 2010 Mar. 15; 70(6):2485-94.

MM-141 monoclonal antibody that acts as a tetravalent inhibitor of PI3K/AKT/mTOR MM-141 is designed to interfere with this pathway by blocking ligand-induced signaling through the IGF-1R and ErbB3 receptors; and is described in *Oncotarget* 2012 August; 3(8): 744-758.

LJM716 is a fully human HuCAL-based antibody directed against HER3; and is described in *Cancer Research*: Apr. 15, 2012; Volume 72, Issue 8, Supplement 1. AM2012-2733.

REGN1400 is a fully human monoclonal antibody directed against ERBB3; and is described in *Cancer Research*: Apr. 15, 2012; Volume 72, Issue 8, Supplement 1.

MEHD7945A (RG7597) is a monoclonal antibody that dually targets EGFR and HER3; and is described in Cancer Res Jan. 15, 2013 73; 824.

RG7116 is a glycoengineered humanized monoclonal antibody directed against HER3. RG7116 is a therapeutic antibody that binds the inactive HER3 receptor and is optimized for immune effector activation; and is described in Mirschberger C et al. *Cancer Res.* 2013 Jun. 18 [Epub ahead of print].

Trastuzumab is a monoclonal antibody directed against HER2; and is described in British Journal of Cancer (2012) 106, 6-13.

Trastuzumab emtansine (T-DM1) is a monoclonal antibody directed against HER2 conjugated to a cytotoxic moiety; and is described in British Journal of Cancer (2012) 106, 6-13.

Pertuzumab is a monoclonal antibody directed against HER2; and is described in British Journal of Cancer (2012) 106, 6-13.

Afatinib is an anilino-quinazoline-derived irreversible small-molecule inhibitor of the ErbB family (EGFR/HER1, HER2 and HER4); and is described in British Journal of Cancer (2012) 106, 6-13.

TAK-285 is a low molecular weight compound which inhibits HER2 and EGFR kinase activities; and is described in Br J Cancer. 2012 Feb. 14; 106(4).

Neratinib is an irreversible small-molecule inhibitor of EGFR/HER1, HER2 and HER4; and is described in British Journal of Cancer (2012) 106, 6-13.

Dacomitinib is an irreversible small molecule inhibitor of the pan-EGFR family of tyrosine kinases (ErbB family), including ErbB-1, ErbB-2, and ErbB-3; and is described in PLoS One. 2013; 8(2): e56112.

BMS-690514 is a small molecule panHER/VEGFR/EGFR inhibitor; and is described in Cancer Res. 2007 Jul. 1; 67(13):6253-62.

BMS-599626 is a pyrrolotriazine-based small-molecule panHER/EGFR inhibitor; and is described in *Clin Cancer Res.* 2006 Oct. 15; 12(20 Pt 1):6186-93.

Pelitinib is a 3-cyanoquinoline pan-ErbB tyrosine kinase inhibitor, which irreversibly covalently binds to epidermal growth factor receptors (EGFR) ErbB-1, -2 and -4; and is described in *Nature Reviews Cancer* 10, 760-774 (November 2010).

CP-724714 is a small molecule inhibitor of erbB2 receptor; and is described in *Cancer Res.* 2007 Oct. 15; 67 (20):9887-93.

Lapatinib is a small molecule, reversible, dual inhibitor of EGFR/HER1 and HER2; and is described in British Journal of Cancer (2012) 106, 6-13.

TAK-165 (mubritinib) is a small molecule inhibitor of HER2; and is described in Int J Urol. 2006 May; 13(5):587-92.

ARRY-380 is a small molecule reversible HER2 inhibitor; and is described in Cancer Research: Dec. 15, 2009; Volume 69, Issue 24, Supplement 3. SABCS-09-5104.

AZD8931 is an equipotent reversible inhibitor of signaling by epidermal growth factor receptor, ERBB2 (HER2), and ERBB3; and is described in Clin Cancer Res. 2010 Feb. 15; 16(4):1159-69.CCR-09-2353.

The agents, e.g., the therapeutic agents described herein, can be administered in combination with a second therapeutic agent or a different therapeutic modality, e.g., anti-cancer agents, and/or in combination with surgical and/or radiation procedures.

By "in combination with," it is not intended to imply that the therapy or the therapeutic agents must be administered at the same time and/or formulated for delivery together, although these methods of delivery are within the scope of the invention. The pharmaceutical compositions can be administered concurrently with, prior to, or subsequent to, one or more other additional therapies or therapeutic agents. In general, each agent will be administered at a dose and/or on a time schedule determined for that agent. In will further be appreciated that the additional therapeutic agent utilized in this combination can be administered together in a single composition or administered separately in different compositions. The particular combination to employ in a regimen will take into account compatibility of the inventive pharmaceutical composition with the additional therapeutically active agent and/or the desired therapeutic effect to be achieved.

In certain embodiments, the cancer, e.g., the micropapillary carcinoma, comprises, or is identified or determined as having, an alteration in one or more of: AKT1, AKT2, CCND1, EGFR, PIK3CA, PIK3R1 or RAF1. In one embodiment, the cancer has a wild-type HER2 and comprises an alteration in one or more of: AKT1, AKT2, CCND1, EGFR, PIK3CA, PIK3R1 or RAF1. Such cancers can be treated with modulators, e.g., inhibitors, of one or more of: AKT1, AKT2, CCND1, EGFR, PIK3CA, PIK3R1 or RAF1.

Nucleic Acid Inhibitors

In yet another embodiment, the agent, e.g., the therapeutic agent, inhibits the expression of a nucleic acid encoding an alteration described herein. Examples of such agents include nucleic acid molecules, for example, antisense molecules, ribozymes, siRNA, triple helix molecules that hybridize to a nucleic acid encoding a mutation, or a transcription regulatory region, and blocks or reduces mRNA expression of the mutation.

In one embodiment, the nucleic acid antagonist is a siRNA that targets mRNA encoding a mutation. Other types of antagonistic nucleic acids can also be used, e.g., a dsRNA, a ribozyme, a triple-helix former, or an antisense nucleic acid. Accordingly, isolated nucleic acid molecules that are nucleic acid inhibitors, e.g., antisense, RNAi, to a mutation-encoding nucleic acid molecule are provided.

An "antisense" nucleic acid can include a nucleotide sequence which is complementary to a "sense" nucleic acid encoding a protein, e.g., complementary to the coding strand of a double-stranded cDNA molecule or complementary to an mRNA sequence. The antisense nucleic acid can be complementary to an entire mutation coding strand, or to only a portion thereof. In another embodiment, the antisense nucleic acid molecule is antisense to a "noncoding region" of the coding strand of a nucleotide sequence encoding mutation (e.g., the 5' and 3' untranslated regions). Anti-sense agents can include, for example, from about 8 to about 80 nucleobases (i.e., from about 8 to about 80 nucleotides), e.g., about 8 to about 50 nucleobases, or about 12 to about 30 nucleobases. Anti-sense compounds include ribozymes, external guide sequence (EGS) oligonucleotides (oligozymes), and other short catalytic RNAs or catalytic oligonucleotides which hybridize to the target nucleic acid and modulate its expression. Anti-sense compounds can include a stretch of at least eight consecutive nucleobases that are complementary to a sequence in the target gene. An oligonucleotide need not be 100% complementary to its target nucleic acid sequence to be specifically hybridizable. An oligonucleotide is specifically hybridizable when binding of the oligonucleotide to the target interferes with the normal function of the target molecule to cause a loss of utility, and there is a sufficient degree of complementarity to avoid non-specific binding of the oligonucleotide to non-target sequences under conditions in which specific binding is desired, i.e., under physiological conditions in the case of in vivo assays or therapeutic treatment or, in the case of in vitro assays, under conditions in which the assays are conducted.

Hybridization of antisense oligonucleotides with mRNA can interfere with one or more of the normal functions of mRNA. The functions of mRNA to be interfered with include all key functions such as, for example, translocation of the RNA to the site of protein translation, translation of protein from the RNA, splicing of the RNA to yield one or more mRNA species, and catalytic activity which may be engaged in by the RNA. Binding of specific protein(s) to the RNA may also be interfered with by antisense oligonucleotide hybridization to the RNA.

Exemplary antisense compounds include DNA or RNA sequences that specifically hybridize to the target nucleic acid, e.g., the mRNA encoding a mutation described herein. The complementary region can extend for between about 8 to about 80 nucleobases. The compounds can include one or more modified nucleobases. Modified nucleobases are known in the art. Descriptions of modified nucleic acid agents are also available. See, e.g., U.S. Pat. Nos. 4,987,071; 5,116,742; and U.S. Pat. No. 5,093,246; Woolf et al. (1992) *Proc Natl Acad Sci USA; Antisense RNA and DNA*, D. A. Melton, Ed., Cold Spring Harbor Laboratory, Cold Spring Harbor, N.Y. (1988); 89:7305-9; Haselhoff and Gerlach (1988) *Nature* 334:585-59; Helene, C. (1991) *Anticancer Drug Des.* 6:569-84; Helene (1992) *Ann. N.Y. Acad. Sci.* 660:27-36; and Maher (1992) *Bioassays* 14:807-15.

The antisense nucleic acid molecules are typically administered to a subject (e.g., by direct injection at a tissue site), or generated in situ such that they hybridize with or bind to cellular mRNA and/or genomic DNA encoding a mutation to thereby inhibit expression of the protein, e.g., by inhibiting transcription and/or translation. Alternatively, antisense nucleic acid molecules can be modified to target selected cells and then be administered systemically. For systemic administration, antisense molecules can be modified such that they specifically bind to receptors or antigens expressed on a selected cell surface, e.g., by linking the antisense nucleic acid molecules to peptides or antibodies which bind to cell surface receptors or antigens. The antisense nucleic acid molecules can also be delivered to cells using the vectors described herein. To achieve sufficient intracellular concentrations of the antisense molecules, vector constructs in which the antisense nucleic acid molecule is placed under the control of a strong pol II or pol III promoter are preferred.

In yet another embodiment, the antisense nucleic acid molecule is an α-anomeric nucleic acid molecule. An α-anomeric nucleic acid molecule forms specific double-stranded hybrids with complementary RNA in which, contrary to the usual β-units, the strands run parallel to each other (Gaultier et al. (1987) *Nucleic Acids. Res.* 15:6625-6641). The antisense nucleic acid molecule can also comprise a 2'-o-methylribonucleotide (Inoue et al. (1987) *Nucleic Acids Res.* 15:6131-6148) or a chimeric RNA-DNA analogue (Inoue et al. (1987) *FEBS Lett.* 215:327-330).

siRNAs are small double stranded RNAs (dsRNAs) that optionally include overhangs. For example, the duplex region of an siRNA is about 18 to 25 nucleotides in length, e.g., about 19, 20, 21, 22, 23, or 24 nucleotides in length. Typically, the siRNA sequences are exactly complementary to the target mRNA. dsRNAs and siRNAs in particular can be used to silence gene expression in mammalian cells (e.g., human cells). siRNAs also include short hairpin RNAs (shRNAs) with 29-base-pair stems and 2-nucleotide 3' overhangs. See, e.g., Clemens et al. (2000) *Proc. Natl. Acad. Sci. USA* 97:6499-6503; Billy et al. (2001) *Proc. Natl. Sci. USA* 98:14428-14433; Elbashir et al. (2001) *Nature.* 411:494-8; Yang et al. (2002) *Proc. Natl. Acad. Sci. USA* 99:9942-9947; Siolas et al. (2005), *Nat. Biotechnol.* 23(2):227-31; 20040086884; U.S. 20030166282; 20030143204; 20040038278; and 20030224432.

In still another embodiment, an antisense nucleic acid featured in the invention is a ribozyme. A ribozyme having specificity for a mutation-encoding nucleic acid can include one or more sequences complementary to the nucleotide sequence of a mutation cDNA disclosed herein (i.e., SEQ ID NO:6), and a sequence having known catalytic sequence responsible for mRNA cleavage (see U.S. Pat. No. 5,093, 246 or Haselhoff and Gerlach (1988) *Nature* 334:585-591). For example, a derivative of a Tetrahymena L-19 IVS RNA can be constructed in which the nucleotide sequence of the active site is complementary to the nucleotide sequence to be cleaved in a mutation-encoding mRNA. See, e.g., Cech et al. U.S. Pat. No. 4,987,071; and Cech et al. U.S. Pat. No. 5,116,742. Alternatively, mutation mRNA can be used to select a catalytic RNA having a specific ribonuclease activity from a pool of RNA molecules. See, e.g., Bartel, D. and Szostak, J. W. (1993) *Science* 261:1411-1418.

Inhibition of a mutated gene can be accomplished by targeting nucleotide sequences complementary to the regulatory region of the mutation to form triple helical structures that prevent transcription of the mutated gene in target cells. See generally, Helene, C. (1991) *Anticancer Drug Des.* 6:569-84; Helene, C. i (1992) *Ann. N.Y. Acad. Sci.* 660:27-36; and Maher, L. J. (1992) *Bioassays* 14:807-15. The potential sequences that can be targeted for triple helix formation can be increased by creating a so-called "switchback" nucleic acid molecule. Switchback molecules are synthesized in an alternating 5'-3', 3'-5' manner, such that they base pair with first one strand of a duplex and then the other, eliminating the necessity for a sizeable stretch of either purines or pyrimidines to be present on one strand of a duplex.

The invention also provides detectably labeled oligonucleotide primer and probe molecules. Typically, such labels are chemiluminescent, fluorescent, radioactive, or colorimetric.

A mutated nucleic acid molecule can be modified at the base moiety, sugar moiety or phosphate backbone to improve, e.g., the stability, hybridization, or solubility of the molecule. For non-limiting examples of synthetic oligonucleotides with modifications see Toulme (2001) *Nature Biotech.* 19:17 and Faria et al. (2001) *Nature Biotech.* 19:40-44. Such phosphoramidite oligonucleotides can be effective antisense agents.

For example, the deoxyribose phosphate backbone of the nucleic acid molecules can be modified to generate peptide nucleic acids (see Hyrup B. et al. (1996) *Bioorganic & Medicinal Chemistry* 4: 5-23). As used herein, the terms "peptide nucleic acid" or "PNA" refers to a nucleic acid mimic, e.g., a DNA mimic, in which the deoxyribose phosphate backbone is replaced by a pseudopeptide backbone and only the four natural nucleobases are retained. The neutral backbone of a PNA can allow for specific hybridization to DNA and RNA under conditions of low ionic strength. The synthesis of PNA oligomers can be performed using standard solid phase peptide synthesis protocols as described in Hyrup B. et al. (1996) supra and Perry-O'Keefe et al. *Proc. Natl. Acad. Sci.* 93: 14670-675.

PNAs of mutated nucleic acid molecules can be used in therapeutic and diagnostic applications. For example, PNAs can be used as antisense or antigene agents for sequence-specific modulation of gene expression by, for example, inducing transcription or translation arrest or inhibiting replication. PNAs of mutated nucleic acid molecules can also be used in the analysis of single base pair mutations in a gene, (e.g., by PNA-directed PCR clamping); as 'artificial restriction enzymes' when used in combination with other enzymes, (e.g., 51 nucleases (Hyrup B. et al. (1996) supra)); or as probes or primers for DNA sequencing or hybridization (Hyrup B. et al. (1996) supra; Perry-O'Keefe supra).

In other embodiments, the oligonucleotide may include other appended groups such as peptides (e.g., for targeting host cell receptors in vivo), or agents facilitating transport across the cell membrane (see, e.g., Letsinger et al. (1989) *Proc. Natl. Acad. Sci. USA* 86:6553-6556; Lemaitre et al. (1987) *Proc. Natl. Acad. Sci. USA* 84:648-652; WO88/09810) or the blood-brain barrier (see, e.g., WO 89/10134). In addition, oligonucleotides can be modified with hybridization-triggered cleavage agents (see, e.g., Krol et al. (1988) *Bio-Techniques* 6:958-976) or intercalating agents (See, e.g., Zon (1988) *Pharm. Res.* 5:539-549). To this end, the oligonucleotide may be conjugated to another molecule, (e.g., a peptide, hybridization triggered cross-linking agent, transport agent, or hybridization-triggered cleavage agent).

In some embodiments, a nucleic acid inhibitor described herein is provided for the inhibition of expression of a nucleic acid comprising the alteration in vitro.

Evaluation of Subjects

Subjects, e.g., patients, can be evaluated for the presence of an alteration, e.g., an alteration as described herein. A patient can be evaluated, for example, by determining the genomic sequence of the patient, e.g., by an NGS method. Alternatively, or in addition, evaluation of a patient can include directly assaying for the presence of a mutation in the patient, such as by an assay to detect a mutated nucleic acid (e.g., DNA or RNA), such as by, Southern blot, Northern blot, or RT-PCR, e.g., qRT-PCR. Alternatively, or in addition, a patient can be evaluated for the presence of a protein mutation, such as by immunohistochemistry, Western blot, immunoprecipitation, or immunomagnetic bead assay.

In one aspect, the results of a clinical trial, e.g., a successful or unsuccessful clinical trial, can be repurposed to identify agents that target an alteration disclosed herein, e.g., a HER2 mutation. By one exemplary method, a candidate agent used in a clinical trial can be reevaluated to determine if the agent in the trial targets a mutation, or is effective to treat a tumor containing a particular mutation. For example, subjects who participated in a clinical trial for an agent, such as a kinase inhibitor, can be identified. Patients who experienced an improvement in symptoms, e.g., cancer (e.g., a urothelial and/or micropapillary carcinoma, e.g., MPUC) symptoms, such as decreased tumor size, or decreased rate of tumor growth, can be evaluated for the presence of a mutation. Patients who did not experience an improvement in cancer symptoms can also be evaluated for the presence of a mutation. Where patients carrying a mutation are found to have been more likely to respond to the test agent than patients who did not carry such a mutation, then the agent is determined to be an appropriate treatment option for a patient carrying the mutation.

"Reevaluation" of patients can include, for example, determining the genomic sequence of the patients, or a subset of the clinical trial patients, e.g., by an NGS method. Alternatively, or in addition, reevaluation of the patients can include directly assaying for the presence of a mutation in the patient, such as by an assay to detect a mutated nucleic acid (e.g., RNA), such as by RT-PCR, e.g., qRT-PCR. Alternatively, or in addition, a patient can be evaluated for the presence of a protein mutation, such as by immunohistochemistry, Western blot, immunoprecipitation, or immunomagnetic bead assay.

Methods for Detection of Nucleic Acids and Polypeptides

Methods for evaluating a mutated gene, mutations and/or gene products are known to those of skill in the art. In one embodiment, the mutation is detected in a nucleic acid molecule by a method chosen from one or more of: nucleic acid hybridization assay, SSP, HPLC or mass-spectrometric genotyping.

Additional exemplary methods include traditional "direct probe" methods such as Southern blots and "comparative probe" methods such as comparative genomic hybridization (CGH), e.g., cDNA-based or oligonucleotide-based CGH, can be used. The methods can be used in a wide variety of formats including, but not limited to, substrate (e.g., membrane or glass) bound methods or array-based approaches.

In certain embodiments, the evaluation methods include probes/primers against the alterations described herein.

In one embodiment, probes/primers can be designed to detect a mutation or a reciprocal thereof. These probes/primers are suitable, e.g., for PCR amplification. Probes are used that contain DNA segments that are essentially complementary to DNA base sequences existing in different portions of chromosomes. Examples of probes useful according to the invention, and labeling and hybridization of probes to samples are described in two U.S. patents to Vysis, Inc. U.S. Pat. Nos. 5,491,224 and 6,277,569 to Bittner, et al.

Chromosomal probes are typically about 50 to about $10^5$ nucleotides in length. Longer probes typically comprise smaller fragments of about 100 to about 500 nucleotides in length. Probes that hybridize with centromeric DNA and locus-specific DNA are available commercially, for example, from Vysis, Inc. (Downers Grove, Ill.), Molecular Probes, Inc. (Eugene, Oreg.) or from Cytocell (Oxfordshire, UK). Alternatively, probes can be made non-commercially from chromosomal or genomic DNA through standard techniques. For example, sources of DNA that can be used include genomic DNA, cloned DNA sequences, somatic cell hybrids that contain one, or a part of one, chromosome (e.g., human chromosome) along with the normal chromosome complement of the host, and chromosomes purified by flow cytometry or microdissection. The region of interest can be isolated through cloning, or by site-specific amplification via the polymerase chain reaction (PCR). See, for example, Nath and Johnson, Biotechnic Histochem., 1998, 73(1):6-22, Wheeless et al., Cytometry 1994, 17:319-326, and U.S. Pat. No. 5,491,224.

The probes to be used hybridize to a specific region of a chromosome to determine whether a cytogenetic abnormality is present in this region. One type of cytogenetic abnormality is a deletion. Although deletions can be of one or more entire chromosomes, deletions normally involve loss of part of one or more chromosomes. If the entire region of a chromosome that is contained in a probe is deleted from a cell, hybridization of that probe to the DNA from the cell will normally not occur and no signal will be present on that chromosome. If the region of a chromosome that is partially contained within a probe is deleted from a cell, hybridization of that probe to the DNA from the cell can still occur, but less of a signal can be present. For example, the loss of a signal is compared to probe hybridization to DNA from control cells that do not contain the genetic abnormalities which the probes are intended to detect. In some embodiments, at least 1, 5, 10, 20, 30, 40, 50, 60, 70, 80, 90, 100, 110, 120, 130, 140, 150, 160, 170, 180, 190, 200, or more cells are enumerated for presence of the cytogenetic abnormality.

Cytogenetic abnormalities to be detected can include, but are not limited to, non-reciprocal translocations, balanced translocations, intra-chromosomal inversions, point mutations, deletions, gene copy number changes, gene expression level changes, and germ line mutations. In particular, one type of cytogenetic abnormality is a duplication. Duplications can be of entire chromosomes, or of regions smaller than an entire chromosome. If the region of a chromosome that is contained in a probe is duplicated in a cell, hybridization of that probe to the DNA from the cell will normally produce at least one additional signal as compared to the number of signals present in control cells with no abnormality of the chromosomal region contained in the probe.

Chromosomal probes are labeled so that the chromosomal region to which they hybridize can be detected. Probes typically are directly labeled with a fluorophore, an organic molecule that fluoresces after absorbing light of lower wavelength/higher energy. The fluorophore allows the probe to be visualized without a secondary detection molecule. After covalently attaching a fluorophore to a nucleotide, the nucleotide can be directly incorporated into the probe with standard techniques such as nick translation, random priming, and PCR labeling. Alternatively, deoxycytidine nucleotides within the probe can be transaminated with a linker. The fluorophore then is covalently attached to the transaminated deoxycytidine nucleotides. See, U.S. Pat. No. 5,491,224.

U.S. Pat. No. 5,491,224 describes probe labeling as a number of the cytosine residues having a fluorescent label covalently bonded thereto. The number of fluorescently labeled cytosine bases is sufficient to generate a detectable fluorescent signal while the individual so labeled DNA segments essentially retain their specific complementary binding (hybridizing) properties with respect to the chromosome or chromosome region to be detected. Such probes are made by taking the unlabeled DNA probe segment, transaminating with a linking group a number of deoxycytidine nucleotides in the segment, covalently bonding a fluorescent label to at least a portion of the transaminated deoxycytidine bases.

Probes can also be labeled by nick translation, random primer labeling or PCR labeling. Labeling is done using either fluorescent (direct)- or haptene (indirect)-labeled nucleotides. Representative, non-limiting examples of labels include: AMCA-6-dUTP, CascadeBlue-4-dUTP, Fluorescein-12-dUTP, Rhodamine-6-dUTP, TexasRed-6-dUTP, Cy3-6-dUTP, Cy5-dUTP, Biotin(BIO)-11-dUTP, Digoxygenin(DIG)-11-dUTP or Dinitrophenyl (DNP)-11-dUTP.

Probes also can be indirectly labeled with biotin or digoxygenin, or labeled with radioactive isotopes such as $^{32}P$ and $^{3}H$, although secondary detection molecules or further processing then is required to visualize the probes. For example, a probe labeled with biotin can be detected by avidin conjugated to a detectable marker. For example, avidin can be conjugated to an enzymatic marker such as alkaline phosphatase or horseradish peroxidase. Enzymatic markers can be detected in standard colorimetric reactions using a substrate and/or a catalyst for the enzyme. Catalysts for alkaline phosphatase include 5-bromo-4-chloro-3-indolylphosphate and nitro blue tetrazolium. Diaminobenzoate can be used as a catalyst for horseradish peroxidase.

Probes can also be prepared such that a fluorescent or other label is not part of the DNA before or during the hybridization, and is added after hybridization to detect the probe hybridized to a chromosome. For example, probes can be used that have antigenic molecules incorporated into the DNA. After hybridization, these antigenic molecules are detected using specific antibodies reactive with the antigenic molecules. Such antibodies can themselves incorporate a fluorochrome, or can be detected using a second antibody with a bound fluorochrome.

However treated or modified, the probe DNA is commonly purified in order to remove unreacted, residual products (e.g., fluorochrome molecules not incorporated into the DNA) before use in hybridization.

Prior to hybridization, chromosomal probes are denatured according to methods well known in the art. Probes can be hybridized or annealed to the chromosomal DNA under hybridizing conditions. "Hybridizing conditions" are conditions that facilitate annealing between a probe and target chromosomal DNA. Since annealing of different probes will vary depending on probe length, base concentration and the like, annealing is facilitated by varying probe concentration, hybridization temperature, salt concentration and other factors well known in the art.

Hybridization conditions are facilitated by varying the concentrations, base compositions, complexities, and lengths of the probes, as well as salt concentrations, temperatures, and length of incubation. For example, in situ hybridizations are typically performed in hybridization buffer containing 1-2×SSC, 50-65% formamide and blocking DNA to suppress non-specific hybridization. In general, hybridization conditions, as described above, include temperatures of about 25° C. to about 55° C., and incubation lengths of about 0.5 hours to about 96 hours.

Non-specific binding of chromosomal probes to DNA outside of the target region can be removed by a series of washes. Temperature and concentration of salt in each wash are varied to control stringency of the washes. For example, for high stringency conditions, washes can be carried out at about 65° C. to about 80° C., using 0.2× to about 2×SSC, and about 0.1% to about 1% of a non-ionic detergent such as Nonidet P-40 (NP40). Stringency can be lowered by decreasing the temperature of the washes or by increasing the concentration of salt in the washes. In some applications it is necessary to block the hybridization capacity of repetitive sequences. Thus, in some embodiments, tRNA, human genomic DNA, or Cot-I DNA is used to block non-specific hybridization. After washing, the slide is allowed to drain and air dry, then mounting medium, a counterstain such as DAPI, and a coverslip are applied to the slide. Slides can be viewed immediately or stored at −20° C. before examination.

In CGH methods, a first collection of nucleic acids (e.g., from a sample, e.g., a possible tumor) is labeled with a first label, while a second collection of nucleic acids (e.g., a control, e.g., from a healthy cell/tissue) is labeled with a second label. The ratio of hybridization of the nucleic acids is determined by the ratio of the two (first and second) labels binding to each fiber in the array. Where there are chromosomal deletions or multiplications, differences in the ratio of the signals from the two labels will be detected and the ratio will provide a measure of the copy number. Array-based CGH can also be performed with single-color labeling (as opposed to labeling the control and the possible tumor sample with two different dyes and mixing them prior to hybridization, which will yield a ratio due to competitive hybridization of probes on the arrays). In single color CGH, the control is labeled and hybridized to one array and absolute signals are read, and the possible tumor sample is labeled and hybridized to a second array (with identical content) and absolute signals are read. Copy number difference is calculated based on absolute signals from the two arrays. Hybridization protocols suitable for use with the methods featured in the invention are described, e.g., in Albertson (1984) *EMBO J.* 3: 1227-1234; Pinkel (1988) *Proc. Natl. Acad. Sci. USA* 85: 9138-9142; EPO Pub. No. 430,402; *Methods in Molecular Biology*, Vol. 33: In situ Hybridization Protocols, Choo, ed., Humana Press, Totowa, N.J. (1994), etc. In one embodiment, the hybridization protocol of Pinkel, et al. (1998) *Nature Genetics* 20: 207-211, or of Kallioniemi (1992) *Proc. Natl Acad Sci USA* 89:5321-5325 (1992) is used. Array-based CGH is described in U.S. Pat. No. 6,455,258, the contents of each of which are incorporated herein by reference.

In still another embodiment, amplification-based assays can be used to measure presence/absence and copy number. In such amplification-based assays, the nucleic acid sequences act as a template in an amplification reaction (e.g., Polymerase Chain Reaction (PCR). In a quantitative amplification, the amount of amplification product will be proportional to the amount of template in the original sample. Comparison to appropriate controls, e.g., healthy tissue, provides a measure of the copy number.

Methods of "quantitative" amplification are well known to those of skill in the art. For example, quantitative PCR involves simultaneously co-amplifying a known quantity of a control sequence using the same primers. This provides an internal standard that can be used to calibrate the PCR reaction. Detailed protocols for quantitative PCR are provided in Innis, et al. (1990) *PCR Protocols, A Guide to Methods and Applications*, Academic Press, Inc. N.Y.). Measurement of DNA copy number at microsatellite loci using quantitative PCR analysis is described in Ginzonger, et al. (2000) *Cancer Research* 60:5405-5409. The known nucleic acid sequence for the genes is sufficient to enable one of skill in the art to routinely select primers to amplify any portion of the gene. Fluorogenic quantitative PCR can also be used. In fluorogenic quantitative PCR, quantitation is based on amount of fluorescence signals, e.g., TaqMan and sybr green.

Other suitable amplification methods include, but are not limited to, ligase chain reaction (LCR) (see Wu and Wallace (1989) *Genomics* 4: 560, Landegren, et al. (1988) *Science* 241:1077, and Barringer et al. (1990) *Gene* 89: 117), transcription amplification (Kwoh, et al. (1989) *Proc. Natl. Acad. Sci. USA* 86: 1173), self-sustained sequence replication (Guatelli, et al. (1990) *Proc. Nat. Acad. Sci. USA* 87: 1874), dot PCR, and linker adapter PCR, etc.

Nucleic Acid Samples

A variety of tissue samples can be the source of the nucleic acid samples used in the present methods. Genomic or subgenomic DNA fragments can be isolated from a subject's sample (e.g., a tumor sample, a normal adjacent tissue (NAT), a blood sample or any normal control)). In certain embodiments, the tissue sample is preserved as a frozen sample or as formaldehyde- or paraformaldehyde-fixed paraffin-embedded (FFPE) tissue preparation. For example, the sample can be embedded in a matrix, e.g., an FFPE block or a frozen sample. The isolating step can include flow-sorting of individual chromosomes; and/or micro-dissecting a subject's sample (e.g., a tumor sample, a NAT, a blood sample).

Protocols for DNA isolation, fragmentation and processing from a tissue sample are known in the art as described, e.g., in WO 2012/092426, entitled "Optimization of Multigene Analysis of Tumor Samples," incorporated herein by reference in its entirety. Additional methods to isolate nucleic acids (e.g., DNA) from formaldehyde- or paraformaldehyde-fixed, paraffin-embedded (FFPE) tissues are disclosed, e.g., in Cronin M. et al., (2004) *Am J Pathol.* 164(1):35-42; Masuda N. et al., (1999) *Nucleic Acids Res.* 27(22):4436-4443; Specht K. et al., (2001) *Am J Pathol.* 158(2):419-429, Ambion RecoverAll™ Total Nucleic Acid Isolation Protocol (Ambion, Cat. No. AM1975, September 2008), and QIAamp® DNA FFPE Tissue Handbook (Qiagen, Cat. No. 37625, October 2007). RecoverAll™ Total Nucleic Acid Isolation Kit uses xylene at elevated temperatures to solubilize paraffin-embedded samples and a glass-fiber filter to capture nucleic acids. QIAamp® DNA FFPE Tissue Kit uses QIAamp® DNA Micro technology for purification of genomic and mitochondrial DNA.

Design of Baits

A bait can be a nucleic acid molecule, e.g., a DNA or RNA molecule, which can hybridize to (e.g., be complementary to), and thereby allow capture of a target nucleic acid. In one embodiment, a bait is an RNA molecule. In other embodiments, a bait includes a binding entity, e.g., an affinity tag, that allows capture and separation, e.g., by binding to a binding entity, of a hybrid formed by a bait and a nucleic acid hybridized to the bait. In one embodiment, a bait is suitable for solution phase hybridization.

Baits can be produced and used by methods and hybridization conditions as described in US 2010/0029498 and Gnirke, A. et al. (2009) *Nat Biotechnol.* 27(2):182-189, and WO 2012/092426, entitled "Optimization of Multigene Analysis of Tumor Samples, incorporated herein by reference.

Sequencing

The invention also includes methods of sequencing nucleic acids. In one embodiment, any of a variety of sequencing reactions known in the art can be used to directly sequence at least a portion of a mutation. In one embodiment, the mutated sequence is compared to a corresponding reference (control) sequence.

In one embodiment, the sequence of the nucleic acid molecule comprising an alteration described herein is determined by a method that includes one or more of: hybridizing an oligonucleotide, e.g., an allele specific oligonucleotide for one mutation described herein to said nucleic acid; hybridizing a primer, or a primer set (e.g., a primer pair), that amplifies a region comprising the mutation of the allele; amplifying, e.g., specifically amplifying, a region comprising the mutation of the allele; attaching an adapter oligonucleotide to one end of a nucleic acid that comprises the mutation of the allele; generating an optical, e.g., a colorimetric signal, specific to the presence of the one of the mutation; hybridizing a nucleic acid comprising the mutation to a second nucleic acid, e.g., a second nucleic acid attached to a substrate; generating a signal, e.g., an electrical or fluorescent signal, specific to the presence of the mutation; and incorporating a nucleotide into an oligonucleotide that is hybridized to a nucleic acid that contains the mutation.

In another embodiment, the sequence is determined by a method that comprises one or more of: determining the nucleotide sequence from an individual nucleic acid molecule, e.g., where a signal corresponding to the sequence is derived from a single molecule as opposed, e.g., from a sum of signals from a plurality of clonally expanded molecules; determining the nucleotide sequence of clonally expanded proxies for individual nucleic acid molecules; massively parallel short-read sequencing; template-based sequencing; pyrosequencing; real-time sequencing comprising imaging the continuous incorporation of dye-labeling nucleotides during DNA synthesis; nanopore sequencing; sequencing by hybridization; nano-transistor array based sequencing; polony sequencing; scanning tunneling microscopy (STM) based sequencing; or nanowire-molecule sensor based sequencing.

Any method of sequencing known in the art can be used. Exemplary sequencing reactions include those based on techniques developed by Maxam and Gilbert (*Proc. Natl Acad Sci USA* (1977) 74:560) or Sanger (Sanger et al. (1977) *Proc. Nat. Acad. Sci* 74:5463). Any of a variety of automated sequencing procedures can be utilized when performing the assays (*Biotechniques* (1995) 19:448), including sequencing by mass spectrometry (see, for example, U.S. Pat. No. 5,547,835 and international patent application Publication Number WO 94/16101, entitled DNA Sequencing by Mass Spectrometry by H. Köster; U.S. Pat. No. 5,547,835 and international patent application Publication Number WO 94/21822 entitled DNA Sequencing by Mass Spectrometry Via Exonuclease Degradation by H. Köster), and U.S. Pat. No. 5,605,798 and International Patent Application No. PCT/US96/03651 entitled DNA Diagnostics Based on Mass Spectrometry by H. Köster; Cohen et al. (1996) *Adv Chromatogr* 36:127-162; and Griffin et al. (1993) *Appl Biochem Biotechnol* 38:147-159).

Sequencing of nucleic acid molecules can also be carried out using next-generation sequencing (NGS). Next-generation sequencing includes any sequencing method that determines the nucleotide sequence of either individual nucleic acid molecules or clonally expanded proxies for individual nucleic acid molecules in a highly parallel fashion (e.g., greater than $10^5$ molecules are sequenced simultaneously). In one embodiment, the relative abundance of the nucleic acid species in the library can be estimated by counting the relative number of occurrences of their cognate sequences in the data generated by the sequencing experiment. Next generation sequencing methods are known in the art, and are described, e.g., in Metzker, M. (2010) *Nature Biotechnology Reviews* 11:31-46, incorporated herein by reference.

In one embodiment, the next-generation sequencing allows for the determination of the nucleotide sequence of an individual nucleic acid molecule (e.g., Helicos BioSciences' HeliScope Gene Sequencing system, and Pacific Biosciences' PacBio RS system). In other embodiments, the sequencing method determines the nucleotide sequence of clonally expanded proxies for individual nucleic acid molecules (e.g., the Solexa sequencer, Illumina Inc., San Diego, Calif.; 454 Life Sciences (Branford, Conn.), and Ion Torrent). e.g., massively parallel short-read sequencing (e.g., the Solexa sequencer, Illumina Inc., San Diego, Calif.), which generates more bases of sequence per sequencing unit than other sequencing methods that generate fewer but longer reads. Other methods or machines for next-generation sequencing include, but are not limited to, the sequencers provided by 454 Life Sciences (Branford, Conn.), Applied Biosystems (Foster City, Calif.; SOLiD sequencer), and Helicos BioSciences Corporation (Cambridge, Mass.).

Platforms for next-generation sequencing include, but are not limited to, Roche/454's Genome Sequencer (GS) FLX System, Illumina/Solexa's Genome Analyzer (GA), Life/APG's Support Oligonucleotide Ligation Detection (SOLiD) system, Polonator's G.007 system, Helicos BioSciences' HeliScope Gene Sequencing system, and Pacific Biosciences' PacBio RS system.

NGS technologies can include one or more of steps, e.g., template preparation, sequencing and imaging, and data analysis as described in WO 2012/092426, entitled "Optimization of Multigene Analysis of Tumor Samples, incorporated herein by reference.

Data Analysis

After NGS reads have been generated, they can be aligned to a known reference sequence or assembled de novo.

For example, identifying genetic variations such as single-nucleotide polymorphism and structural variants in a sample (e.g., a tumor sample) can be accomplished by aligning NGS reads to a reference sequence (e.g., a wild-type sequence). Methods of sequence alignment for NGS are described e.g., in Trapnell C. and Salzberg S. L. *Nature Biotech.*, 2009, 27:455-457.

Examples of de novo assemblies are described, e.g., in Warren R. et al., *Bioinformatics*, 2007, 23:500-501; Butler J. et al., *Genome Res.*, 2008, 18:810-820; and Zerbino D. R. and Birney E., *Genome Res.*, 2008, 18:821-829.

Sequence alignment or assembly can be performed using read data from one or more NGS platforms, e.g., mixing Roche/454 and Illumina/Solexa read data.

Algorithms and methods for data analysis are described in WO 2012/092426, entitled "Optimization of Multigene Analysis of Tumor Samples, incorporated herein by reference.

Detection of Mutated Polypeptide

The activity or level of a mutated polypeptide (e.g., a HER2 mutation) can also be detected and/or quantified by detecting or quantifying the expressed polypeptide. The mutated polypeptide can be detected and quantified by any of a number of means known to those of skill in the art. These can include analytic biochemical methods such as electrophoresis, capillary electrophoresis, high performance liquid chromatography (HPLC), thin layer chromatography (TLC), hyperdiffusion chromatography, and the like, or various immunological methods such as fluid or gel precipitin reactions, immunodiffusion (single or double), immunoelectrophoresis, radioimmunoassay (RIA), enzyme-linked immunosorbent assays (ELISAs), immunofluorescent assays, Western blotting, immunohistochemistry (IHC) and the like. A skilled artisan can adapt known protein/antibody detection methods.

Another agent for detecting a mutated polypeptide is an antibody molecule capable of binding to a polypeptide corresponding to a polypeptide, e.g., an antibody with a detectable label. Techniques for generating antibodies are described herein. The term "labeled", with regard to the probe or antibody, is intended to encompass direct labeling of the probe or antibody by coupling (i.e., physically linking) a detectable substance to the probe or antibody, as well as indirect labeling of the probe or antibody by reactivity with another reagent that is directly labeled. Examples of indirect labeling include detection of a primary antibody using a fluorescently labeled secondary antibody and end-labeling of a DNA probe with biotin such that it can be detected with fluorescently labeled streptavidin.

In another embodiment, the antibody is labeled, e.g., a radio-labeled, chromophore-labeled, fluorophore-labeled, or enzyme-labeled antibody. In another embodiment, an antibody derivative (e.g., an antibody conjugated with a substrate or with the protein or ligand of a protein-ligand pair {e.g., biotin-streptavidin}), or an antibody fragment (e.g., a single-chain antibody, an isolated antibody hypervariable domain, etc.) which binds specifically with a mutated protein, is used.

Mutated polypeptides from cells can be isolated using techniques that are known to those of skill in the art. The protein isolation methods employed can, for example, be such as those described in Harlow and Lane (Harlow and Lane, 1988, *Antibodies: A Laboratory Manual*, Cold Spring Harbor Laboratory Press, Cold Spring Harbor, New York).

Means of detecting proteins using electrophoretic techniques are well known to those of skill in the art (see generally, R. Scopes (1982) *Protein Purification*, Springer-Verlag, N.Y.; Deutscher, (1990) *Methods in Enzymology Vol. 182: Guide to Protein Purification*, Academic Press, Inc., N.Y.).

In another embodiment, Western blot (immunoblot) analysis is used to detect and quantify the presence of a polypeptide in the sample.

In another embodiment, the polypeptide is detected using an immunoassay. As used herein, an immunoassay is an assay that utilizes an antibody to specifically bind to the analyte. The immunoassay is thus characterized by detection of specific binding of a polypeptide to an anti-antibody as opposed to the use of other physical or chemical properties to isolate, target, and quantify the analyte.

The mutated polypeptide is detected and/or quantified using any of a number of immunological binding assays (see, e.g., U.S. Pat. Nos. 4,366,241; 4,376,110; 4,517,288; and 4,837,168). For a review of the general immunoassays, see also Asai (1993) *Methods in Cell Biology Volume 37: Antibodies in Cell Biology*, Academic Press, Inc. New York; Stites & Terr (1991) *Basic and Clinical Immunology* 7th Edition.

Kits

In one aspect, the invention features, a kit, e.g., containing an oligonucleotide having an alteration described herein, e.g., a HER2 mutation. Optionally, the kit can also contain an oligonucleotide that is the wildtype counterpart of the mutant oligonucleotide.

A kit can include a carrier, e.g., a means being compartmentalized to receive in close confinement one or more container means. In one embodiment the container contains an oligonucleotide, e.g., a primer or probe as described above. The components of the kit are useful, for example, to diagnose or identify a mutation in a tumor sample in a patient. The probe or primer of the kit can be used in any sequencing or nucleotide detection assay known in the art, e.g., a sequencing assay, e.g., an NGS method, RT-PCR, or in situ hybridization.

In some embodiments, the components of the kit are useful, for example, to diagnose or identify a mutation in a tumor sample in a patient, and to accordingly identify an appropriate therapeutic agent to treat the cancer.

A kit featured in the invention can include, e.g., assay positive and negative controls, nucleotides, enzymes (e.g., RNA or DNA polymerase or ligase), solvents or buffers, a stabilizer, a preservative, a secondary antibody, e.g., an anti-HRP antibody (IgG) and a detection reagent.

An oligonucleotide can be provided in any form, e.g., liquid, dried, semi-dried, or lyophilized, or in a form for storage in a frozen condition.

Typically, an oligonucleotide, and other components in a kit are provided in a form that is sterile. An oligonucleotide, e.g., an oligonucleotide that contains a mutation, described herein, or an oligonucleotide complementary to an alteration described herein, is provided in a liquid solution, the liquid solution generally is an aqueous solution, e.g., a sterile aqueous solution. When the oligonucleotide is provided as a dried form, reconstitution generally is accomplished by the addition of a suitable solvent. The solvent, e.g., sterile buffer, can optionally be provided in the kit.

The kit can include one or more containers for the composition containing an oligonucleotide in a concentration suitable for use in the assay or with instructions for dilution for use in the assay. In some embodiments, the kit contains separate containers, dividers or compartments for the oligonucleotide and assay components, and the informational material. For example, the oligonucleotides can be contained in a bottle or vial, and the informational material can be contained in a plastic sleeve or packet. In other embodiments, the separate elements of the kit are contained within a single, undivided container. For example, an oligonucleotide composition is contained in a bottle or vial that has attached thereto the informational material in the form of a label. In some embodiments, the kit includes a plurality (e.g., a pack) of individual containers, each containing one or more unit forms (e.g., for use with one assay) of an oligonucleotide. For example, the kit includes a plurality of ampoules, foil packets, or blister packs, each containing a single unit of oligonucleotide for use in sequencing or detecting a mutation in a tumor sample. The containers of the kits can be air tight and/or waterproof. The container can be labeled for use.

For antibody-based kits, the kit can include: (1) a first antibody (e.g., attached to a solid support) which binds to a mutated polypeptide; and, optionally, (2) a second, different antibody which binds to either the polypeptide or the first antibody and is conjugated to a detectable agent.

In one embodiment, the kit can include informational material for performing and interpreting the sequencing or diagnostic. In another embodiment, the kit can provide guidance as to where to report the results of the assay, e.g., to a treatment center or healthcare provider. The kit can include forms for reporting the results of a sequencing or diagnostic assay described herein, and address and contact information regarding where to send such forms or other related information; or a URL (Uniform Resource Locator) address for reporting the results in an online database or an online application (e.g., an app). In another embodiment, the informational material can include guidance regarding whether a patient should receive treatment with a particular chemotherapeutic drug, depending on the results of the assay.

The informational material of the kits is not limited in its form. In many cases, the informational material, e.g., instructions, is provided in printed matter, e.g., a printed text, drawings, and/or photographs, e.g., a label or printed sheet. However, the informational material can also be provided in other formats, such as computer readable material, video recording, or audio recording. In another embodiment, the informational material of the kit is contact information, e.g., a physical address, email address, website, or telephone number, where a user of the kit can obtain substantive information about the sequencing or diagnostic assay and/or its use in the methods described herein. The informational material can also be provided in any combination of formats.

In some embodiments, a biological sample is provided to an assay provider, e.g., a service provider (such as a third party facility) or a healthcare provider, who evaluates the sample in an assay and provides a read out. For example, in one embodiment, an assay provider receives a biological sample from a subject, such as a blood or tissue sample, e.g., a biopsy sample, and evaluates the sample using an assay described herein, e.g., a sequencing assay or in situ hybridization assay, and determines that the sample contains a mutation. The assay provider, e.g., a service provider or healthcare provider, can then conclude that the subject is, or is not, a candidate for a particular drug or a particular cancer treatment regimen.

Other embodiments of the invention include the following.

Nucleic Acid Molecules, Detection and Capturing Reagents

The invention also features an isolated nucleic acid molecule, or an isolated preparation of nucleic acid molecules, that includes an alteration described herein. Such nucleic acid molecules or preparations thereof can include an alteration described herein or can be used to detect, e.g., sequence, an alteration.

The invention also features a nucleic acid molecule, e.g., nucleic acid fragment, suitable as probe, primer, bait or library member that includes, flanks, hybridizes to, which are useful for identifying, or are otherwise based on, an alteration described herein. In certain embodiments, the probe, primer or bait molecule is an oligonucleotide that allows capture, detection or isolation of a nucleic acid molecule containing an alteration described herein, e.g., an alteration in ERBB2, e.g. a mutation in HER2 at residue S310 in which residue S310 mutated to S310F or S310Y; or a mutation at residue 157 of HER2.

The oligonucleotide can comprise a nucleotide sequence substantially complementary to nucleic acid molecules or fragments of nucleic acid molecules comprising an alteration described herein. The sequence identity between the nucleic acid molecule, e.g., the oligonucleotide, and the target sequence need not be exact, so long as the sequences are sufficiently complementary to allow the capture, detection or isolation of the target sequence. In one embodiment, the nucleic acid fragment is a probe or primer that includes an oligonucleotide between about 5 and 25, e.g., between 10 and 20, or 10 and 15 nucleotides in length. In other embodiments, the nucleic acid fragment is a bait that includes an oligonucleotide between about 100 to 300 nucleotides, 130 and 230 nucleotides, or 150 and 200 nucleotides, in length.

In one embodiment, the nucleic acid fragment can be used to identify or capture, e.g., by hybridization, a nucleic acid molecules comprising an alteration described herein, e.g., an alteration in HER2, e.g., a mutation in HER2 at residue S310 in which residue S310 mutated to S310F or S310Y; or a mutation at residue 157 of HER2. For example, the nucleic acid fragment can be a probe, a primer, or a bait, for use in identifying or capturing, e.g., by hybridization, an alteration described herein.

The probes or primers described herein can be used, for example, PCR amplification. In one exemplary embodiment where detection is based on PCR, amplification of the mutation can be performed using a primer or a primer pair, e.g., for amplifying a sequence flanking an alteration described herein.

In other embodiments, the nucleic acid fragment includes a bait that comprises a nucleotide sequence that hybridizes to a nucleic acid molecules comprising an alteration described herein, and thereby allows the capture or isolation said nucleic acid molecule. In one embodiment, a bait is suitable for solution phase hybridization. In other embodiments, a bait includes a binding entity, e.g., an affinity tag, that allows capture and separation, e.g., by binding to a binding entity, of a hybrid formed by a bait and a nucleic acid hybridized to the bait.

In other embodiments, the nucleic acid fragment includes a library member comprising a nucleic acid molecule described herein. In one embodiment, the library member includes a mutation, e.g., a base substitution, that results in an alteration described herein.

The nucleic acid fragment can be detectably labeled with, e.g., a radiolabel, a fluorescent label, a bioluminescent label, a chemiluminescent label, an enzyme label, a binding pair label, or can include an affinity tag; a tag, or identifier (e.g., an adaptor, barcode or other sequence identifier).

Polypeptides

In another aspect, the disclosure features a polypeptide comprising an alteration described herein (e.g., a purified polypeptide comprising an alteration described herein), a biologically active or antigenic fragment thereof, as well as reagents (e.g., antibody molecules that bind to a polypeptide comprising an alteration described herein), methods for modulating the activity of a polypeptide comprising an alteration described herein and detection of a polypeptide comprising an alteration described herein.

In another embodiment, the polypeptide or fragment is a peptide, e.g., an immunogenic peptide or protein that contains an alteration described herein. Such immunogenic peptides or proteins can be used to raise antibodies specific to the polypeptide or protein comprising an alteration described herein. In other embodiments, such immunogenic peptides or proteins can be used for vaccine preparation. The vaccine preparation can include other components, e.g., an adjuvant.

In another aspect, the invention features antibody molecules that bind to a polypeptide comprising an alteration described herein or fragment described herein. In embodiments the antibody can distinguish wild type from the mutated polypeptide, e.g., the polypeptide comprising an alteration described herein. Techniques for generating antibody molecules are known in the art, and are described, for example, in WO 2012/092426, entitled "Optimization of Multigene Analysis of Tumor Samples, incorporated herein by reference.

Detection Reagents

In another aspect, the invention features a detection reagent, e.g., a purified or an isolated preparation thereof. Detection reagents can distinguish a nucleic acid, or protein sequence, having an alteration described herein, e.g., of a nucleic acid molecule comprising an alteration described herein, e.g., an alteration in ERBB2; an alteration in HER2, e.g. a mutation in HER2 at residue S310 in which residue S310 is mutated to S310F or S310Y.

Detection reagents, e.g., nucleic acid-based detection reagents, can be used to identify mutations in a target nucleic acid, e.g., DNA, e.g., genomic DNA or cDNA, or RNA, e.g., in a sample, e.g., a sample of nucleic acid derived from a urothelial and/or micropapillary carcinoma, e.g., MPUC. Detection reagents, e.g., antibody-based detection reagents, can be used to identify mutations in a target protein, e.g., in a sample, e.g., a sample of protein derived from, or produced by, a urothelial and/or micropapillary carcinoma cell, e.g., MPUC cell.

Nucleic Acid-Based Detection Reagents

In one embodiment, the detection reagent comprises a nucleic acid molecule, e.g., a DNA, RNA or mixed DNA/RNA molecule, comprising sequence which is complementary with a nucleic acid sequence on a target nucleic acid (the sequence on the target nucleic acid that is bound by the detection reagent is referred to herein as the "detection reagent binding site" and the portion of the detection reagent that corresponds to the detection reagent binding site is referred to as the "target binding site"). In one embodiment, the detection reagent binding site is disposed in relationship to the interrogation position such that binding (or in embodiments, lack of binding) of the detection reagent to the detection reagent binding site allows differentiation of mutant and reference sequences for a mutant described herein (nucleic acid molecule comprising an alteration described herein, e.g., an alteration in ERBB2; an alteration in HER2, e.g. a mutation in HER2 at residue S310 in which residue S310 is mutated to S310F or S310Y, or a mutation at residue 157 of HER2, from a reference sequence. The detection reagent can be modified, e.g., with a label or other moiety, e.g., a moiety that allows capture.

In one embodiment, the detection reagent comprises a nucleic acid molecule, e.g., a DNA, RNA or mixed DNA/RNA molecule, which, e.g., in its target binding site, includes the interrogation position and which can distinguish (e.g., by affinity of binding of the detection reagent to a target nucleic acid or the ability for a reaction, e.g., a ligation or extension reaction with the detection reagent) between a mutation, e.g., a translocation described herein, and a reference sequence. In embodiments, the interrogation position can correspond to a terminal, e.g., to a 3' or 5' terminal nucleotide, a nucleotide immediately adjacent to a 3' or 5' terminal nucleotide, or to another internal nucleotide, of the detection reagent or target binding site.

In embodiments, the difference in the affinity of the detection reagent for a target nucleic acid comprising the alteration described herein and that for a target nucleic acid comprising the reference sequence allows determination of the presence or absence of the mutation (or reference) sequence. Typically, such detection reagents, under assay conditions, will exhibit substantially higher levels of binding only to the mutant or only to the reference sequence, e.g., will exhibit substantial levels of binding only to the mutation or only to the reference sequence.

In embodiments, binding allows (or inhibits) a subsequent reaction, e.g., a subsequent reaction involving the detection reagent or the target nucleic acid. E.g., binding can allow ligation, or the addition of one or more nucleotides to a nucleic acid, e.g., the detection reagent, e.g., by DNA polymerase, which can be detected and used to distinguish mutant from reference. In embodiments, the interrogation position is located at the terminus, or sufficiently close to the terminus, of the detection reagent or its target binding site, such that hybridization, or a chemical reaction, e.g., the addition of one or more nucleotides to the detection reagent, e.g., by DNA polymerase, only occurs, or occurs at a substantially higher rate, when there is a perfect match between the detection reagent and the target nucleic acid at the interrogation position or at a nucleotide position within 1, 2, or 3 nucleotides of the interrogation position.

In one embodiment, the detection reagent comprises a nucleic acid, e.g., a DNA, RNA or mixed DNA/RNA molecule wherein the molecule, or its target binding site, is adjacent (or flanks), e.g., directly adjacent, to the interrogation position, and which can distinguish between a mutation described herein, and a reference sequence, in a target nucleic acid.

In embodiments, the detection reagent binding site is adjacent to the interrogation position, e.g., the 5' or 3'terminal nucleotide of the detection reagent, or its target binding site, is adjacent, e.g., between 0 (directly adjacent) and 1,000, 500, 400, 200, 100, 50, 10, 5, 4, 3, 2, or 1 nucleotides from the interrogation position. In embodiments, the outcome of a reaction will vary with the identity of the nucleotide at the interrogation position allowing one to distinguish between mutant and reference sequences. E.g., in the presence of a first nucleotide at the interrogation position a first reaction will be favored over a second reaction. E.g., in a ligation or primer extension reaction, the product will differ, e.g., in charge, sequence, size, or susceptibility to a further reaction (e.g., restriction cleavage) depending on the identity of the nucleotide at the interrogation position. In embodiments the detection reagent comprises paired molecules (e.g., forward and reverse primers), allowing for amplification, e.g., by PCR amplification, of a duplex containing the interrogation position. In such embodiments, the presence of the mutation can be determined by a difference in the property of the amplification product, e.g., size, sequence, charge, or susceptibility to a reaction, resulting from a sequence comprising the interrogation position and a corresponding sequence having a reference nucleotide at the interrogation positions. In embodiments, the presence or absence of a characteristic amplification product is indicative of the identity of the nucleotide at the interrogation site and thus allows detection of the mutation.

In embodiments, the detection reagent, or its target binding site, is directly adjacent to the interrogation position, e.g., the 5' or 3'terminal nucleotide of the detection reagent is directly adjacent to the interrogation position. In embodiments, the identity of the nucleotide at the interrogation position will determine the nature of a reaction, e.g., a reaction involving the detection reagent, e.g., the modification of one end of the detection reagent. E.g., in the presence of a first nucleotide at the interrogation position a first reaction will be favored over a second reaction. By way of example, the presence of a first nucleotide at the interrogation position, e.g., a nucleotide associated with a mutation, can promote a first reaction, e.g., the addition of a complementary nucleotide to the detection reagent. By way of example, the presence of an A at the interrogation position will cause the incorporation of a T, having, e.g., a first colorimetric label, while the presence of a G and the interrogation position will cause the incorporation for a C, having, e.g., a second colorimetric label. In one embodiment, the presence of a first nucleotide at the nucleotide will result in ligation of the detection reagent to a second nucleic acid. E.g., a third nucleic acid can be hybridized to the target nucleic acid sufficiently close to the interrogation site that if the third nucleic acid has an exact match at the interrogation site it will be ligated to the detection reagent. Detection of the ligation product, or its absence, is indicative of the identity of the nucleotide at the interrogation site and thus allows detection of the mutation.

A variety of readouts can be employed. E.g., binding of the detection reagent to the mutant or reference sequence can be followed by a moiety, e.g., a label, associated with the detection reagent, e.g., a radioactive or enzymatic label. In embodiments the label comprises a quenching agent and a signaling agent and hybridization results in altering the distance between those two elements, e.g., increasing the distance and un-quenching the signaling agent. In embodiments, the detection reagent can include a moiety that allows separation from other components of a reaction mixture. In embodiments, binding allows cleavage of the bound detection reagent, e.g., by an enzyme, e.g., by the nuclease activity of the DNA polymerase or by a restriction enzyme. The cleavage can be detected by the appearance or disappearance of a nucleic acid or by the separation of a quenching agent and a signaling agent associated with the detection reagent. In embodiments, binding protects, or renders the target susceptible, to further chemical reaction, e.g., labeling or degradation, e.g., by restriction enzymes. In embodiments binding with the detection reagent allows capture separation or physical manipulation of the target nucleic acid to thereby allow for identification. In embodiments binding can result in a detectable localization of the detection reagent or target, e.g., binding could capture the target nucleic acid or displace a third nucleic acid. Binding can allow for the extension or other size change in a component, e.g., the detection reagent, allowing distinction between mutant and reference sequences. Binding can allow for the production, e.g., by PCR, of an amplicon that distinguishes mutant from reference sequence.

In one embodiment the detection reagent, or the target binding site, is between 5 and 500, 5 and 300, 5 and 250, 5 and 200, 5 and 150, 5 and 100, 5 and 50, 5 and 25, 5 and 20, 5 and 15, or 5 and 10 nucleotides in length. In one embodiment the detection reagent, or the target binding site, is between 10 and 500, 10 and 300, 10 and 250, 10 and 200, 10 and 150, 10 and 100, 10 and 50, 10 and 25, 10 and 20, or 10 and 15, nucleotides in length. In one embodiment the detection reagent, or the target binding site, is between 20 and 500, 20 and 300, 20 and 250, 20 and 200, 20 and 150, 20 and 100, 20 and 50, or 20 and 25 nucleotides in length. In one embodiment the detection reagent, or the target binding site, is sufficiently long to distinguish between mutant and reference sequences and is less than 100, 200, 300, 400, or 500 nucleotides in length.

Preparations of Nucleic Acids and Uses Thereof

In another aspect, the invention features purified or isolated preparations of a neoplastic or tumor cell nucleic acid, e.g., DNA, e.g., genomic DNA or cDNA, or RNA, containing an interrogation position described herein, useful for determining if a mutation disclosed herein is present. The nucleic acid includes the interrogation position, and typically additional sequence on one or both sides of the interrogation position. In addition the nucleic acid can contain heterologous sequences, e.g., adaptor or priming sequences, typically attached to one or both terminus of the nucleic acid. The nucleic acid also includes a label or other moiety, e.g., a moiety that allows separation or localization.

In embodiments, the nucleic acid is between 20 and 1,000, 30 and 900, 40 and 800, 50 and 700, 60 and 600, 70 and 500, 80 and 400, 90 and 300, or 100 and 200 nucleotides in length (with or without heterologous sequences). In one embodiment, the nucleic acid is between 40 and 1,000, 50 and 900, 60 and 800, 70 and 700, 80 and 600, 90 and 500, 100 and 400, 110 and 300, or 120 and 200 nucleotides in length (with or without heterologous sequences). In another embodiment, the nucleic acid is between 50 and 1,000, 50 and 900, 50 and 800, 50 and 700, 50 and 600, 50 and 500, 50 and 400, 50 and 300, or 50 and 200 nucleotides in length (with or without heterologous sequences). In embodiments, the nucleic acid is of sufficient length to allow sequencing (e.g., by chemical sequencing or by determining a difference in $T_m$ between mutant and reference preparations) but is optionally less than 100, 200, 300, 400, or 500 nucleotides in length (with or without heterologous sequences).

Such preparations can be used to sequence nucleic acid from a sample, e.g., a neoplastic or tumor sample. In one embodiment the purified preparation is provided by in situ amplification of a nucleic acid provided on a substrate. In embodiments the purified preparation is spatially distinct from other nucleic acids, e.g., other amplified nucleic acids, on a substrate.

In one embodiment, the purified or isolated preparation of nucleic acid is derived from a urothelial and/or micropapillary carcinoma, e.g., MPUC.

Such preparations can be used to determine if a sample comprises mutant sequence, e.g., an alteration described herein.

In another aspect, the invention features, a method of determining the sequence of an interrogation position for an alteration described herein, comprising:

providing a purified or isolated preparations of nucleic acid, e.g., DNA, e.g., genomic DNA or cDNA, or RNA, containing an interrogation position described herein, sequencing, by a method that breaks or forms a chemical bond, e.g., a covalent or non-covalent chemical bond, e.g., in a detection reagent or a target sequence, the nucleic acid so as to determine the identity of the nucleotide at an interrogation position. The method allows determining if an alteration described herein is present.

In one embodiment, sequencing comprises contacting the nucleic acid comprising an alteration described herein with a detection reagent described herein.

In one embodiment, sequencing comprises determining a physical property, e.g., stability of a duplex form of the nucleic acid comprising an alteration described herein, e.g., $T_m$, that can distinguish mutant from reference sequence.

In one embodiment, the nucleic acid comprising an alteration described herein is derived from a urothelial and/or micropapillary carcinoma, e.g., MPUC.

Reaction Mixtures and Devices

In another aspect, the invention features, purified or isolated preparations of a nucleic acid, e.g., DNA, e.g., genomic DNA or cDNA, or RNA, containing an interrogation position described herein, useful for determining if a mutation disclosed herein is present, disposed in sequencing device, or a sample holder for use in such a device. In one embodiment, the nucleic acid is derived from a urothelial and/or micropapillary carcinoma, e.g., MPUC.

In another aspect, the invention features, purified or isolated preparations of a nucleic acid, e.g., DNA, e.g., genomic DNA or cDNA, or RNA, containing an interrogation position described herein, useful for determining if a mutation disclosed herein is present, disposed in a device for determining a physical or chemical property, e.g., stability of a duplex, e.g., $T_m$ or a sample holder for use in such a device. In one embodiment, the device is a calorimeter. In one embodiment the nucleic acid comprising an alteration described herein is derived from a urothelial and/or micropapillary carcinoma, e.g., MPUC.

The detection reagents described herein can be used to determine if an alteration described herein is present in a sample. In embodiments, the sample comprises a nucleic acid that is derived from a micropapillary carcinoma, e.g., MPUC. The cell can be from a neoplastic or a tumor sample, e.g., a biopsy taken from the neoplasm or the tumor; from circulating tumor cells, e.g., from peripheral blood; or from a blood or plasma sample. In one embodiment, the nucleic acid is derived from a urothelial and/or micropapillary carcinoma, e.g., MPUC.

Accordingly, in one aspect, the invention features a method of making a reaction mixture, comprising:

combining a detection reagent, or purified or isolated preparation thereof, described herein with a target nucleic acid derived from a urothelial and/or micropapillary carcinoma, e.g., MPUC, which comprises a sequence having an interrogation position for an alteration described herein.

In another aspect, the invention features a reaction mixture, comprising:

a detection reagent, or purified or isolated preparation thereof, described herein; and a target nucleic acid derived from a urothelial and/or micropapillary carcinoma cell, e.g., a MPUC cell, which comprises a sequence having an interrogation position for an alteration described herein.

In one embodiment of the reaction mixture, or the method of making the reaction mixture:

the detection reagent comprises a nucleic acid, e.g., a DNA, RNA or mixed DNA/RNA, molecule which is complementary with a nucleic acid sequence on a target nucleic acid (the detection reagent binding site) wherein the detection reagent binding site is disposed in relationship to the interrogation position such that binding of the detection reagent to the detection reagent binding site allows differentiation of mutant and reference sequences for a mutation sequence or event described herein.

In one embodiment of the reaction mixture, or the method of making the reaction mixture: the target nucleic acid sequence is derived from a urothelial and/or micropapillary carcinoma, e.g., MPUC, as described herein. In one embodiment of the reaction mixture, or the method of making the reaction mixture: the mutation is an alteration described herein, including: a substitution, e.g., a substitution described herein.

An alteration described herein, can be distinguished from a reference, e.g., a non-mutant or wildtype sequence, by reaction with an enzyme that reacts differentially with the mutation and the reference. E.g., they can be distinguished by cleavage with a restriction enzyme that has differing activity for the mutant and reference sequences. E.g., the invention includes a method of contacting a nucleic acid comprising an alteration described herein with such an enzyme and determining if a product of that cleavage which can distinguish mutant form reference sequence is present.

In one aspect the inventions provides, a purified preparation of a restriction enzyme cleavage product which can distinguish between mutant and reference sequence, wherein one end of the cleavage product is defined by an enzyme that cleaves differentially between mutant and reference sequence. In one embodiment, the cleavage product includes the interrogation position.

Protein-Based Detection Reagents, Methods, Reaction Mixtures and Devices

A mutant protein described herein can be distinguished from a reference, e.g., a non-mutant or wild-type protein, by reaction with a reagent, e.g., a substrate, e.g., a substrate for catalytic activity or functional activity, or an antibody, that reacts differentially with the mutant and reference protein. In one aspect, the invention includes a method of contacting a sample comprising a mutant protein described herein with such reagent and determining if the mutant protein is present in the sample.

In another embodiment, the invention features, an antibody that can distinguish a mutant protein described herein, or a fragment thereof, from a reference, e.g., a non-mutant or wild type protein.

Accordingly, in one aspect, the invention features a method of making a reaction mixture comprising:

combining a detection reagent, or purified or isolated preparation thereof, e.g., a substrate, e.g., a substrate for phosphorylation or other activity, or an antibody, described herein with a target protein derived from a urothelial and/or micropapillary carcinoma cell, e.g., MPUC cell, which comprises a sequence having an interrogation position for an alteration described herein.

In another aspect, the invention features, a reaction mixture comprising:

a detection reagent, or purified or isolated preparation thereof, e.g., a substrate, e.g., a substrate for phosphorylation or other activity, or an antibody, described herein; and a target protein derived from a urothelial and/or micropapillary carcinoma cell, e.g., MPUC cell, which comprises a sequence having an interrogation position for an alteration described herein.

In one embodiment of the reaction mixture, or the method of making the reaction mixture:

the detection reagent comprises an antibody specific for a mutant protein described herein.

In one embodiment of the reaction mixture, or the method of making the reaction mixture that includes a urothelial and/or micropapillary carcinoma cell, e.g., MPUC cell.

In one embodiment of the reaction mixture, or the method of making the reaction mixture: the mutation is an alteration described herein (e.g., a HER2 mutation described herein).

Screening Methods

In another aspect, the invention features a method, or assay, for screening for agents that modulate, e.g., inhibit, the expression or activity of a nucleic acid or polypeptide or protein comprising a mutation as described herein. The method includes contacting a nucleic acid or polypeptide or protein comprising an alteration described herein, or a cell expressing a nucleic acid or polypeptide or protein comprising an alteration described herein, with a candidate agent; and detecting a change in a parameter associated with a nucleic acid or polypeptide or protein comprising an alteration described herein, e.g., a change in the expression or an activity of the nucleic acid or polypeptide or protein comprising an alteration described herein. The method can, optionally, include comparing the treated parameter to a reference value, e.g., a control sample (e.g., comparing a parameter obtained from a sample with the candidate agent to a parameter obtained from a sample without the candidate agent). In one embodiment, if a decrease in expression or activity of the nucleic acid or polypeptide or protein comprising an alteration described herein is detected, the candidate agent is identified as an inhibitor. In another embodiment, if an increase in expression or activity of the nucleic acid or polypeptide or protein comprising an alteration described herein is detected, the candidate agent is identified as an activator.

In one embodiment, the contacting step is effected in a cell-free system, e.g., a cell lysate or in a reconstituted system. In other embodiments, the contacting step is effected in a cell in culture, e.g., a cell expressing an alteration described herein (e.g., a mammalian cell, a tumor cell or cell line, a recombinant cell). In yet other embodiments, the contacting step is effected in a cell in vivo (a-expressing cell present in a subject, e.g., an animal subject (e.g., an in vivo animal model).

Exemplary parameters evaluated include one or more of:

(i) a change in binding activity, e.g., direct binding of the candidate agent to a polypeptide comprising an alteration described herein; a binding competition between a known ligand and the candidate agent to a polypeptide comprising an alteration described herein;

(ii) a change in kinase activity, e.g., phosphorylation levels of a polypeptide comprising an alteration described herein (e.g., an increased or decreased autophosphorylation); or a change in a target of a polypeptide comprising an alteration described herein, In certain embodiments, a change in kinase activity, e.g., phosphorylation, is detected by any of Western blot (e.g., using an antibody which binds to a polypeptide comprising an alteration described herein, mass spectrometry, immunoprecipitation, immunohistochemistry, immunomagnetic beads, among others;

(iii) a change in an activity of a cell containing a tumor cell or a recombinant cell, e.g., a change in proliferation, morphology or tumorigenicity of the cell;

(iv) a change in tumor present in an animal subject, e.g., size, appearance, proliferation, of the tumor; or (v) a change in the level, e.g., expression level, of a nucleic acid or polypeptide or protein comprising an alteration described herein.

In one embodiment, a change in a cell free assay in the presence of a candidate agent is evaluated. For example, an activity of a nucleic acid or polypeptide or protein comprising an alteration described herein, or interaction of a nucleic acid or polypeptide or protein comprising an alteration described herein with a downstream ligand can be detected. In one embodiment, the polypeptide or protein comprising an alteration described herein is contacted with a ligand, e.g., in solution, and a candidate agent is monitored for an ability to modulate, e.g., inhibit, an interaction, e.g., binding, between the nucleic acid or polypeptide or protein comprising an alteration described herein and the ligand.

In other embodiments, a change in an activity of a cell is detected in a cell in culture, e.g., a cell expressing a mutation (e.g., a mammalian cell, a tumor cell or cell line, a recombinant cell). In one embodiment, the cell is a recombinant cell that is modified to express a nucleic acid comprising an alteration described herein, e.g., is a recombinant cell transfected with a nucleic acid comprising an alteration described herein. The transfected cell can show a change in response to the expressed mutation, e.g., increased proliferation, changes in morphology, increased tumorigenicity, and/or acquired a transformed phenotype. A change in any of the activities of the cell, e.g., the recombinant cell, in the presence of the candidate agent can be detected. For example, a decrease in one or more of: proliferation, tumorigenicity, transformed morphology, in the presence of the candidate agent can be indicative of an inhibitor of a nucleic acid or polypeptide or protein comprising an alteration described herein. In other embodiments, a change in binding activity or phosphorylation as described herein is detected.

In yet other embodiment, a change in a tumor present in an animal subject (e.g., an in vivo animal model) is detected. In one embodiment, the animal model is a tumor containing animal or a xenograft comprising cells expressing a nucleic acid or polypeptide or protein comprising an alteration described herein (e.g., tumorigenic cells expressing a nucleic acid or polypeptide or protein comprising an alteration described herein). The candidate agent can be administered to the animal subject and a change in the tumor is detected. In one embodiment, the change in the tumor includes one or more of a tumor growth, tumor size, tumor burden, survival, is evaluated. A decrease in one or more of tumor growth, tumor size, tumor burden, or an increased survival is indicative that the candidate agent is an inhibitor.

In other embodiments, a change in expression of a nucleic acid or polypeptide or protein comprising an alteration described herein can be monitored by detecting the nucleic acid or protein levels, e.g., using the methods described herein.

In certain embodiments, the screening methods described herein can be repeated and/or combined. In one embodiment, a candidate agent that is evaluated in a cell-free or cell-based described herein can be further tested in an animal subject.

In one embodiment, the candidate agent is a small molecule compound, e.g., a kinase inhibitor, a nucleic acid (e.g., antisense, siRNA, aptamer, ribozymes, microRNA), an antibody molecule (e.g., a full antibody or antigen binding fragment thereof that binds to the mutation). The candidate agent can be obtained from a library (e.g., a commercial library of kinase inhibitors) or rationally designed.

In other embodiments, the method, or assay, includes providing a step based on proximity-dependent signal generation, e.g., a two-hybrid assay that includes a first mutation protein (e.g., a mutated protein), and a second mutated protein (e.g., a ligand), contacting the two-hybrid assay with a test compound, under conditions wherein said two hybrid assay detects a change in the formation and/or stability of the complex, e.g., the formation of the complex initiates transcription activation of a reporter gene.

In one non-limiting example, the three-dimensional structure of the active site of a polypeptide or protein comprising an alteration described herein is determined by crystallizing the complex formed by the polypeptide or protein and a known inhibitor. Rational drug design is then used to identify new test agents by making alterations in the structure of a known inhibitor or by designing small molecule compounds that bind to the active site of the polypeptide or protein.

The candidate agents can be obtained using any of the numerous approaches in combinatorial library methods known in the art, including: biological libraries; peptoid libraries (libraries of molecules having the functionalities of peptides, but with a novel, non-peptide backbone which are resistant to enzymatic degradation but which nevertheless remain bioactive; see, e.g., Zuckermann, R. N. et al. (1994) *J. Med. Chem.* 37:2678-85); spatially addressable parallel solid phase or solution phase libraries; synthetic library methods requiring deconvolution; the 'one-bead one-compound' library method; and synthetic library methods using affinity chromatography selection. The biological library and peptoid library approaches are limited to peptide libraries, while the other four approaches are applicable to peptide, non-peptide oligomer or small molecule libraries of compounds (Lam (1997) *Anticancer Drug Des.* 12:145).

Examples of methods for the synthesis of molecular libraries can be found in the art, for example in: DeWitt et al. (1993) *Proc. Natl. Acad. Sci. U.S.A.* 90:6909; Erb et al. (1994) *Proc. Natl. Acad. Sci. USA* 91:11422; Zuckermann et al. (1994). *J. Med. Chem.* 37:2678; Cho et al. (1993) *Science* 261:1303; Carrell et al. (1994) *Angew. Chem. Int. Ed. Engl.* 33:2059; Carell et al. (1994) *Angew. Chem. Int. Ed. Engl.* 33:2061; and Gallop et al. (1994) *J. Med. Chem.* 37:1233.

Libraries of compounds may be presented in solution (e.g., Houghten (1992) *Biotechniques* 13:412-421), or on beads (Lam (1991) *Nature* 354:82-84), chips (Fodor (1993) *Nature* 364:555-556), bacteria (Ladner, U.S. Pat. No. 5,223,409), spores (Ladner U.S. Pat. No. 5,223,409), plasmids (Cull et al. (1992) *Proc Natl Acad Sci USA* 89:1865-1869) or on phage (Scott and Smith (1990) *Science* 249:386-390; Devlin (1990) *Science* 249:404-406; Cwirla et al. (1990) *Proc. Natl. Acad. Sci.* 87:6378-6382; Felici (1991) *J. Mol. Biol.* 222:301-310; Ladner supra.).

The interaction between two molecules can also be detected, e.g., using fluorescence energy transfer (FET) (see, for example, Lakowicz et al., U.S. Pat. No. 5,631,169; Stavrianopoulos, et al., U.S. Pat. No. 4,868,103). An FET binding event can be conveniently measured through standard fluorometric detection means known in the art (e.g., using a fluorimeter).

In another embodiment, determining the ability of the mutated protein to bind to a target molecule can be accomplished using real-time Biomolecular Interaction Analysis (BIA) (see, e.g., Sjolander, S. and Urbaniczky, C. (1991) *Anal. Chem.* 63:2338-2345 and Szabo et al. (1995) *Curr. Opin. Struct. Biol.* 5:699-705). "Surface plasmon resonance" or "BIA" detects biospecific interactions in real time, without labeling any of the interactants (e.g., BIAcore). Changes in the mass at the binding surface (indicative of a binding event) result in alterations of the refractive index of light near the surface (the optical phenomenon of surface plasmon resonance (SPR)), resulting in a detectable signal which can be used as an indication of real-time reactions between biological molecules.

EXAMPLES

Example 1

An Activating Extracellular Domain ERBB2 (HER2) Mutation in Urothelial Carcinoma (UC)

This example describes the results from a study of 35 UC which included a subset of cases used in Example 2. Experimental conditions are as described in Example 2. A single ERBB2 mutation in the only MPUC case profiled is described.

In this study, the UC in a 71-year-old female patient with stage IV high grade UC, an S310F external domain mutation in the ERBB2 gene was identified. This is the first reported mutation of ERBB2 in UC. The histology is taken from the lymph node metastasis specimen used for the NGS assessment. Note that this tumor has a micropapillary architecture. This UC features the S310F base substitution in the ERBB2 (HER2) gene. This tumor also featured mutations in the FBXW7 and TP53 genes.

Recent in vitro data suggest that ERBB2 S310F is an activating mutation, which is sensitive to irreversible dual Egfr/Erbb2 inhibitors (Greulich H (2010) *Cancer Res.* 1:1200-1210). ERBB2 mutations have not been previously reported in urothelial carcinoma (COSMIC, PubMed, August 2012), yet suggesting sensitivity to Her2-targeted drug therapies.

Example 2

A High Frequency of Activating Extracellular Domain ERBB2 (HER2) Mutation in Micropapillary Urothelial Carcinoma In this example, a genomic analysis was conducted of a series of patients with MPUC and an expanded series of non-MPUC to characterize the genomic landscape of MUPC and to identify targeted treatment options for patients diagnosed with this disease.

Methods

Targeted next generation sequencing (NGS) was performed on hybridization-captured, adaptor ligation based libraries using DNA extracted from 4 formalin-fixed paraffin embedded sections cut at 10 microns from 15 cases of MPUC and 64 cases of non-MUPC in a CLIA-certified lab (Foundation Medicine). The pathologic diagnosis of each case was confirmed on routine hematoxylin and eosin stained slides and all samples forwarded for DNA extraction contained a minimum of 20% DNA derived from tumor cells. All MPUC were histologically confirmed used published criteria (Sangoi A R, et al. (2010) *Am J Surg Pathol.* 34:1367-76) by 3 pathologists. DNA sequencing was performed for 3,230 exons of 182 cancer-related genes and 37 introns of 14 genes frequently rearranged in cancer (1.14 million total bps) on indexed, adaptor ligated, hybridization-captured (Agilent SureSelect custom kit) and fully sequenced using 49 bp paired reads on the Illumina HiSeq 2000. The MPUC cases were sequenced to at an average depth of 978X. The non-MP UC were sequenced to an average depth of 969X. All samples were evaluated for genomic alterations including base substitutions, insertions, deletions, copy number alterations (amplifications and homozygous deletions), and select gene fusions/rearrangements as previously described (Lipson D, et al. (2012) *Nat Med.* 18:382-4).

The bioinformatics processes used in this study included Bayesian algorithms to detect base substitutions, local assembly algorithms to detect short insertions and deletions, a comparison with process-matched normal control samples to detect gene copy number alterations and an analysis of chimeric read pairs to identify gene fusions. Actionable GA were defined as being linked to commercially available targeted therapies on the market or to targeted therapies being tested registered clinical trials. The 10 MPUC cases tested for HER2 (ERBB2) protein overexpression by immunohistochemistry (IHC) using the Dako Herceptest assay.

Results

Figure 1:
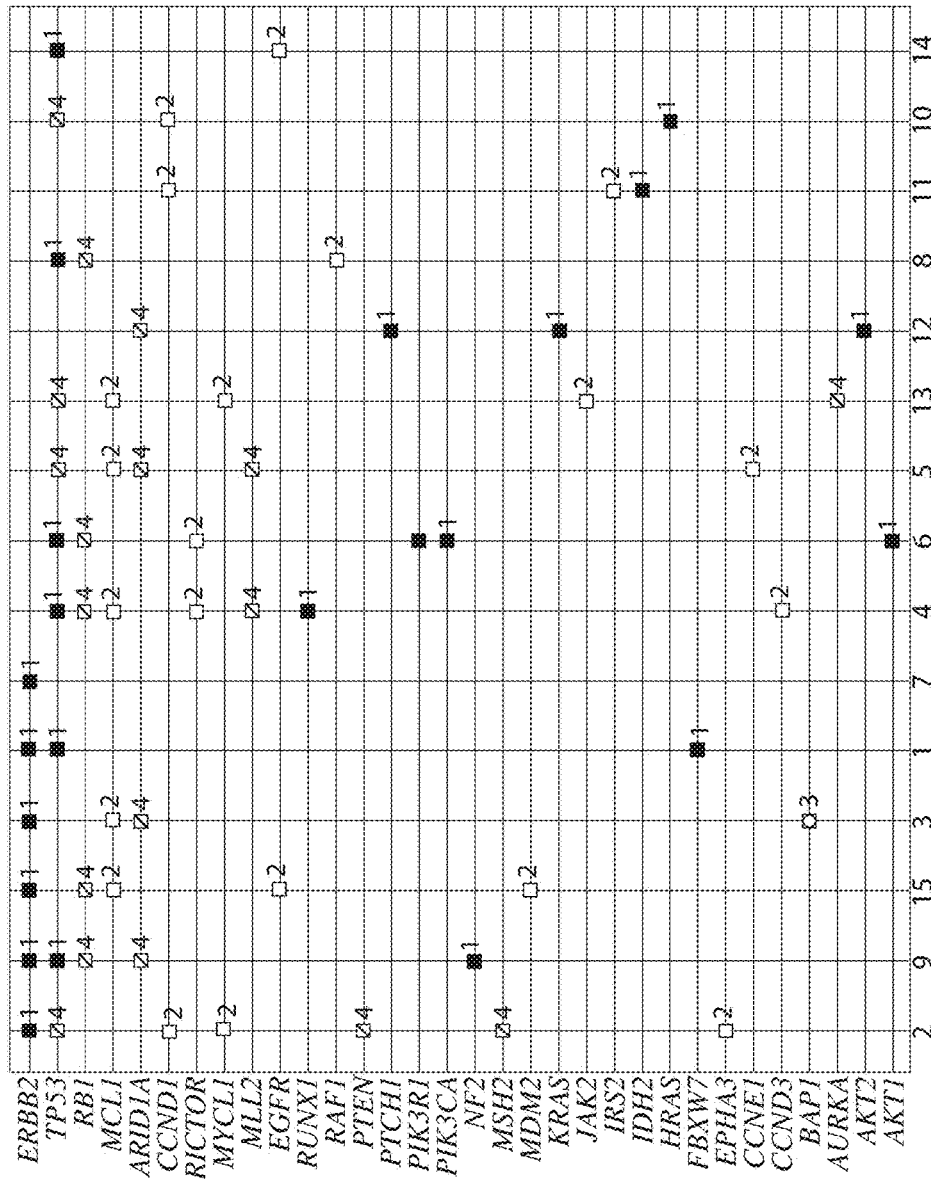
FIG. 1 depicts a tile plot of genomic alterations in 15 cases of micropapillary urothelial carcinoma.

The 15 MPUC samples were obtained from 10 male (66%) and 5 female (33%) patients with a mean age of 66 years (range 55 to 86 years). Sequencing was performed on the primary tumor in 11 (73%) cases (6 TURBT samples and 5 cystectomies) and on metastatic lesions in 4 (27%) of cases. All tumors were high grade, 3 cases were stage I, 3 were stage II, 2 were stage III and 7 were stage IV. A total of 67 genomic alterations (GA) (average 4.47 GA per tumor) were identified including alterations in TP53 (10 cases, 67%), ERBB2 (6 cases, 40%), MCL1 (5 cases, 33%), RB1 (5 cases, 33%), and ARID1A (4 cases, 27%) (FIG. 1 and FIG. 2). The 6 ERBB2 mutations were all located within the extracellular domain of ERBB2 including S310F (4 cases), S310Y (1 case) and R157W (1 case) (FIG. 2; FIG. 5). No mutations in the ERBB2 tyrosine kinase domain were observed. All 6 cases of MPUC with ERBB2 mutation were negative for ERBB2 amplification and in the 3 cases where additional tissue was available for testing, these ERBB2 mutated MPUC were also negative for HER2 over-expression by immunohistochemistry (IHC) (FIG. 2; FIG. 5).

In contrast, only 6/64 (9.4%) of non-MP UC harbored ERBB2 alterations including S310F mutations (3 cases), amplification (2 cases, 40 and 15 copies) and an ERBB2-GRB7 fusion (1 case) (FIG. 4; FIG. 6). The ERBB2 mutation frequency observed in both the MPUC and non-MPUC cohorts are higher than the 2/159 (1.3%) of protein changing ERBB2 mutations reported in urinary tract cancer in COSMIC (15). The enrichment of ERBB2 alterations in MPUC compared to non-MP UC is significant between this series (p<0.0084) and for all types of urinary tract cancer in COSMIC (p<0.001). All 9 ERBB2 WT MPUC cases harbored at least 1 actionable alteration, including alterations in AKT1, AKT2, CCND1, EGFR, PIK3CA, PIK3R1 and RAF1. The most frequent alterations in the non-MPUC group involved mutations in TP53 (38 total; 58% of non-MPUC cases) and CDKN2A/B (25 total; 39% of non-MPUC cases). Alterations in chromatin remodeling genes including truncating mutations in KDM6A (17 total; 27% of non-MPUC cases) and ARID1A (12 total; 19% of non-MPUC cases) were notable in the non-MPUC group (FIG. 4; FIG. 6).

DISCUSSION

MPUC is a relatively rare subtype of UC which comprises approximately 3,000 to 4,000 new cases diagnosed each year in the US, a an incidence just below that of the successfully targeted disease, chronic myelogenous leukemia (Amin M B, et al. (1994) *Am J Surg Pathol.* 18:1224-32); Sangoi A R, et al. (2010) *Am J Surg Pathol.* 34:1367-76; Kamat A M, et al. (2007) *Cancer.* 110:62-7; López J I, et al. (1999) *Histopathology* 34:561-2). MUPC is widely considered to have an adverse prognosis reflected in the propensity to invade lymphovascular spaces and spread to distant sites early in the course of the disease (Amin M B, et al. (1994) supra); Sangoi A R, et al. (2010) supra; Kamat A M, et al. (2007); López J I, et al. (1999) supra). Any component of MPUC in a UC of the bladder is considered to be significant and studies have shown that, as the proportion of the MPUC component increases, the prognosis worsens (Amin, M D. (2009) *Modern Pathol.* 22:S96-S118; Samaratunga H, et al. (2004) *Histopathol.* 45: 55-64; Stewart S L, et al. (2004) *MMWR Surveill Summ.* 53:1-108). Since MPUC is well-known to metastasize even when local invasion of the bladder muscle wall is absent, early radical surgery has been recommended for MPUC in comparison with conventional non-MP UC (Kamat A M, et al. (2007) supra.

In the present example, the significant enrichment of ERBB2 mutation frequency observed in MPUC (40%) versus non-MPUC (9.4%) was observed (p<0.0084). When compared with the COSMIC database which contains only 2 (1.4%) protein altering mutations in ERBB2 in 158 carcinomas of the urinary bladder (COSMIC v65 Release". *Catalogue Of Somatic Mutations In Cancer.* Wellcome Trust Sanger Institute. Retrieved 1 Jul. 2013 (http://www.sanger.ac.uk/cosmic)), the enrichment in MPUC is also highly significant (p<0.0001).

All 6ERBB2 mutations identified in MPUC in this study were localized to the extracellular domain, with five mutations at 5310 and no mutations within the tyrosine kinase domain. This contrasts with other tumor types where the majority of ERBB2 mutations are located within the kinase domain with a frequency in COSMIC of 78% in all tissues, 97% in lung adenocarcinoma and 81% in breast cancer (FIG. 3). The biological underpinnings of the extracellular domain location of the MUPC ERBB2 mutations are unclear and warrant further investigation.

In contrast, in lung cancer ERBB2 alterations are predominantly insertion mutations in the kinase with only a small fraction of alterations involving the extra-cellular domain (COSMIC v65 Release". *Catalogue Of Somatic Mutations In Cancer.* Wellcome Trust Sanger Institute. Retrieved 1 Jul. 2013 (http://www.sanger.ac.uk/cosmic). In breast cancer, although similar to lung cancer in the localization of the large majority of ERBB2 alterations to the kinase domain, insertions are relatively uncommon and virtually all of the kinase domain mutations are base substitutions (COSMIC v65 Release". *Catalogue Of Somatic Mutations In Cancer.* Wellcome Trust Sanger Institute. Retrieved 1 Jul. 2013 (http://www.sanger.ac.uk/cosmic). An enrichment of ERBB2 mutation within a common cancer subtype has also been recently described in a series of CDH1 mutated invasive lobular carcinomas of the breast with a frequency of 23% compared to a frequency of 2% in all breast cancers (Ross J. S., et al. (2013) *Clin Cancer Res.* 19:2668-76).

In the Bladder Urothelial Carcinoma TCGA dataset, although mutations in ERBB2 are not described, amplification of ERBB2 was listed in 6% (9/150) of cases (The cBio Cancer Genomics Portal, April 2013). Separate studies have reported ERBB2 amplification predominantly based of fluorescence in situ hybridization (FISH) analysis in 8-9% of primary urothelial carcinomas, and at a higher frequency in lymph node metastases (Fleischmann A, et al. (2011) *Eur Urol.* 60:350-7). In addition, in a study of non-muscle-invasive bladder cancers, ERBB2 amplification has been observed in high grade urothelial carcinomas (HG-UCs) at a similar incidence of 9%, but not in any of the papillary urothelial neoplasms of low malignant potential or low grade urothelial carcinomas (LG-UCs) studied, and has been associated with recurrence and progression in high grade UC (Chen P C, (2013) et al. *J Clin Pathol.* 66:113-9). Her2 overexpression has been identified in 19% (22/116) of bladder cancers, with significant enrichment in grade III and muscle invasive tumors Gardiner R A, et al. (1992) *Urol Res.* 20:117-20). However, studies have reported inconsistent results regarding the prognostic value of HER2 expression detected by IHC (Tsai Y S, et al. (2012) *Adv Urol.:* 181964). In the current study, 3 (100%) of ERBB2 mutated MPUC were negative for HER2 expression by IHC.

In addition to ERBB2 amplification, activating ERBB2 mutations can also predict sensitivity to anti-HER2-targeted therapies (Herter-Sprie G S, et al. *Front Oncol.* 2013; 3:86; Bose, et al. (2013) *Cancer Discov.* 3(2):224-37; Mazières J, et al. (2013) *J Clin Oncol.* 31:1997-2003; Ali S M, et al. (2013) *J Clin Oncol.* September 27 [Epub ahead of print). Irreversible HER2 (ERBB2) inhibitors are emerging and appear to show greater potency and durability than on the market reversible inhibitors in both clinical and preclinical settings (Bose, et al. (2013) *Cancer Discov.* 3(2):224-37; Mazières J, et al. (2013) *J Clin Oncol.* 31:1997-2003). The S310F/Y ERBB2 extra-cellular domain mutations seen in 5 cases of MPUC and 3 cases of UC is considered to be an activating mutation and sensitive to irreversible dual Egfr/Erbb2 inhibitors (Herter-Sprie G S, et al. (2013) *Front Oncol.* 3:86; Lee J C, et al. (2006) *PLoS Med.* 3:e485; Greulich H. et al. *Genes Cancer.* 2010; 1:1200-10; Greulich H, et al. (2012) *Proc Natl Acad Sci USA.* 109:14476-81). The kinase domain alterations in ERBB2 are considered to be homologous to those encountered in the EGFR gene (Greulich H. (2010) *Genes Cancer* 1:1200-10). The S310F/Y extracellular domain ERBB2 mutations found in the MPUC cases are not as comparable to EGFR extra-cellular domain mutations are, to date, not as well characterized as the insertion and base substitution mutations described in lung and breast cancers (COSMIC v65 Release". *Catalogue Of Somatic Mutations In Cancer.* Wellcome Trust Sanger Institute. Retrieved 1 Jul. 2013 (http://www.sanger.ac.uk/cosmic). Although the mechanism of receptor activation has not yet been characterized for these EGFR extracellular domain mutations, it is tempting to speculate that the underlying tumorigenic mechanism is caused by a less tethered conformation of the extracellular domain as most amino acid substitutions localize to inter-domain interfaces (Lee J C, et al. (2006) *PLoS Med* 3:e485).

Although the currently available anti-HER2 targeted therapies such as trastuzumab, lapatanib, and others are currently under investigation for treatment of ERBB2-amplified urothelial carcinomas, Phase 3 trial data has yet to emerge (Marín A P, et al. (2010) *J Cancer Res Clin Oncol.*

136:1915-20. For non-amplified bladder cancers such as the 6 ERBB2 mutated MPUC in the current study, the standard tests for HER2 (ERBB2) amplification/overexpression status (IHC and FISH) were uniformly negative and these aggressive tumors would thus not have been detected as being driven by ERBB2 activation. Given the promise of targeting ERBB2 mutated (HER2 IHC/FISH negative) tumors such as has recently started in the clinical trials setting for breast and lung cancers, the current study argues that this approach should be extended to urinary bladder cancer especially when the tumor features an MPUC pattern. The micropapillary architecture and well-documented aggressive clinical course attributed MPUC has also been linked to micropapillary carcinomas of the endometrium, breast and lung (del Carmen M G, et al. (2012) *Gynecol Oncol.* 127:651-61; Chen L, et al. (2008) *Int J Surg Pathol.;* 16:155-63; Kamiya K, et al. (2008) *Mod Pathol.* 21:992-1001). However, to date there has been no reported association of ERBB2 mutations in these other aggressive types of micropapillary carcinomas. This study illustrates the impact of histologic subtyping on the genomic landscape and the resulting potential to direct targeted therapies.

An exemplary amino acid and nucleotide sequence for human HER2 are provided herein as SEQ ID NO:1 and SEQ ID NO:2, respectively. SEQ ID NO:1 corresponds to a HER2 isoform that contains a signal peptide (amino acids 1-22). Residue Ser310 is highlighted.

```
NCBI Reference Sequence: NP_004439.2
                                                                  (SEQ ID NO: 1)
    1 melaalcrwg lllallppga astqvctgtd mklrlpaspe thldmlrhly qgcqvvqgnl 61 eltylptnas lsflqdiqev qgyvliahnq vrqvplqrlr ivrgtqlfed nyalavldng 121 dplnnttpvt gaspgglrel qlrslteilk ggvliqrnpq lcyqdtilwk difhknnqla 181 ltlidtnrsr achpcspmck gsrcwgesse dcqsltrtvc aggcarckgp lptdccheqc 241 aagctgpkhs dclaclhfnh sgicelhcpa lvtyntdtfe smpnpegryt fgascvtacp 301 ynylstdvgs ctlvcplhnq evtaedgtqr cekcskpcar vcyglgmehl revravtsan 361 iqefagckki fgslaflpes fdgdpasnta plqpeqlqvf etleeitgyl yisawpdslp 421 dlsvfqnlqv irgrilhnga ysltlqglgi swlglrslre lgsglalihh nthlcfvhtv 481 pwdqlfrnph qallhtanrp edecvgegla chqlcarghc wgpgptqcvn csqflrgqec 541 veecrvlqgl preyvnarhc lpchpecqpq ngsvtcfgpe adqcvacahy kdppfcvarc 601 psgvkpdlsy mpiwkfpdee gacqpcpinc thscvdlddk gcpaeqrasp ltsiisavvg 661 illvvvlgvv fgilikrrqq kirkytmrrl lqetelvepl tpsgampnqa qmrilketel 721 rkvkvlgsga fgtvykgiwi pdgenvkipv aikvlrents pkankeilde ayvmagvgsp 781 yvsrllgicl tstvqlvtql mpygclldhv renrgrlgsq dllnwcmqia kgmsyledvr 841 lvhrdlaarn vlvkspnhvk itdfglarll didetyhad ggkvpikwma lesilrrrft 901 hqsdvwsygv tvwelmtfga kpydgipare ipdllekger lpqppictid vymimvkcwm 961 idsecrprfr elvsefsrma rdpqrfvviq nedlgpaspl dstfyrslle dddmgdlvda 1021 eeylvpqqgf fcpdpapgag gmvhhrhrss strsgggdlt lglepseeea prsplapseg 1081 agsdvfdgdl gmgaakglqs lpthdpsplq rysedptvpl psetdgyvap ltcspqpeyv 1141 nqpdvrpqpp spregplpaa rpagatlerp ktlspgkngv vkdvfafgga venpeyltpq 1201 ggaapqphpp pafspafdnl yywdqdpper gappstfkgt ptaenpeylg ldvpv NCBI Reference Sequence: NM_004448.2
                                                                  (SEQ ID NO: 2)
    1 atggagctgg cggccttgtg ccgctggggg ctcctcctcg ccctcttgcc cccggagcc 61 gcgagcaccc aagtgtgcac cggcacagac atgaagctgc ggctccctgc cagtcccgag 121 acccacctgg acatgctccg ccacctctac cagggctgcc aggtggtgca gggaaacctg 181 gaactcacct acctgcccac caatgccagc ctgtccttcc tgcaggatat ccaggaggtg 241 cagggctacg tgctcatcgc tcacaaccaa gtgaggcagg tcccactgca gaggctgcgg 301 attgtgcgag gcacccagct ctttgaggac aactatgccc tggccgtgct agacaatgga 361 gacccgctga acaataccac ccctgtcaca ggggcctccc caggaggcct gcgggagctg 421 cagcttcgaa gcctcacaga gatcttgaaa ggaggggtct tgatccagcg gaaccccag 481 ctctgctacc aggacacgat tttgtggaag gacatcttcc acaagaacaa ccagctggct
```

-continued

```
 541 ctcacactga tagacaccaa ccgctctcgg gcctgccacc cctgttctcc gatgtgtaag 601 ggctcccgct gctggggaga gagttctgag gattgtcaga gcctgacgcg cactgtctgt 661 gccggtggct gtgcccgctg caaggggcca ctgcccactg actgctgcca tgagcagtgt 721 gctgccggct gcacgggccc caagcactct gactgcctgg cctgcctcca cttcaaccac 781 agtggcatct gtgagctgca ctgcccagcc ctggtcacct acaacacaga cacgtttgag 841 tccatgccca atcccgaggg ccggtataca ttcggcgcca gctgtgtgac tgcctgtccc 901 tacaactacc tttctacgga cgtgggatcc tgcaccctcg tctgcccct gcacaaccaa 961 gaggtgacag cagaggatgg aacacagcgg tgtgagaagt gcagcaagcc ctgtgcccga 1021 gtgtgctatg gtctgggcat ggagcacttg cgagaggtga gggcagttac cagtgccaat 1081 atccaggagt ttgctggctg caagaagatc tttgggagcc tggcatttct gccggagagc 1141 tttgatgggg acccagcctc caacactgcc ccgctccagc cagagcagct ccaagtgttt 1201 gagactctgg aagagatcac aggttaccta tacatctcag catggccgga cagcctgcct 1261 gacctcagcg tcttccagaa cctgcaagta atccggggac gaattctgca caatggcgcc 1321 tactcgctga ccctgcaagg gctgggcatc agctggctgg ggctgcgctc actgagggaa 1381 ctgggcagtg gactggccct catccaccat aacacccacc tctgcttcgt gcacacggtg 1441 ccctgggacc agctctttcg gaacccgcac caagctctgc tccacactgc caaccggcca 1501 gaggacgagt gtgtgggcga gggcctggcc tgccaccagc tgtgcgcccg agggcactgc 1561 tggggtccag gcccacccca gtgtgtcaac tgcagccagt tccttcgggg ccaggagtgc 1621 gtggaggaat gccgagtact gcaggggctc cccagggagt atgtgaatgc caggcactgt 1681 ttgccgtgcc accctgagtg tcagcccag aatggctcag tgacctgttt tggaccggag 1741 gctgaccagt gtgtggcctg tgcccactat aaggaccctc ccttctgcgt ggcccgctgc 1801 cccagcggtg tgaaacctga cctctcctac atgcccatct ggaagtttcc agatgaggag 1861 ggcgcatgcc agccttgccc catcaactgc acccactcct gtgtggacct ggatgacaag 1921 ggctgccccg ccgagcagag agccagccct ctgacgtcca tcatctctgc ggtggttggc 1981 attctgctgg tcgtggtctt gggggtggtc tttgggatcc tcatcaagcg acggcagcag 2041 aagatccgga agtacacgat gcggagactg ctgcaggaaa cggagctggt ggagccgctg 2101 acacctagcg gagcgatgcc caaccaggcg cagatgcgga tcctgaaaga gacggagctg 2161 aggaaggtga aggtgcttgg atctggcgct tttggcacag tctacaaggg catctggatc 2221 cctgatgggg agaatgtgaa aattccagtg gccatcaaag tgttgaggga aaacacatcc 2281 cccaaagcca acaaagaaat cttagacgaa gcatacgtga tggctggtgt gggctcccca 2341 tatgtctccc gccttctggg catctgcctg acatccacgg tgcagctggt gacacagctt 2401 atgcccatg gctgcctctt agaccatgtc cgggaaaacc gcggacgcct gggctcccag 2461 gacctgctga actggtgtat gcagattgcc aaggggatga gctacctgga ggatgtgcgg 2521 ctcgtacaca gggacttggc cgctcggaac gtgctggtca agagtcccaa ccatgtcaaa 2581 attacagact cgggctggc tcggctgctg acattgacg agacagagta ccatgcagat 2641 gggggcaagg tgcccatcaa gtggatggcg ctggagtcca ttctccgccg gcggttcacc 2701 caccagagtg atgtgtggag ttatggtgtg actgtgtggg agctgatgac ttttggggcc 2761 aaaccttacg atgggatccc agcccgggag atccctgacc tgctggaaaa ggggagcggg 2821 ctgccccagc cccccatctg caccattgat gtctacatga tcatggtcaa atgttggatg 2881 attgactctg aatgtcggcc aagattccgg gagttggtgt ctgaattctc ccgcatggcc
```

```
2941 agggaccccc agcgctttgt ggtcatccag aatgaggact tgggcccagc cagtcccttg 3001 gacagcacct tctaccgctc actgctggag gacgatgaca tgggggacct ggtggatgct 3061 gaggagtatc tggtacccca gcagggcttc ttctgtccag accctgcccc gggcgctggg 3121 ggcatggtcc accacaggca ccgcagctca tctaccagga gtggcggtgg ggacctgaca 3181 ctagggctgg agccctctga agaggaggcc cccaggtctc cactggcacc ctccgaaggg 3241 gctggctccg atgtatttga tggtgacctg ggaatggggg cagccaaggg gctgcaaagc 3301 ctccccacac atgacccag ccctctacag cggtacagtg aggacccac agtaccctg 3361 ccctctgaga ctgatggcta cgttgccccc ctgacctgca gccccagcc tgaatatgtg 3421 aaccagccag atgttcggcc ccagcccct tcgccccgag agggccctct gcctgctgcc 3481 cgacctgctg gtgccactct ggaaaggccc aagactctct ccccagggaa gaatggggtc 3541 gtcaaagacg ttttttgcctt tgggggtgcc gtggagaacc ccgagtactt gacaccccag 3601 ggaggagctg cccctcagcc ccaccctcct cctgccttca gcccagcctt cgacaacctc 3661 tattactggg accaggaccc accagagcgg ggggctccac ccagcacctt caaagggaca 3721 cctacggcag agaacccaga gtacctgggt ctggacgtgc cagtgtga
```

EQUIVALENTS

Those skilled in the art will recognize, or be able to ascertain using no more than routine experimentation, many equivalents to the specific embodiments described herein. Such equivalents are intended to be encompassed by the following claims.

We claim:

1. A method of treating a subject having a micropapillary urothelial or a bladder carcinoma that lacks HER2 gene amplification, comprising:
   (i) identifying the carcinoma as having a HER2 kinase activating mutation in the extracellular domain at residue 310 or at residue 157 of HER2;
   (ii) identifying the carcinoma as having a micropapillary histology; and
   (iii) administering to the subject an effective amount of an agent that inhibits HER2 expression or activity, thereby treating the carcinoma.

2. The method of claim 1, wherein the subject is a human.

3. The method of claim 1, wherein the subject does not have, or is identified as not having, an elevated level of a HER2 gene product.

4. The method of claim 1, wherein the HER2 kinase activating mutation is chosen from:
   (i) a substitution at residue 310 of HER2;
   (ii) a substitution of a serine residue at position 310 (S310) of HER2 to phenylalanine;
   (iii) a substitution of a serine residue at position 310 (S310) of HER2 to tyrosine;
   (iv) a substitution at residue 157; or
   (v) a substitution of an arginine residue at position 157 (R157) of HER2 to tryptophan.

5. The method of claim 1, wherein the subject is undergoing or has undergone a treatment with a non-HER2 therapeutic agent or therapeutic modality.

6. The method of claim 5, wherein the non-HER2 therapeutic agent or therapeutic modality comprises one or more of: methotrexate, vinblastine, doxorubicin, or cisplatin.

7. The method of claim 5, wherein, responsive to a determination of the presence of the HER2 kinase activating mutation, the non-HER2 therapeutic agent or therapeutic modality is discontinued.

8. The method of claim 5, wherein the agent that inhibits HER2 expression or activity is administered after cessation of the non-HER2 therapeutic agent or therapeutic modality.

9. The method of claim 1, wherein the agent that inhibits HER2 expression or activity is chosen from one or more of: a kinase inhibitor; a multi-specific kinase inhibitor; a HER2-specific inhibitor; an EGFR inhibitor; a reversible or an irreversible HER2 inhibitor; a pan ERBB inhibitor; a small molecule inhibitor that is selective for HER2; an antibody molecule; a monoclonal or a bispecific antibody against HER2; an antibody to HER2 conjugated to a cytotoxic agent; or a HER2 cellular immunotherapy.

10. The method of claim 1, wherein the agent that inhibits HER2 expression or activity is an anti-HER2 antibody molecule, or a conjugate thereof.

11. The method of claim 1, wherein the agent that inhibits HER2 expression or activity is chosen from one or more of: AV-203, AMG 888, U3-1287, APC8024, DN24-02, Neuvenge, Lapuleucel-T, MM-111, MM-121, SAR256212, MM-141, LJM716, REGN1400, MEHD7945A, RG7597, RG7116, Trastuzumab, trastuzumab emtansine (T-DM1), pertuzumab, afatinib, TAK-285, Neratinib, Dacomitinib, BMS-690514, BMS-599626, Pelitinib, CP-724714, Lapatinib, TAK-165, ARRY-380, AZD8931, or Neratinib.

12. The method of claim 1, wherein the HER2 comprises the amino acid sequence of SEQ ID NO: 1.

13. The method of claim 3, wherein the subject does not have an elevated level of a HER2 gene product.

14. The method of claim 3, wherein the subject is identified as not having an elevated level of a HER2 gene product.

15. The method of claim 4, wherein the HER2 kinase activating mutation is a substitution at residue 157 of HER2.

16. A method of treating a subject having a micropapillary carcinoma that lacks HER2 gene amplification, comprising administering to the subject an effective amount of an agent that inhibits HER2 expression or activity, wherein:
   (i) the carcinoma has a HER2 kinase activating mutation at residue 310 or residue 157 of HER2; and
   (ii) the carcinoma is chosen from a cancer of the urinary tract, bladder, or urothelial cells,
   thereby treating the carcinoma.

17. The method of claim 16, wherein the subject does not have a gene amplification or overexpression of HER2 or a HER2 gene product.

18. The method of claim 16, wherein the subject is identified as not having a gene amplification or overexpression of HER2 or a HER2 gene product.

19. The method of claim 16, wherein the subject does not have, or is identified as not having, an elevated level of a HER2 gene product.

20. The method of claim 16, wherein the subject is a human.

21. The method of claim 16, wherein the subject is undergoing or has undergone treatment with a non-HER2 therapeutic agent or therapeutic modality that comprises one or more of: methotrexate, vinblastine, doxorubicin, or cisplatin.

22. The method of claim 21, wherein, responsive to the determination of the presence of one or both of the HER2 kinase activating mutation or a micropapillary histology in the carcinoma, the non-HER2 therapeutic agent or therapeutic modality is discontinued.

23. The method of claim 21, wherein the agent that inhibits HER2 expression or activity is administered after cessation of the non-HER2 therapeutic agent or therapeutic modality.

24. The method of claim 16, wherein the agent that inhibits HER2 expression or activity is chosen from one or more of: a kinase inhibitor; a multi-specific kinase inhibitor; a HER2-specific inhibitor; an EGFR inhibitor; a reversible or an irreversible HER2 inhibitor; a pan ERBB inhibitor; a small molecule inhibitor that is selective for HER2; an antibody molecule; a monoclonal or a bispecific antibody against HER2; an antibody to HER2 conjugated to a cytotoxic agent; or a HER2 cellular immunotherapy.

25. The method of claim 16, wherein the agent that inhibits HER2 expression or activity is an anti-HER2 antibody molecule, or a conjugate thereof.

26. The method of claim 16, wherein the agent that inhibits HER2 expression or activity is chosen from one or more of: AV-203, AMG 888, U3-1287, APC8024, DN24-02, Neuvenge, Lapuleucel-T, MM-111, MM-121, SAR256212, MM-141, LJM716, REGN1400, MEHD7945A, RG7597, RG7116, Trastuzumab, trastuzumab emtansine (T-DM1), pertuzumab, afatinib, TAK-285, Neratinib, Dacomitinib, BMS-690514, BMS-599626, Pelitinib, CP-724714, Lapatinib, TAK-165, ARRY-380, AZD8931, or Neratinib.

27. The method of claim 16, wherein the agent that inhibits HER2 expression or activity is chosen from an antisense molecule, a ribozyme, a double stranded RNA, or a triple helix molecule, wherein the agent hybridizes to and/or inhibits a HER2 nucleic acid, or a transcription regulatory region that blocks or reduces mRNA expression of the nucleic acid encoding a HER2 gene product with a HER2 kinase activating mutation.

28. The method of claim 16, wherein the HER2 kinase activating mutation is detected by sequencing.

29. The method of claim 16, wherein the HER2 kinase activating mutation is detected in a nucleic acid molecule acquired from the subject, wherein said nucleic acid molecule is present in a circulating cell; a urothelial or micropapillary carcinoma; or a blood or plasma sample.

30. The method of claim 16, wherein the HER2 kinase activating mutation is chosen from:
(i) a substitution at residue 310 of HER2;
(ii) a substitution of a serine residue at position 310 (S310) of HER2 to phenylalanine or tyrosine of HER2;
(iii) a substitution at residue 157 of HER2; or
(iv) a substitution of an arginine residue at position 157 (R157) of HER2 to tryptophan, wherein the HER2 comprises the amino acid sequence of SEQ ID NO:1.

31. The method of claim 30, wherein the HER2 kinase activating mutation is a substitution of a serine residue at position 310 (S310) of HER2 to phenylalanine or tyrosine.

32. The method of claim 31, wherein the HER2 kinase activating mutation is detected by sequencing.

33. The method of claim 30, wherein the agent that inhibits HER2 expression or activity is administered responsive to a determination of the presence of the HER2 kinase activating mutation in the carcinoma.

34. The method of claim 30, wherein the HER2 kinase activating mutation is detected in a nucleic acid molecule acquired from the subject, wherein said nucleic acid molecule is present in a circulating cell, a urothelial or micropapillary carcinoma, or a blood or plasma sample.

35. The method of claim 30, wherein the HER2 kinase activating mutation is a substitution at residue 310 of HER2.

36. The method of claim 16, wherein the HER2 kinase activating mutation is a substitution at residue 310 of HER2.

37. The method of claim 16, wherein the HER2 kinase activating mutation is a substitution at residue 157 of HER2.

38. A method of treating a subject having a micropapillary carcinoma chosen from a cancer of the urinary tract, bladder, or urothelial cells, said method comprising:
(i) identifying the carcinoma as having a HER2 kinase activating mutation in the extracellular domain at residue 310 or at residue 157 of HER2; and
(ii) administering to the subject an effective amount of an agent that inhibits HER2, wherein the agent is chosen from one or more of a kinase inhibitor, an antibody molecule, or a HER2 cellular immunotherapy; and
wherein the carcinoma does not have an elevated level of a HER2 gene product,
thereby treating the micropapillary carcinoma.

39. The method of claim 38, wherein the agent that inhibits HER2 is chosen from one or more of: AV-203, AMG 888, U3-1287, APC8024, DN24-02, Neuvenge, Lapuleucel-T, MM-111, MM-121, SAR256212, MM-141, LJM716, REGN1400, MEHD7945A, RG7597, RG7116, Trastuzumab, trastuzumab emtansine (T-DM1), pertuzumab, afatinib, TAK-285, Neratinib, Dacomitinib, BMS-690514, BMS-599626, Pelitinib, CP-724714, Lapatinib, TAK-165, ARRY-380, AZD8931, or Neratinib.

40. The method of claim 38, wherein the HER2 kinase activating mutation is chosen from:
(i) a substitution at residue 310 of HER2;
(ii) a substitution of a serine residue at position 310 (S310) of HER2 to phenylalanine;
(iii) a substitution of a serine residue at position 310 (S310) of HER2 to tyrosine;
(iv) a substitution at residue 157 of HER2; or
(v) a substitution of an arginine residue at position 157 (R157) of HER2 to tryptophan.

41. The method of claim 40, wherein the HER2 kinase activating mutation is a substitution at residue 310 of HER2.

42. The method of claim 41, wherein the HER2 kinase activating mutation is a substitution of residue 5310 of HER2 to phenylalanine or tyrosine.

43. The method of claim 40, wherein the HER2 comprises the amino acid sequence of SEQ ID NO: 1.

44. The method of claim 38, wherein the HER2 comprises the amino acid sequence of SEQ ID NO: 1.

45. The method of claim 38, wherein the agent that inhibits HER2 is an anti-HER2 antibody molecule, or a conjugate thereof.

46. The method of claim 38, wherein the subject is a human.

47. The method of claim 38, wherein the carcinoma is identified as not having an elevated level of a HER2 gene product.

48. The method of claim 47, wherein the carcinoma is identified as having a micropapillary histology.

49. The method of claim 40, wherein the HER2 kinase activating mutation is a substitution at residue 157 of HER2.

* * * * *